(12) United States Patent
Mathis et al.

(10) Patent No.: US 11,555,198 B2
(45) Date of Patent: Jan. 17, 2023

(54) METHOD FOR MAKING NICOTIANA PLANTS WITH MUTATIONS IN XYLT AND FUCT ALLELES USING RARE-CUTTING ENDONUCLEASES

(71) Applicants: CELLECTIS SA, Paris (FR);
MEDICAGO INC., Quebec (CA)

(72) Inventors: Luc Mathis, Le Kremlin Bicetre (FR);
Daniel F. Voytas, Falcon Heights, MN (US); Jin Li, Shoreview, MN (US);
Feng Zhang, Plymouth, MN (US);
Thomas Stoddard, St. Louis Park, MN (US); Marc-Andre D'Aoust, Quebec (CA)

(73) Assignees: CELLECTIS SA, Paris (FR);
MEDICAGO INC., Quebec (CA)

( * ) Notice: Subject to any disclaimer, the term of this patent is extended or adjusted under 35 U.S.C. 154(b) by 0 days.

(21) Appl. No.: 14/439,420

(22) PCT Filed: Oct. 31, 2013

(86) PCT No.: PCT/US2013/067810
§ 371 (c)(1),
(2) Date: Apr. 29, 2015

(87) PCT Pub. No.: WO2014/071039
PCT Pub. Date: May 8, 2014

(65) Prior Publication Data
US 2015/0272076 A1    Oct. 1, 2015

Related U.S. Application Data

(60) Provisional application No. 61/721,194, filed on Nov. 1, 2012, provisional application No. 61/790,850, filed on Mar. 15, 2013.

(51) Int. Cl.
| | |
|---|---|
| *A01H 1/06* | (2006.01) |
| *C12N 15/82* | (2006.01) |
| *C12N 15/01* | (2006.01) |
| *C12N 9/22* | (2006.01) |
| *C12P 21/00* | (2006.01) |

(52) U.S. Cl.
CPC .......... *C12N 15/8218* (2013.01); *A01H 1/06* (2013.01); *C12N 9/22* (2013.01); *C12N 15/01* (2013.01); *C12N 15/8257* (2013.01); *C12P 21/005* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,162,602 A | 11/1992 | Somers et al. |
| 5,204,253 A | 4/1993 | Sanford et al. |
| 5,276,268 A | 1/1994 | Strauch et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,501,967 A | 3/1996 | Offringa et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,767,366 A | 6/1998 | Sathasivan et al. |
| 5,792,640 A | 8/1998 | Chandrasegaran |
| 5,879,903 A | 3/1999 | Strauch et al. |
| 5,928,937 A | 7/1999 | Kakefuda et al. |
| 6,084,155 A | 7/2000 | Volrath et al. |
| 6,326,166 B1 | 12/2001 | Pomerantz et al. |
| 6,329,571 B1 | 12/2001 | Hiei |
| 6,368,227 B1 | 4/2002 | Olson |
| 6,451,732 B1 | 9/2002 | Beckett et al. |
| 6,451,735 B1 | 9/2002 | Ottaway et al. |
| 6,824,978 B1 | 11/2004 | Cox, III et al. |
| 6,933,113 B2 | 8/2005 | Case et al. |

(Continued)

FOREIGN PATENT DOCUMENTS

| | | |
|---|---|---|
| CA | 2850571 | 4/2013 |
| EP | 0 242 246 | 10/1987 |

(Continued)

OTHER PUBLICATIONS

Li et al. TAL nucleases (TALNs): hybrid proteins composed of TAL effectors and FokI DNA-cleavage domain. (2011) Nucleic Acids Research; vol. 39; pp. 359-372.*
Cedeno et al. Protein delivery into plant cells: toward in vivo structural biology. (2017) Frontiers in Plant Science; vol. 8; pp. 1-14 (Year: 2017).*
Bogdanove et al. TAL effectors: customizable proteins for DNA targeting. (2011) Science; vol. 333; pp. 1843-1846. (Year: 2011).*
U.S. Appl. No. 61/225,043, filed Jul. 13, 2009, Bonas et al.

(Continued)

*Primary Examiner* — Cathy Kingdon Worley
(74) *Attorney, Agent, or Firm* — Ballard Spahr LLP

(57) ABSTRACT

Materials and methods are provided for making plants (e.g., *Nicotiana* varieties) that are suitable for producing therapeutic polypeptides suitable for administration to humans and animals, particularly by making TAL effector endonuclease-induced mutations in genes encoding xylosyltransferases and fucosyltransferases.

8 Claims, 11 Drawing Sheets

Specification includes a Sequence Listing.

(56) References Cited

U.S. PATENT DOCUMENTS

| | | | |
|---|---|---|---|
| 6,979,539 B2 | 12/2005 | Cox, III et al. | |
| 7,001,768 B2 | 2/2006 | Wolffe | |
| 7,013,219 B2 | 3/2006 | Case et al. | |
| 7,067,722 B2 | 6/2006 | Fillatti | |
| 7,070,934 B2 | 7/2006 | Cox, III et al. | |
| 7,163,824 B2 | 1/2007 | Cox, III et al. | |
| 7,189,691 B2 | 3/2007 | Hemenway | |
| 7,220,719 B2 | 5/2007 | Case et al. | |
| 7,262,054 B2 | 8/2007 | Jamieson et al. | |
| 7,273,923 B2 | 9/2007 | Jamieson et al. | |
| 7,285,416 B2 | 10/2007 | Choo et al. | |
| 7,361,635 B2 | 4/2008 | Miller et al. | |
| 7,521,241 B2 | 4/2009 | Choo et al. | |
| 7,842,489 B2 | 11/2010 | Arnould et al. | |
| 8,420,782 B2 | 4/2013 | Bonas et al. | |
| 8,440,431 B2 | 5/2013 | Voytas et al. | |
| 8,440,432 B2 | 5/2013 | Voytas et al. | |
| 8,450,471 B2 | 5/2013 | Voytas et al. | |
| 8,586,363 B2 | 11/2013 | Voytas et al. | |
| 8,592,645 B2 | 11/2013 | DeKelver | |
| 8,697,853 B2 | 4/2014 | Voytas et al. | |
| 2001/0016956 A1 | 8/2001 | Ward et al. | |
| 2005/0064474 A1 | 3/2005 | Umov et al. | |
| 2007/0141038 A1 | 6/2007 | Choulika et al. | |
| 2009/0060921 A1 | 3/2009 | Dickey et al. | |
| 2009/0133158 A1 | 5/2009 | Lahaye et al. | |
| 2009/0271881 A1 | 10/2009 | Arnould et al. | |
| 2009/0305402 A1 | 12/2009 | Liljedahl et al. | |
| 2010/0132069 A1 | 5/2010 | Lahaye et al. | |
| 2010/0154081 A1 | 6/2010 | Weterings et al. | |
| 2011/0041195 A1 | 2/2011 | Doyon | |
| 2011/0129898 A1 | 6/2011 | Doyon et al. | |
| 2011/0136895 A1 | 6/2011 | Gregory et al. | |
| 2011/0145940 A1 | 6/2011 | Voytas et al. | |
| 2011/0158957 A1 | 6/2011 | Bonini et al. | |
| 2011/0167521 A1 | 7/2011 | DeKelver et al. | |
| 2011/0201055 A1 | 8/2011 | Doyon et al. | |
| 2011/0201118 A1 | 8/2011 | Yang et al. | |
| 2011/0203012 A1 | 8/2011 | Dotson et al. | |
| 2011/0207221 A1 | 8/2011 | Cost et al. | |
| 2011/0239315 A1 | 9/2011 | Bonas et al. | |
| 2011/0247089 A1 | 10/2011 | Doyon | |
| 2011/0265198 A1 | 10/2011 | Gregory et al. | |
| 2011/0269234 A1 | 11/2011 | Doyon et al. | |
| 2011/0287545 A1 | 11/2011 | Cost et al. | |
| 2011/0301073 A1 | 12/2011 | Gregory et al. | |
| 2012/0110685 A1 | 5/2012 | Bonas et al. | |
| 2012/0122205 A1 | 5/2012 | Bonas et al. | |
| 2012/0178131 A1 | 7/2012 | Voytas et al. | |
| 2012/0178169 A1 | 7/2012 | Voytas et al. | |
| 2012/0214228 A1 | 8/2012 | Voytas et al. | |
| 2012/0246764 A1 | 9/2012 | Hlubek et al. | |
| 2012/0284877 A1 | 11/2012 | Hlubek et al. | |
| 2012/0324603 A1 | 12/2012 | Hlubek et al. | |
| 2013/0122581 A1 | 5/2013 | Voytas et al. | |
| 2015/0080553 A1* | 3/2015 | Weterings | C12N 9/1051 530/379 |
| 2015/0093782 A1 | 4/2015 | Mabashi-Asazuma | |

FOREIGN PATENT DOCUMENTS

| | | | |
|---|---|---|---|
| EP | 2 206 723 | 7/2010 | |
| EP | 2 392 208 | 12/2011 | |
| EP | 2 562 260 | 2/2013 | |
| WO | WO 1994/18313 | 8/1994 | |
| WO | WO 1995/09233 | 4/1995 | |
| WO | WO 2004/067736 | 8/2004 | |
| WO | WO 2007/060495 | 5/2007 | |
| WO | WO 2007/084922 | 7/2007 | |
| WO | WO 2008/141806 | 11/2008 | |
| WO | WO 2009/056155 | * 5/2009 | C12N 9/10 |
| WO | WO 2009/095793 | 8/2009 | |
| WO | WO 2010/079430 | 7/2010 | |
| WO | WO 2010/091018 | 8/2010 | |
| WO | WO 2010/145846 | 12/2010 | |
| WO | WO 2011/017293 | 2/2011 | |
| WO | WO 2011/019385 | 2/2011 | |
| WO | WO 2011/072246 | 6/2011 | |
| WO | WO 2011/100058 | 8/2011 | |
| WO | WO 2011/117249 | * 9/2011 | C12N 9/10 |
| WO | WO 2011/146121 | 11/2011 | |
| WO | WO 2011/154393 | 12/2011 | |
| WO | WO 2013/050155 | 4/2013 | |
| WO | WO 2014/039692 | 3/2014 | |
| WO | WO 2014/039702 | 3/2014 | |

OTHER PUBLICATIONS

International Search Report and Written Opinion in International Application No. PCT/US2013/067810, dated Jan. 7, 2014, 15 pages.

"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).

Alam and Sittman, "Characterization of the cytotoxic effect of a chimeric restriction enzyme, H1°-FokI," Gene Ther Mol Biol, 10:147-160, 2006.

Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.

Al-Saadi et al., "All five host-range variants of Xanthomonas citri carry one pthA homolog with 17.5 repeats that determines pathogenicity on citrus, but none determine host-range variation," Mol Plant Microbe Interact, 20(8): 934-943, 2007.

Antony et al., "Rice xal3 recessive resistance to bacterial blight is defeated by induction of the disease susceptibility gene Os-11N3," Plant Cell, 22(11):3864-3876, 2010.

Antony, "Molecular basis of avrXa7 mediated virulence in bacterial blight of rice," [abstract of dissertation] Kansas State University, 99 pages, 2010.

Arimondo et al., "Exploring the cellular activity of camptothecin-triple-helix-forming oligonucleotide conjugates," Mol Cell Biol, 26:324-333, 2006.

Athinuwat et al., "*Xanthomonas axonopodis* pv. glycines soybean cultivar virulence specificity is determined by avrBs3 homolog avrXgl," Phytopathology, 99(8):996-1004, 2009.

Bai et al., "*Xanthomonas oiyzae* pv. oryzae avirulence genes contribute differently and specifically to pathogen aggressiveness," Mol Plant Microbe Interact, 13(12):1322-1329, 2000.

Baker, "Gene-editing nucleases," *Nature Methods*, 2012, 9:23-26.

Ballvora et al., "Genetic mapping and functional analysis of the tomato Bs4 locus governing recognition of the *Xanthomonas campestris* pv. vesicatoria AvrBs4 protein," Mol Plant Microbe Interact, 14(5):629-638, 2001.

Belahj et al., "Plant genome editing made easy: targeted mutagenesis in model and crop plants using the CRISPR/Cas system," *Plant Methods*, 9:39 (2013).

Beretta et al., "Tethering a type IB topoisomerase to a DNA site by enzyme fusion to a heterologous site-selective DNA-binding protein domain," Cancer Res, 59:3689-3697, 1999.

Bethke and Busse, "Validation of a simple, colorimetric, microplate assay using amplex red for the determination of glucose and sucrose in potato tubers and other vegetables," *Am. J. Pot Res.*, 85:414-421 (2008).

Beuselinck et al., "An Assessment of Phenotype Selection for Linolenic Acid Using Genetic Markers," *Crop Sci*, 47:747-750 (2006).

Bhaskar et al., "Suppression of the vacuolar invertase gene prevents cold-induced sweetening in potato," *Plant Physiol.*, 154(2):939-948 (Oct. 2010).

Bibikova et al., "Enhancing gene targeting with designed zinc finger nucleases," Science, 300(5620):764, 2003.

Bibikova et al., "Stimulation of homologous recombination through targeted cleavage by chimeric nucleases," Mol Cell Biol, 21(1): 289-297, 2001.

(56) References Cited

OTHER PUBLICATIONS

Bitinaite et al., "FokI dimerization is required for DNA cleavage," Proc Natl Acad Sci USA, 95:10570-10575, 1998.
Boch and Bonas. "Xanthomonas AvrBs3 family-type III effectors: discovery and function." Annu Rev Phytopathol, 48, 419-436, 2010.
Boch et al., "Breaking the code of DNA binding specificity of TAL-type III effectors," Science, 326:1509-1512, 2009.
Boch et al., "Molecular characterization of three AvrBs3-like effectors from the *Arabidopsis* pathogen *Xanthomonas campestris* pv. armoraciae," (abstract), XIV International Congress on Molecular Plant-Microbe Interactions, Quebec City, Canada, Jul. 19-23, 2009, 2 pages.
Bogdanove et al., "TAL Effectors: Customizable Proteins for DNA Targeting," *Science*, Sep. 29, 2011, 333(6051):1843-1846.
Bogdanove et al., "TAL effectors: finding plant genes for disease and defense," Curr Opin Plant Biol, 13:394-401, 2010.
Boller and He, "Innate immunity in plants: an arms race between pattern recognition receptors in plants and effectors in microbial pathogens," Science, 324:742-744, 2009.
Bonas et al., "Resistance in tomato to *Xanthomonas campestris* pv vesicatoria is determined by alleles of the pepper-specific avirulence gene avrBs3," Mol Gen Genet, 328: 261-269, 1993.
Bonas et al., "Genetic and structural characterization of the avirulence gene avrBs3 from *Xanthomonas campestris* pv. Vesicatoria," Mol Gen Genet, 218:127-136, 1989.
Bonas et al., "How the bacterial plant pathogen *Xanthomonas campestris* pv. vesicatoria conquers the host," Mol Plant Pathol, 1(1):73-76, 2000.
Bonas et al., "Resistance in tomato to *Xanthomonas campestris* pv vesicatoria is determined by alleles of the pepper-specific avirulence gene avrBs3," Mol Gen Genet, 238(1-2):261-269, 1993.
Bonar, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-2394, 2000.
Busk, "Regulatory elements in vivo in the promoter of the abscisic acid responsive gene rab17 from maize," Plant J, 11:1285-1295, 1997.
Büttner and Bonas, "Getting across—bacterial type III effector proteins on their way to the plant cell," EMBO J, 2002, 21(20):5313-5322, 2002.
Büttner et al., "Functional analysis of HrpF, a putative type III translocon protein from *Xanthomonas campestris* pv. vesicatoria," J Bacteriol, 184(9):2389-2398, 2002.
Büttner et al., "HpaB from *Xanthomonas campestris* pv. vesicatoria acts as an exit control protein in type III-dependent protein secretion," Mol Microbiol, 54(3):755-768, 2004.
Büttner et al., "Targeting of two effector protein classes to the type III secretion system by a HpaC- and HpaB-dependent protein complex from *Xanthomonas campestris* pv. vesicatoria," Mol Microbiol, 59(2):513-527, 2006.
Canteros et al., "A gene from *Xanthomonas campestris* pv. vesicatoria that determines avirulence in tomato is related to avrBs3," Mol Plant Microbe Interact, 4(6):628-632, 1991.
Carlson et al., "Targeting DNA With Fingers and TALENs," Mol Ther Nucl Acids, 1:e3, doi:10.1038/mtna.2011.5, 4 pages, 2012.
Cathomen et al., "Zinc-finger nucleases: the next generation emerges," Mol Ther, 16(7):1200-1207, 2008.
Cavalier et al., "Disrupting Two *Arabidopsis thaliana* Xylosyltransferase Genes Results in Plants Deficient in Xyloglucan, a Major Primary Cell Wall Component," *The Plant Cell*, Jun. 2008, 20:1519-1537.
Cermak et al., "Efficient design and assembly of custom TALEN and other TAL effector-based constructs for DNA targeting," *Nucleic Acids Research*, Jul. 2011, 39(12):e82, 11 pages.
Cermak et al., Poster and Abstract—"Engineered TAL effector nucleases: new tools for genome editing," Northwest Genome Engineering Consortium Workshop on Genome Engineering, 3 pages, 2010.

Chevalier et al., "Design, activity, and structure of a highly specific artificial endonuclease," Mol Cell, 10(4):895-905, 2002.
Choo et al., "In vivo repression by a site-specific DNA-binding protein designed against an oncogenic sequences," Nature, 372(6507):642-645, 1994.
Choulika et al., "Induction of homologous recombination in mammalian chromosomes by using the I-SceI system of *Saccharomyces cerevisiae*," Mol Cell Biol, 15(4):1968-1973, 1995.
Christian et al., "Targeting DNA double-strand breaks with TAL effector nucleases," *Genetics*, 2010, 186:757-761.
Christian et al., Poster and Abstract—"Fusions of TAL effectors to the FokI endonuclease confer site specificity in DNA cleavage," IAPB 12th World Congress and In Vitro Biology Meeting, 4 pages, Jun. 2010.
Cole et al., "The Jpred 3 secondary structure prediction server," Nucl Acids Res, 36:W197-W201, 2008.
Cornelis, "The type III secretion injectisome," Nat Rev Microbiol, 4:811-825, 2006.
Curtin et al., "Targeted mutagenesis of duplicated genes in soybean with zinc-finger nucleases," *Plant Physiology*, 156(2):466-473 (2011).
De Feyter et al., "Gene-for genes interactions between cotton R genes and *Xanthomonas campestris* pv. malvacearum avr genes," Mol Plant Microbe Interact, 6(2):225-237, 1993.
DeFrancesco, "Move over ZFNs," Nat Biotechnol, 29: 681-684, 2011.
Desjarlais and Berg, "Toward rules relating zinc finger protein sequences and DNA binding site preferences," Proc Natl Acad Sci USA, 89:7345-7349, 1992.
Domingues et al., "The Xanthomonas citri effector protein PthA interacts with citrus proteins involved in nuclear transport, protein folding and ubiquitination associated with DNA repair," Mol Plant Pathol, 11(5):663-675, DOI : 10.1111/ J .1364-3703.2010.00636.X, 13 pages, 2010.
Doyle et al., "TAL Effector-Nucleotide Targeter (TALE-NT) 2.0: tools for TAL effector design and target prediction," *Nucleic Acids Research*, 2012, 40:117-122.
Draffehn et al., "Natural diversity of potato (*Solanum tuberosum*) invertases," BMC Plant Biol., 10:271, 15 pages (2010).
Durai et al., "Zinc finger nucleases: custom-designed molecular scissors for genome engineering of plant and mammalian cells," Nucl Acids Res, 33(1): 5978-5990, 2005.
Eisenschmidt et al., "Developing a programmed restriction endonuclease for highly specific DNA cleavage," Nucl Acids Res, 33:7039-7047, 2005.
Engler et al. "A One Pot, One Step, Precision Cloning Method with High Throughput Capability," PLoS One, 3: e3647, 7 pages, 2008.
Engler et al., "Golden Gate Shuffling: A One-Pot DNA Shuffling Method Based on Type Its Restriction Enzymes," PLoS One, 4:e5553, 9 pages, 2009.
Fajardo-Sanchez et al., "Computer design of obligate heterodimer meganucleases allows efficient cutting of custom DNA sequences," Nucl Acids Res, 36(7):2163-2173, 2008.
Foley et al., "Rapid Mutation of Endogenous Zebrafish Genes Using Zinc Finger Nucleases Made by Oligomerized Pool ENgineering (OPEN)," PLoS One, 13 pages, 4:e4348, 2009.
Fonfara et al., "Creating highly specific nucleases by fusion of active restriction endonucleases and catalytically inactive homing endonucleases," Nucl Acids Res, 40(2):847-860, 2011.
Fujikawa et al., "Suppression of defense response in plants by the avrBs3/pthA gene family of *Xanthomonas* spp," Mol Plant Microbe Interact, 19(3):342-349, 2006.
Gabriel et al.,"An unbiased genome-wide analysis of zinc-finger nuclease specificity," Nat Biotechnol, 29:816-823, 2011.
Geißler et al., "Transcriptional activators of human genes with programmable DNA-specificity," PLoS One, 6(5):e19509, May 2011.
GenBank Accession No. AAT46122, Nov. 12, 2004, 2 pages.
GenBank Accession No. ACD58243, May 19, 2008, 2 pages.
GenBank Accession No. AY986492, Jun. 24, 2005, 2 pages.
GenBank Accession No. CP000967, GI: 188518722, May 19, 2008, 606 pages.
GenBank Accession No. J04623, Apr. 26, 1993, 2 pages.
GenBank Accession No. M28828, Apr. 26, 1993, 3 pages.

(56) References Cited

OTHER PUBLICATIONS

GenBank Accession No. P14727, Jun. 28, 2011, 3 pages.
GenBank Accession No. X16130, Oct. 15, 2007, 3 pages.
Göhre and Robatzek, "Breaking the barriers: microbial effector molecules subvert plant immunity," Ann Rev Phytopathol, 46:189-215, 2008.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005, Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.
Gonzalez et al., "Molecular and pathotypic characterization of new Xanthomonas oryzae strains from West Africa," Mol Plant Microbe Interact, 20(5):534-546, 2007.
Govindarajulu et al., "Evaluation of constitutive viral promoters in transgenic soybean roots and nodules," *Mol. Plant Microbe Interact,* 21:1027-1035 (2008).
Greiner et al., "Ectopic expression of a tobacco invertase inhibitor homolog prevents cold-induced sweetening of potato tubers," *Nature Biotechnology,* 17(7):708-711 (1999).
Greisman and Pabo, "A general strategy for selecting high-affinity zinc finger proteins for diverse DNA target sites," *Science,* 275(5300):657-661, 1997.
Gu et al., "R gene expression induced by a type-III effector triggers disease resistance in rice," *Nature,* 2005, 435:1122-1125.
Gu et al., "Transcription activator-like type III effector AvrXa27 depends on OsTFIIAgamma5 for the activation of Xa27 transcription in rice that triggers disease resistance to Xanthomonas oryzae pv. oryzae," Mol Plant Pathol, 10(6):829-835, 2009.
Guan et al., "Heritable endogenous gene regulation in plants with designed polydactyl zinc finger transcription factors," Proc Natl Acad Sci USA, 99(20):13296-13301, 2002.
Gürlebeck et al., "Dimerization of the bacterial effector protein AvrBs3 in the plant cell cytoplasm prior to nuclear import," Plant J, 42:175-187, 2005.
Gürlebeck et al., "Type III effector proteins from the plant pathogen Xanthomonas and their role in the interaction with the host plant," J Plant Physiol, 163(3):233-255, 2006 (Epub 2005).
Gürlebeck et al., "Visualization of novel virulence activities of the Xanthomonas type III effectors AvrBsl, AvrBs3, and AvrBs4," Mol Plant Pathol, 10(2):175-188, 2009.
Haber, "In vivo biochemistry: Physical monitoring of recombination induced by site-specific endonucleases," Bioessays, 17:609-620, 1995.
Haberlach et al., "Isolation, culture and regeneration of protoplasts from potato and several related *Solanum* species," *Plant Science,* 39:67-74 (1985).
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem Soc Trans, 39:584-588, 2011.
Handel et al., "Expanding or restricting the target site repertoire of zinc-finger nucleases: the inter-domain linker as a major determinant of target site selectivity," Mol Ther, 17:104-111, 2009.
Haun et al., "Improved soybean oil quality by targeted mutagenesis of fatty acid desaturase 2 gene family," *Plant Biotechnology Journal,* 1-7 (2014).
Herbers et al., "Race-specificity of plant resistance to bacterial spot disease determined by repetitive motifs in a bacterial avirulence protein," Nature, 356:172-174, 1992.
Heuer et al., "Repeat domain diversity of avrBs3-like genes in Ralstonia solanacearum strains and association with host preferences in the field," Appl Environ Microbiol, 73(13):4379-4384, 2007.
Hockemeyer et al., "Genetic engineering of human pluripotent cells using TALE nucleases," Nat Biotechnol, 29(8):731-734, 2011.

Hopkins et al., "Identification of a family of avirulence genes from Xanthomonas oryzae pv. oryzae," Mol Plant Microbe Interact, 5(6):451-459, 1992.
Hu et al., "A virulence gene and insertion element-based RFLP as well as RAPD markers reveal high levels of genomic polymorphism in the rice pathogen Xanthomonas oryzae pv. oryzae," Syst Appl Microbiol, 30:587-600, 2007.
Huang et al., "Heritable gene targeting in zebrafish using customized TALENs," Nat Biotechnol, 29(8):699-700, 2011.
Hummel et al., "Rice gene activation by transcription activator-like effectors of Xanthomonas oryzae pvs. oryzae and oryzicola," poster presentation, and "A cipher-like mechanism governs TAL effector-DNA recognition," poster #13-517, XIV International Congress on Molecular Plant-Microbe Interactions, Quebec City, Canada, 3 pages, Jul. 19-23, 2009.
Hurt et al., "Highly specific zinc finger proteins obtained by directed domain shuffling and cell-based selection," Proc Natl Acad Sci USA, 100(21):12271-12276, 2003.
Isalan et al., "A rapid, generally applicable method to engineer zinc fingers illustrated by targeting the HIV-1 promoter," Nat Biotechnol, 19(7):656-660, 2001.
Jackel et al., "Protein design by directed devolution," Annu Rev Biophys, 37:155-173, 2008.
Jones and Dangl, "The plant immune system," Nature, 444:323-329, 2006.
Jordan et al., "Physical delimitation of the pepper Bs3 resistance gene specifying recognition of the AvrBs3 protein from *Xanthomonas campestris* pv. vesicatoria," Theor Appl Genet, 113(5):895-905, 2006.
Kay and Bonas, "How Xanthomonas type III effectors manipulate the host plant," Curr Opin Microbiol, 12:37-43, 2009.
Kay et al., "A bacterial effector acts as a plant transcription factor and induces a cell size regulator," Science, 2007, 318:648-651.
Kay et al., "Bacterial Effector Acts as a Plant Transcription Factor and Induces a Cell Size Regulator," Science, 318(5850):648-651, 2007.
Kay et al., "Characterization of AvrBs3-like effectors from a Brassicaceae pathogen reveals virulence and avirulence activities and a protein with a novel repeat architecture," Mol Plant Microbe Interact, 18(8):838-848, 2005.
Kay et al., "Detailed analysis of the DNA recognition motifs of the Xanthomonas type III effectors AvrBs3 and AvrBs3deltarep16," Plant J, 59(6):859-871, 2009.
Keshavarzi et al., "Basal defenses induced in pepper by lipopolysaccharides are suppressed by *Xanthomonas campestris* pv. vesicatoria," Mol Plant Microbe Interact, 17(7):805-815, 2004.
Kim and Chandrasegaran, "Chimeric restriction endonuclease," Proc Natl Acad Sci USA, 91(3):883-887 (Feb. 1994).
Kim et al., "Comparative analysis of three indigenous plasmids from *Xanthomonas axonopodis* pv. glycines," Plasmid, 56(2):79-87, 2006.
Kim et al., "Construction of a Z-DNA-specific restriction endonuclease," Proc Natl Acad Sci USA, 94(24):12875-12879, 1997.
Kim et al., "Hybrid restriction enzymes: zinc finger fusions to FokI cleavage," Proc Natl Acad Sci USA, 93:1156-1160, 1996.
Kim et al., "Site-specific cleavage of DNA—RNA hybrids by zinc finger/FokI cleavage domain fusions," Gene, 203(1):43-49, 1997.
Kim et al., "Targeted genome editing in human cells with zinc finger nucleases constructed via modular assembly," *Genome Res,* 19:1279-1288 (2009).
Knoop et al., "Expression of avirulence gene avrBs3 from *Xanthomonas campestris* pv. vesicatoria is not under the control of hrp genes and is independent of plant factors," J Bacteriol, 173(22):7142-7150, 1991.
Lahaye and Bonas, "Molecular secrets of bacterial type III effector proteins," Trends Plant Sci, 6(10):479-485, 2001.
Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415.html>, 3 pages.
Lee et al., "Environmental Effects on Oleic Acid in Soybean Seed Oil of Plant Introductions with Elevated Oleic Concentration," *Crops Science,* Sep./Oct. 2009, 49:1762-1768.

(56) References Cited

OTHER PUBLICATIONS

Li et al., "Functional domains in FokI restriction endonuclease," Proc Natl Acad Sci USA, 89(10):4275-4279, 1992.
Li et al., "Modularly assembled designed TAL effector nucleases for targeted gene knockout and gene replacement in eukaryotes," Nucl Acids Res, 39:6315-6325, 2011.
Li et al., "TAL nucleases (TALNs): hybrid proteins composed of TAL effectors and FokI DNA-cleavage domain," Nucleic Acids Research, 39(1):359-372, 2010.
Liang et al., "Cloning and characterization of a novel avirulence gene (arp3) from *Xanthomonas oryzae* pv. oryzae," DNA Seq, 15(2):110-117, 2004.
Liu et al., "Design of polydactyl zinc-finger proteins for unique addressing within complex genomes," Proc Natl Acad Sci USA, 94(11):5525-5530, 1997.
Livak and Schmittgen, "Analysis of relative gene expression data using real-time quantitative PCR and the 2(-Delta C(T)) Method," *Method. Methods*, 25:402-408 (2001).
Mahfouz et al., "De novo-engineered transcription activator-like effector (TALE) hybrid nuclease with novel DNA binding specificity creates double-strand breaks," Proc Natl Acad Sci USA, 108:2623-2628, 2011.
Mahfouz et al., "TALE nucleases and next generation GM crops," *GM Crops*, Apr. 2011, 2(2):99-103.
Mak, "Sequence-specific DNA-binding TALEs," Nat Biotechnol, 29:43, 2011.
Marois et al., "The xanthomonas type III effector protein AvrBs3 modulates plant gene expression and induces cell hypertrophy in the susceptible host," Mol Plant Microbe Interact, 15(7):637-646, 2002.
Miller et al., "A TALE nuclease architecture for efficient genome editing," Nat Biotechnol, 29:143-148, 2011.
Miller et al., "An improved zinc-finger nuclease architecture for highly specific genome editing," Nature Biotechnol, 25:778-785, 2007.
Minczuk et al., "Development of a single-chain, quasi-dimeric zinc-finger nuclease for the selective degradation of mutated human mitochondrial DNA," Nucleic Acids Res, 36(12):3926-3938, 2008.
Mino et al., "Efficient double-stranded DNA cleavage by artificial zinc-finger nucleases composed of one zinc-finger protein and a single-chain FokI dimer," J Biotechnol, 140(3-4):156-161, 2009.
Moore et al., "Transactivated and chemically inducible gene expression in plants," Plant J, 45:651-683, 2006.
Morbitzer et al., "Assembly of custom TALE-type DNA binding domains by modular cloning," Nucleic Acids Research, 39(13):5790-5799, 2011.
Morbitzer et al., "Regulation of selected genome loci using de novo-engineered transcription activator-like effector (TALE)-type transcription factors," Proc Natl Acad Sci U S A., 107(50):21617-21622, 2010.
Moscou and Bogdanove, "A Simple Cipher Governs DNA Recognition by TAL Effectors," Science 326(5959): 1501, 2009.
Murakami et al., "The repeat domain of the type III effector protein PthA shows a TPR-like structure and undergoes conformational changes upon DNA interaction," Proteins, 78:3386-3395, 2010.
Murray et al., "Rapid isolation of high molecular weight plant DNA," *Nucl. Acids Res*, 8(19):4321-4325 (1980).
Mussolino et al., "A novel TALE nuclease scaffold enables high genome editing activity in combination with low toxicity," *Nucleic Acids Research*, 2011, 39:9283-9293.
Nakagawa et al., "Development of series of gateway binary vectors, pGWBs, for realizing efficient construction of fusion genes for plant transformation," J Biosci Bioeng, 104:34-41, 2007.
Niño-Liu et al., "Xanthomonas oryzae pathovars: model pathogens of a model crop," Mol Plant Pathol, 7(5):303-324, 2006.
Nissan et al. "The type III effectors HsvG and HsvB of gall-forming Pantoea agglomerans determine host specificity and function as transcriptional activators." Molecular Microbiology, 61(5): 1118-1131, 2006.
Noël et al., "XopC and XopJ, two novel type III effector proteins from *Xanthomonas campestris* pv. vesicatoria," J Bacteriol, 185(24):7092-7102, 2003.
Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/article8_article_3_1.phtml.
Padidam, "Chemically regulated gene expression in plants," Curr Opin Plant Biol, 6:169-177, 2003.
Paques and Duchateau, "Meganucleases and DNA Double-Strand Break-Induced recombination: Perspectives for Gene Therapy," Curr Gene Ther, 7:49-66, 2007.
Park et al., "Avirulence gene diversity of *Xanthomonas axonopodis* pv. Glycines isolated in Korea," J Microbiol Biotechnol, 18(9):1500-1509, 2008.
Pattanayak et al., "Revealing off-target cleavage specificities of zinc-finger nucleases by in vitro selection," Nat Methods, 8:765-770, 2011.
Paulus et al., "Silencing β1,2-xylosyltransferase in transgenic tomato fruits reveals xylose as constitutive component of IgE-binding epitopes," *Frontiers in Plant Science*, Aug. 2011, 2(4):12 pages.
Pavletich and Pabo, "Zinc finger-DNA recognition: crystal structure of a Zif268-DNA complex at 2.1 A," Science, 252:809-817, 1991.
Pearson, "The fate of fingers," Nature, 455:160-164, 2008.
Pennisi, "The Tale of the TALES," Science, 338(6113):1408-1411, 2012.
Pham et al., "Mutant alleles of FAD2-1A and FAD2-1B combine to produce soybeans with the high oleic acid seed oil trait," *BMC Plant Biology*, 2010, 10:195, 13 pages.
Pingoud and Silva, "Precision genome surgery," Nature Biotechnol, 25(7):743-744, 2007.
Podhajska and Szybalski, "Conversion of the FokI endonuclease to a universal restriction enzyme: cleavage of phage M13mp7 DNA at predetermined sites," Gene, 40(2-3):175-182, 1985.
Pomerantz et al., "Structure-based design of transcription factors," Science, 267(5194):93-96, 1995.
Porteus and Baltimore, "Chimeric nucleases stimulate gene targeting in human cells," *Science*, 300:763, 2003.
Porteus and Carroll, "Gene targeting using zinc finger nucleases," Nature Biotechnol, 23:967-973, 2005.
Porteus, "Zinc fingers on target," Nature, 459: 337-338, 2009.
Poienza et al., "Targeting transgene expression in research, agricultural, and environmental applications: Promoters used in plant transformation," In vitro Cell Dev Biol, 40(1):1-22, 2004.
Puchta et al., "Homologous recombination in plant cells is enhanced by in vivo induction of double strand breaks into DNA by a site-specific endonuclease," Nucl Acids Res, 21(22):5034-5040, 1993.
Radecke et al., "Zinc-finger nuclease-induced gene repair with oligodeoxynucleotides: wanted and unwanted target locus modifications," Mol Ther, 18(4):743-753, 2010.
Reyon et al., "FLASH assembly of TALENs for high-throughput genome editing," Nat Biotechnol, 2012, 30:460-465.
Römer et al., "A single plant resistance gene promoter engineered to recognize multiple TAL effectors from disparate pathogens," *Proc Natl Acad Sci USA*, 106(48):20526-31, 2009.
Römer et al., "Plant pathogen recognition mediated by promoter activation of the pepper Bs3 resistance gene," *Science*, 2007, 318:645-648.
Römer et al., "Promoter elements of rice susceptibility genes are bound and activated by specific TAL effectors from the bacterial blight pathogen, Xanthomonas oryzae pv. oryzae," New Phytol, 187:1048-1057, 2010.
Römer et al., "Recognition of AvrBs3-Like Proteins Is Mediated by Specific Binding to Promoters of Matching Pepper Bs3 Alleles," Plant Physiol, 150:1697-1712, 2009.
Romero et al., "Temperature Sensitivity of the Hypersensitive Response of Bell Pepper to *Xanthomonas axonopodis* pv. vesicatoria," Phytopathology, 92(2):197-203, 2002.
Rossier et al., "HrpB2 and HrpF from Xanthomonas are type III-secreted proteins and essential for pathogenicity and recognition by the host plant," Mol Microbiol, 38(4):828-838, 2000.

(56) References Cited

OTHER PUBLICATIONS

Rossier et al., "The Xanthomonas Hrp type III system secretes proteins from plant and mammalian bacterial pathogens," Proc Natl Acad Sci USA, 96(16):9368-9373, 1999.
Rouet et al., "Expression of a site-specific endonuclease stimulates homologous recombination in mammalian cells," Proc Natl Acad Sci USA, 91(13):6064-6068, 1994.
Rouet et al., "Introduction of double-strand breaks into the genome of mouse cells by expression of a rare-cutting endonuclease," Mol Cell Biol, 14(12):8096-8106, 1994.
Rybak et al., "Identification of *Xanthomonas citri* ssp. citri host specificity genes in a heterologous expression host," Mol Plant Pathol, 10(2):249-262, 2009.
Sandhu et al., "Enhanced oleic acid content in the soybean mutant M23 is associated with the deletion in the Fad2-1a gene encoding a fatty acid desaturase," JAOCS, 84:229-235 (2007).
Santiago et al., "Targeted gene knockout nucleases," Proc Natl Acad Sci USA, in mammalian cells by using engineered zinc-finger 105(15):5809-5814, 2008.
Scholze and Boch, "TAL effectors are remote controls for gene activation," Curr Opin Microbiol, 14:47-53, 2011.
Scholze and Boch. "TAL effector-DNA specificity," Virulence, 1(5):428-432, 2010.
Schornack et al., "Characterization of AvrHah1, a novel AvrBs3-like effector from Xanthomonas gardneri with virulence and avirulence activity," New Phytol, 179:546-556, 2008.
Schornack et al., "Expression levels of avrBs3-like genes affect recognition specificity in tomato Bs4- but not in pepper BS3-mediated perception," Mol Plant-Microbe Interact, 18(11):1215-1225, 2005.
Schornack et al., "Gene-for-gene-mediated recognition of nuclear-targeted AvrBs3-like bacterial effector proteins," *J Plant Physiol*, 2006, 163:256-272.
Schornack et al., "The tomato resistance protein Bs4 is a predicted non-nuclear TIR-NB-LRR protein that mediates defense responses to severely truncated derivatives of AvrBs4 and overexpressed AvrBs3," Plant J, 37(1):46-60, 2004.
Segal et al., "Endonuclease-induced, targeted homologous extrachromosomal recombination in Xenopus oocytes," Proc Natl Acad Sci USA, 92(3):806-810, 1995.
Sera, "Inhibition of virus DNA replication by artificial zinc finger proteins," J Virol, 79(4):2614-2619, 2005.
Shepard and Totten, "Mesophyll cell protoplasts of potato: isolation, proliferation, and plant regeneration," *Plant Physiol.*, 60:313-316(1977).
Shukla et al., "Precise genome modification in the crop species *Zea mays* using zinc-finger nucleases," Nature, 459(7245):437-441, 2009.
Simon et al., "Targeting DNA with triplex-forming oligonucleotides to modify gene sequence," Biochimie, 90:1109-1116, 2008.
Skipper, "Technology: The holy grail for plant biologists," Nature Reviews Genetics, 10(6):350, 2009.
Studholme et al., "Genome-wide sequencing data reveals virulence factors implicated in banana Xanthomonas wilt," FEMS Microbiol Lett., 310(2):182-192, 2010.
Sugio et al., "Two type III effector genes of *Xanthomonas oryzae* pv. oryzae control the induction of the host genes OsTFIIAgamma1 and of OsTFX1 during bacterial blight of rice," *Proc Nat Acad Sci USA*, 2007, 104:10720-10725.
Swarup et al., "An Xanthomonas citri pathogenicity gene, pthA, pleiotropically encodes gratuitous avirulence on nonhosts," Mol Plant Microbe Interact, 5(3):204-213, 1992.
Szurek et al. "Type III-dependent translocation of the Xanthomonas AvrBs3 protein into the plant cell," Mol Microbiol, 46(1): 13-23, 2002.
Szurek et al., "Eukaryotic features of the Xanthomonas type III effector AvrBs3: protein domains involved in transcriptional activation and the interaction with nuclear import receptors from pepper," Plant J, 26(5):523-534, 2001.

Takenaka et al., "Inhibition of tomato yellow leaf curl virus replication by artificial zinc-finger proteins," Nucl Acids Symposium Series, 51(1):429-430, 2007.
Thieme et al., "New type III effectors from *Xanthomonas campestris* pv. vesicatoria trigger plant reactions dependent on a conserved N-myristoylation motif," Mol Plant Microbe Interact, 20(10):1250-1261, 2007.
Thierry et al., "Cleavage of yeast and bacteriophage T7 genomes at a single site using the rare cutter endonuclease I-Sce I," Nucl Acids Res, 19(1):189-190, 1991.
Tovkach et al., "A toolbox and procedural notes for characterizing novel zinc finger nucleases for genome editing in plant cells," Plant J, 57:747-757, 2009.
Townsend et al., "High-frequency modification of plant genes using engineered zinc-finger nucleases," Nature, 459:442-445, 2009.
Urnov et al., "Highly efficient endogenous human gene correction using designed zinc-finger nuclease," Nature, 435(7042):646-651, 2005.
Van Den Ackerveken et al., "Recognition of the bacterial avirulence protein AvrBs3 occurs inside the host plant cell," Cell, 87(7):1307-1316, 1996.
Van Den Elzen et al., "A chimaeric hygromycin resistance gene as a selectable marker in plant cells," *Plant Molecular Biology*, 1985, 5:299-302.
Vergunst et al., "VirB/D4-Dependent Protein Translocation from Agrobacterium into Plant Cells," Science, 290:979-982, 2000.
Voytas et al., "Plant science. DNA binding made easy," Science, 326(5959):1491-1492, 2009.
Wah et al., "Structure of FokI has implications for DNA cleavage," Proc Natl Acad Sci USA, 95(18):10564-10569, 1998.
Wah et al., "Structure of the multimodular endonuclease FokI bound to DNA," Nature, 388(3):97-100, 1997.
Wang et al., "Chemically regulated expression systems and their applications in transgenic plants," Transgenic Res, 12:529-540, 2003.
Weber et al., "The type III-dependent Hrp pilus is required for productive interaction of *Xanthomonas campestris* pv. vesicatoria with pepper host plants," J Bacteriol, 187(7):2458-2468, 2005.
White and Yang, "Host and pathogen factors controlling the rice/Xanthomonas oryzae interaction," Plant Physiol, 150:1677-1686, 2009.
White et al., "The type III effectors of Xanthomonas," Mol Plant Pathol, 10:749-766, 2009.
Wright et al., "High-frequency homologous recombination in plants mediated by zinc-finger nucleases," Plant J, 2005, 44:693-705.
Yang and White, "Diverse members of the AvrBs3/PthA family of type III effectors are major virulence determinants in bacterial blight disease of rice," Mol Plant Microbe Interact, 17(11):1192-1200, 2004.
Yang et al. "The virulence factor AvrXa7 of Xanthomonas oryzae of Oryzae is a type III secretion pathway-dependent nuclear-localized double stranded DNA binding protein," Proc Natl Acad Sci USA, 97(17): 9807-9812, 2000.
Yang et al., "Avoidance of host recognition by alterations in the repetitive and C-terminal regions of AvrXa7, a type III effector of *Xanthomonas oryzae* pv. oryzae," Mol Plant Microbe Interact, 18(2):142-149, 2005.
Yang et al., "Os8N3 is a host disease-susceptibility gene for bacterial blight of rice," *Proc Nat Acad Sci USA*, 2006, 103:10503-10508.
Yoo et al., "Arabidopsis mesophyll protoplasts: a versatile cell system for transient gene expression analysis," *Nature Protocols*, 2007, 2:1565-1572.
Yuan et al., "Characterization of Xanthomonas olyzae-responsive cis-acting element in the promoter of rice race-specific susceptibility gene Xa13," Mol Plant, 4(2):300-309, 2011.
Zhang et al., "Efficient construction of sequence-specific TAL effectors for modulating mammalian transcription," *Nat Biotechnol*, 2011, 29:149-153.
Zhang et al., "High frequency targeted mutagenesis in *Arabidopsis thaliana* using zinc finger nucleases," *Proc Natl Acad Sci USA*, 107(26):12028-12033 (2010).

(56) References Cited

OTHER PUBLICATIONS

Zhang et al., "RNAi effects on regulation of endogenous acid invertase activity in potato (*Solanum tuberosum* L.) tubers," *Chin J Agric. Biotechnol*, 5:107-111 (2008).
Zhu et al., "The C terminus of AvrXa10 can be replaced by the transcriptional activation domain of VP16 from the herpes simplex virus," Plant Cell, 11(9):1665-1674, 1999.
Zhu et al., "AvrXa10 Contains an Acidic Transcriptional Activation Domain in the Functionally Conserved C Terminus," Molecular Plant-Microbe Interactions, 11(8): 824-832, 1998.
Zhu et al., "The rsma-like gene rsmA(XOO) of *Xanthomonas oryzae* pv. oryzae regulates bacterial virulence and production of diffusible signal factor," Mol Plant Pathol, 12(3):227-237, 2011, Epub 2010.
Zou et al., "Identification of an avirulence gene, avrxa5, from the rice pathogen *Xanthomonas oryzae* pv. oryzae," Sci China Life Sci, 53(12):1440-1449, 2010.
Zrenner et al., "Soluble acid invertase determines the hexose-to sucrose ratio in cold-stored potato tubers," *Planta*, 198(2):246-252 (1996).
Zuo and Chua, "Chemical-inducible systems for regulated expression of plant genes," Curr Opin Biotechnol, 11:146-151, 2000.
Zuo et al., "Technical advance: An estrogen receptor-based transactivator XVE mediates highly inducible gene expression in transgenic plants," *Plant J.* 24:265-273 (2000).
International Preliminary Report on Patentability in International Application No. PCT/US2013/067810, dated May 14, 2015, 10 pages.
GenBank Accession No. EF562628.1, "Nicotiana benthamiana xylosyltransferase 1 mRNA, complete cds," dated Jan. 1, 2008, retrieved on Feb. 23, 2017, https://www.ncbi.nlm.nih.gov/nuccore/156103419?sat=14&satkey=2811708, 2 pages.
GenBank Accession No. EF562629.1, "Nicotiana benthamiana xylosyltransferase 2 mRNA, complete cds," dated Jan. 1, 2008, retrieved on Feb. 23, 2017, https://www.ncbi.nlm.nih.gov/nuccore/156103421?sat=4&satkey=19996217, 2 pages.
GenBank Accession No. EF562630.1, "Nicotiana benthamiana fucosyltransferase 1 mRNA, complete cds," dated Jan. 1, 2008, retrieved on Feb. 23, 2017, https://www.ncbi.nlm.nih.gov/nuccore/156103423?sat=14&satkey=3146897, 2 pages.
GenBank Accession No. EF562631.1, "Nicotiana benthamiana fucosyltransferase pseudogene mRNA, complete sequence," dated Jan. 1, 2008, retrieved on Feb. 23, 2017, https://www.ncbi.nlm.nih.gov/nuccore/156103425?sat=14&satkey=3146898, 2 pages.
Tzfira et al., "Genome modifications in plant cells by custom-made restriction enzymes," Plant Biotechnol J., 10(4):373-389, May 2012.
Li et al., "Multiplexed, targeted gene editing in *Nicotiana benthamiana* for glyco-engineering and monoclonal antibody production," Plant Biotechnology Journal, 1-10, 2015, with Supplemental Information.
Strasser et al., "Generation of *Arabidopsis thaliana* plants with complex N-glycans lacking beta1,2-linked xylose and core alpha1,3-linked fucose," *FEBS Lett.*, 561(1-3):132-6, Mar. 2004.
Chrispeels, M., et al. The Production of Recombinant Glycoproteins with defined Non-Immunogenic Glycans. Transgenic Plants: A Production System for Industrial and Pharmaceutical Proteins. pp. 99-113, John Wiley, Chichester, UK, 1996.
GDP-4-dehydro-6-deoxy-D-mannose reductase. From Wikipedia.
von Horsten, Hans Henning, et al. Production of non-fucosylated antibodies by co-expression of heterologous DGP-6-deoxy-D-lyxo-4-hexulose reductase. Glycobiology vol. 20:12, 1607-1618, 2010.
King, Jerry D., et al. The structural basis for catalytic function of GMD and RMD, two closely related enzymes from the GDP-D-rhamnose biosynthesis pathway. FEBS Journal 276 (2009) pp. 2686-2700.
Loos, Andreas et al. Plant glyco-biotechnology on the way to synthetic biology. Frontiers in Plant Science, 2014. vol. 5:523, pp. 1-10.
Matsuo, Kouki, et al. Deletion of paint-specific sugar residues in plant N-glycans by repression of GDP-D-mannose 4,6-dehydrtase and Beta-1,2-xylosyltransferase genes. Journal of Bioscience and Bioengineering, vol. 118:4, pp. 448-454, 2014.
Matsuo, Kouki, et al. Deletion of fucose residues in plant N-glycans by repression of the GDP-mannose 4,6-dehydratase gene using virus-induced gene silencing and RNA interference. Plant Biotechnology Journal. 2011, vol. 9, pp. 264-281.
Palmberger, D. et al. Minimizing fucosylation in insect cell-derived glycoproteins reduces binding to IgE antibodies from the sera of patients with allergy. (Biotechnol J. Sep. 2014; 9(9): 1206-1214.).
Bogdanove, Adam J., et al. TAL Effectors: Customizable Proteins for DNA Targeting. Science 333, 1843-1846 (2011).
Cermak Tomas, et al. Efficient design and assembly of custom TALEN and other TAL effector-based constructs for DNA targeting. Nucleic Acids Research, vol. 39:12, 2011. pp. 1-11.
Li, Ting, et al. High-efficiecy TALEN based gene editing produces disease-resistant rice. Nature Biotechnology, vol. 30:5, 2012, pp. 390-392.
Mahfouz, Mandy M., et al. TALE nucleases and next generation GM crops. GM Crops vol. 2:2, pp. 99-103, 2011.
Strasser et al., "Generation of glycol-engineered Nicotiana benthamiana for the production of monoclonal antibodies with a homogeneous human-like N-glycan structure," *Plant Biotechnology Journal*, vol. 6, Issue: 4, pp. 392-402 (2008).

\* cited by examiner

XyI_T01
ATGAACAAGAAAAAGCTGAAAATTCTTGTTTCTCTCTTCGCTCTCAACTCAATCACTCTCTATCTCTACTTCTCTTCCCA
CCCTGATCAC (SEQ ID NO:1)

XyI_T02
ATGAACAAGAAAAAGCTGAAAATTCTTGTTTCTCTCTTCGCTCTCAACTCAATCACTCTCTATCTCTACTTCTCTTCCCA
CCCTGATCAC (SEQ ID NO:1)

XyI_T03
ATGAACAAGAAAAAGCTGAAAATTCTTGTTTCTCTCTTCGCTCTCAACTCAATCACTCTCTATCTCTACTTCTCTTCCCA
CCCTGATCAC (SEQ ID NO:1)

XyI_T04
ATGAACAAGAAAAAGCTGAAAATTCTTGTTTCTCTCTTCGCTCTCAACTCAATCACTCTCTATCTCTACTTCTCTTCCCA
CCCTGATCAC (SEQ ID NO:1)

Figure 1

FucT1_T01
ATGAGATCGGCGTCAAATTCAAACGCACCCAATAAGCAATGGGCGCAATTGGTTGCCTCTCTGTTCGTTGCCCTAGTGATTATAGCTGA
GTTTCTTTTCTGACTCGACGTAGCTGAAAAAGCCAACT (SEQ ID NO:2)

FucT2_T01
ATGAGATCGTGTCAAATTCAAACGCACCCGATAAACAATGGGCGCAATTGGTTGCCTCTCTGTTCGTTGCCCTAGTTGTTATAGCAGA
AATTTCTTTTCTGGTTCGACTCGACGTGGCTGAAAAAGCCAACT (SEQ ID NO:3)

FucT1_T02
ATGAGATCGGCGTCAAATTCAAACGCACCCAATAAGCAATGGGCGCAATTGGTTGCCTCTCTGTTCGTTGCCCTAGTGATTATAGCTGA
GTTTCTTTTCTGACTCGACTCGACGTAGCTGAAAAAGCCAACT (SEQ ID NO:2)

FucT2_T02
ATGAGATCGTGTCGTCAAATTCAAACGCACCCGATAAACAATGGGCGCAATTGGTTGCCTCTCTGTTCGTTGCCCTAGTTGTTATAGCAGA
AATTTCTTTTCTGGTTCGACTCGACGTGGCTGAAAAAGCCAACT (SEQ ID NO:3)

FucT1_T03
ATGAGATCGGCGTCAAATTCAAACGCACCCAATAAGCAATGGGCGCAATTGGTTGCCTCTCTGTTCGTTGCCCTAGTGATTATAGCTGA
GTTTCTTTTCTGACTCGACTCGACGTAGCTGAAAAAGCCAACT (SEQ ID NO:2)

FucT2_T03
ATGAGATCGTGTCGTCAAATTCAAACGCACCCGATAAACAATGGGCGCAATTGGTTGCCTCTCTGTTCGTTGCCCTAGTTGTTATAGCAGA
AATTTCTTTTCTGGTTCGACTCGACGTGGCTGAAAAAGCCAACT (SEQ ID NO:3)

FucT1_T04
ATGAGATCGGCGTCAAATTCAAACGCACCCAATAAGCAATGGGCGCAATTGGTTGCCTCTCTGTTCGTTGCCCTAGTGATTATAGCTGA
GTTTCTTTTCTGACTCGACTCGACGTAGCTGAAAAAGCCAACT (SEQ ID NO:2)

FucT2_T04
ATGAGATCGTCGTCAAATTCAAACGCACCCGATAAACAATGGGCGCAATTGGTTGCCTCTCTGTTCGTTGCCCTAGTTGTTATAGCAGA
AATTTCTTTTCTGGTTCGACTCGACGTGGCTGAAAAAGCCAACT (SEQ ID NO:3)

Figure 2

Xylosyltransferase 1

```
                                                                Deletion Size  SEQ ID NO:
gtttcTCTTCTTCGCTCTCAACTcaatcactctctatCTCTACTTCTCTTCCCAccctg    Wild-Type      4
gtttctctctcttcgctctcaactcaa----tctctatctctactctctctctccaccctg  4 bp           5
gtttctctctcttcgctctcaactca------tctatctctactctctctctctccaccctg 7 bp           6
gtttctctctcttcgctctca--------actctctatctctactctctctctctccaccctg 8 bp          7
gtttctctctcttcgctctcaactca----------atctctactctctctctctccaccctg 10 bp         8
gtttctctctcttcgctctcaactc---------------ctactctctctctctccaccctg 15 bp         9
gtttctctctcttcgctctcaa-----------------tctctactctctctctccaccctg 17 bp        10
gtttctc-----------------------ctctatctctactctctctctctccaccctg   23 bp        11
gt----------------------------tctctatctctactctctctctccaccctg    27 bp        12
gtttctctcttcg---------------------------------------cacccctg    38 bp        13
gtttctctcttcgct------------------------------------------ctg    40 bp        14
```

Xylosyltransferase 2

```
                                                                Deletion Size  SEQ ID NO:
gtttcTCTTCTTCGCTCTCAACTcaatcactctctatCTCTACTTCTCTTCCCAccctg    Wild-Type      4
gtttctctctcttcgctctcaactca--------tctatctctactctctctctctccaccctg 7 bp         6
gtttctctctcttcgctctcaactca--------actctctatctctactctctctctccaccctg 8 bp      7
gtttctctctcttcgctctca--------tgtctctatctctactctctctctctccaccctg 10 bp       15
gtttctctctcttcgctctctc-----------ctctctatctctactctctctctccaccctg 12 bp      16
gtttctctctcttcgctctcg-------------ctatctctactctctctctctccaccctg 15 bp       17
gtttctctctcttcgctctc----------------ctctatctctactctctctccaccctg 20 bp       18
gtttctctctcttcg----------------------------tctcttctctcccaccctg 29 bp        19
g--------------------------------atctctactctctctctccaccctg      33 bp       20
gtttctctcttcgc------------------------tctatctctactctctctccaccctg 35 bp     21
gt-------------------------------------------ttctcttcccaccctg    40 bp      22
```

Figure 3

Fucosyltransferase 1

```
                                                         Deletion Size  SEQ ID NO:
tcaaaTTCAAACGCACCCAATAagcaattggtgcgcaattggttgcCTCTGTTCGTTGCCCTAgtgat  Wild-Type      23
tcaaattcaaacgcacccaataagcaatggcgc----ggttgcctctgttcgttgccctagtgat         4 bp        24
tcaaattcaaacgcacccaataagcaa-------------tgcctctgttcgttgccctagtgat        13 bp        25
tcaaattcaaacgcacccaataagcaat-----------cctctgttcgttgccctagtgat           14 bp        26
tcaaattcaaacgcacccaa-------------------ttgcctctgttcgttgccctagtgat        19 bp        27
tcaaattcaaacgcacccaataa----------------------ctgttcgttgccctagtgat        22 bp        28
tcaaattcaaacgcacccaataa--------------------------gttcgttgccctagtgat      24 bp        29
tcaaattcaaacgcacccaataagca---------------------------ttgccctagtgat       26 bp        30
tcaaattcaaacgcacccaa---------------------------------tcgttgccctagtgat    29 bp        31
tcaaattcaaacgcacc-----------------------------------------gccctagtgat    37 bp        32
tcaaattcaaacgcacccaata-----------------------------------------gtgat    44 bp        33
```

Fucosyltransferase 2

```
                                                         Deletion Size  SEQ ID NO:
tcaaaTTCAAACGCCACCCGATAaacaatggcgcaattggttgcCTCTGTTCGTTGCCCTAgttgt   Wild-Type      34
tcaaattcaaacgcacccgatcaacaatggc-------gttgcctctgttcgttgccctagttgt         7 bp        35
tcaaattcaaacgcacccgataaaacaaca-----------ggttgcctctgttcgttgccctagttgt    11 bp        36
tcaaattcaaacgcacccgataaaaca--------------ttggttgcctctgttcgttgccctagttgt  14 bp        37
tcaaattcaaacgcacccgat------------------cctctgttcgttgccctagttgt           18 bp        38
tcaaattcaaacgcacccgataaa-----------------ctctgttcgttgccctagttgt          20 bp        39
tcaaattcaaacgcacccgataa------------------tctgttcgttgccctagttgt           23 bp        40
tcaaattcaaacgcacccgat-----------------------ttgcctctgttcgttgccctagttgt   24 bp        41
tcaaattcaaacgcacccgataaacaa---------------------tgcctctgttcgttgccctagttgt 26 bp      42
tcaaattcaaacgcacccgataaac-----------------------gccctagttgt              29 bp        43
tcaaattcaaacgcca--------------------------------cccctagttgt              40 bp        44
```

Figure 4

FucT1 allele (13-bp deletion) in NB13-105a:
ATGAGATCGGCGTCAAATTCAAACGCACCCAATAAGCAATGGGCGCAATTGGTTGCCTCTGTTCGTTGCCCTAGTGATTATAG (SEQ ID NO:80)
||||||||||||||||||||||||||||||||||||||||||||||              |||||||||||||||||||||
ATGAGATCGGCGTCAAATTCAAACGCACCCAATAAGCA-------------TTGCCTCTGTTCGTTGCCCTAGTGATTATAG (SEQ ID NO:81)

FucT2 allele (14-bp deletion) in NB13-105a:
ATGAGATCGTCGTCAAATTCAAACGCACCCGATAAACAATGGGCGCAATTGGTTGCCTCTGTTCGTTGCCCTAGTTGTTATAG (SEQ ID NO:82)
|||||||||||||||||||||||||||||||||||||                    |||||||||||||||||||||||
ATGAGATCGTCGTCAAATTCAAACGCACCCGATAAGC--------------TTGCCTCTGTTCGTTGCCCTAGTTGTTATAG (SEQ ID NO:83)

FucT1 alleles (20-bp and 12-bp deletions) in NB13-213a:
ATGAGATCGGCGTCAAATTCAAACGCACCCAATAAGCAATGGGCGCAATTGGTTGCCTCTGTTCGTTGCCCTAGTGATTATAG (SEQ ID NO:80)
|||||||||||||||||||||||||||||||||||                   |||||||||||||||||||||||||||
ATGAGATCGGCGTCAAATTCAAACGCACCCAAT--------------------GCCTCTGTTCGTTGCCCTAGTGATTATAG (SEQ ID NO:84)
ATGAGATCGGCGTCAAATTCAAACGCACCCAATAAGCAATGGGCGCAATTGGTTGCCTCTGTTCGTTGCCCTAGTGATTATAG (SEQ ID NO:80)
|||||||||||||||||||||||||||||||||||||||||             ||||||||||||||||||||||||||
ATGAGATCGGCGTCAAATTCAAACGCACCCAATAAGCAAT------------TGCCTCTGTTCGTTGCCCTAGTGATTATAG (SEQ ID NO:85)

FucT2 alleles (13-bp and 2-bp deletions) in NB13-213a:
ATGAGATCGTCGTCAAATTCAAACGCACCCGATAAACAATGGGCGCAATTGGTTGCCTCTGTTCGTTGCCCTAGTTGTTATAG (SEQ ID NO:82)
||||||||||||||||||||||||||||||||||||||||                |||||||||||||||||||||||||
ATGAGATCGTCGTCAAATTCAAACGCACCCGATAAACAATG-------------CCTCTGTTCGTTGCCCTAGTTGTTATAG (SEQ ID NO:86)
ATGAGATCGTCGTCAAATTCAAACGCACCCGATAAACAATGGGCGCAATTGGTTGCCTCTGTTCGTTGCCCTAGTTGTTATAG (SEQ ID NO:82)
||||||||||||||||||||||||||||||||||||||||||  |||||||||||||||||||||||||||||||||||||
ATGAGATCGTCGTCAAATTCAAACGCACCCGATAAACAATGGGCA--TGTTGCCTCTGTTCGTTGCCCTAGTTGTTATAAG (SEQ ID NO:87)

Figure 5

XylT1 alleles (two 7-bp deletions) in NB15-11d:
ATGAACAAGAAAAAGCTGAAAATTCTTGTTTCTCTCTTCGCTCTCAACTCAATCACTCTCTATCTCTACTTCTCTTCCACC (SEQ ID NO:88)
||||||||||||||||||||||||||||||||||||||||||||||||||||   |||   |||||||||||||||||||
ATGAACAAGAAAAAGCTGAAAATTCTTGTTTCTCTCTTCGCTCTCAACT--ATC----CTATCTCTACTTCTCTTCCACC (SEQ ID NO:89)
||||||||||||||||||||||||||||||||||||||||||||||||||||||||||||||||||||||||||||||||
ATGAACAAGAAAAAGCTGAAAATTCTTGTTTCTCTCTTCGCTCTCAACTCAATCACTCTCTATCTCTACTTCTCTTCCACC (SEQ ID NO:88)
|||||||||||||||||||||||||||||||||||||||||||||||||||||       ||||||||||||||||||||
ATGAACAAGAAAAAGCTGAAAATTCTTGTTTCTCTCTTCGCTCTCAACTCAA-------CTATCTCTACTTCTCTTCCACC (SEQ ID NO:90)

XylT2 allele (8-bp deletion) in NB15-11d:
ATGAACAAGAAAAAGCTGAAAATTCTTGTTTCTCTCTTCGCTCTCAACTCAATCACTCTCTATCTCTACTTCTCTTCCACC (SEQ ID NO:88)
||||||||||||||||||||||||||||||||||||||||||||||||||||||||||        ||||||||||||||
ATGAACAAGAAAAAGCTGAAAATTCTTGTTTCTCTCTTCGCTCTCAACTC--------TCTATCTCTACTTCTCTTCCACC (SEQ ID NO:91)

XylT1 allele (7-bp deletion) in NB12-113c:
ATGAACAAGAAAAAGCTGAAAATTCTTGTTTCTCTCTTCGCTCTCAACTCAATCACTCTCTATCTCTACTTCTCTTCCACC (SEQ ID NO:88)
||||||||||||||||||||||||||||||||||||||||||||||||||||||||||||       |||||||||||||
ATGAACAAGAAAAAGCTGAAAATTCTTGTTTCTCTCTTCGCTCTCAACTCAATCT-------TCTCTACTTCTCTTCCACC (SEQ ID NO:92)

XylT2 alleles (35-bp and 5-bp deletions) in NB12-113c:
ATGAACAAGAAAAAGCTGAAAATTCTTGTTTCTCTCTTCGCTCTCAACTCAATCACTCTCTATCTCTACTTCTCTTCCACC (SEQ ID NO:88)
||||||||||||||||||||||||||                                   |||||||||||||||||||
ATGAACAAGAAAAAGCTGAAAATTCT-----------------------------------ATCTCTACTTCTCTTCCACC (SEQ ID NO:93)
||||||||||||||||||||||||||||||||||||||||||||||||||||     |||||||||||||||||||||||
ATGAACAAGAAAAAGCTGAAAATTCTTGTTTCTCTCTTCGCTCTCAACTCAAT-----TCTATCTCTACTTCTCTTCCACC (SEQ ID NO:94)

Figure 6

FucT1 alleles (identical 44-bp deletions) in NB14-29a:
ATGAGATCGGCGTCAAATTCAAACGCACCAATAAGCAATTGGTTGCCTCTGTTCGTTGCCCTAGTGATTATAG (SEQ ID NO:80)
||||||||||||||||||||||||||||||||                                ||||||||
ATGAGATCGGCGTCAAATTCAAACGCACCCA---------------------------------ATTATAG (SEQ ID NO:95)

FucT2 alleles (2-bp and 40-bp deletions) in NB14-29a:
ATGAGATCGTCGTCAAATTCAAACGCACCCGATAAACAATGGGCAATTGGTTGCCTCTGTTCGTTGCCCTAGTTGTTATAG (SEQ ID NO:82)
|||||||||||||||||||||||||||||||||||||||||||| |||||||||||||||||||||||||||||||||||
ATGAGATCGTCGTCAAATTCAAACGCACCCGATAAACAATGGGCGC-TTGGTTGCCTCTGTTCGTTGCCCTAGTTGTTATAGG (SEQ ID NO:96)

ATGAGATCGTCGTCAAATTCAAACGCACCCGATAAACAATGGGCAATTGGTTGCCTCTGTTCGTTGCCCTAGTTGTTATAG (SEQ ID NO:82)
||||||||||||||||||||||||||||||||||||||||
ATGAGATCGTCGTCAAATTCAAACGCACCCGATAAACAATG---------------------------------------G (SEQ ID NO:97)

Figure 7

XylT1 alleles (identical 5-bp deletions) in NB14-29a:

```
ATGAACAAGAAAAAGCTGAAAATTCTTGTTTCTCTCTTCGCTCTCAACTCAATCACTCTCTATCTCTACTTCTCTTCCCACC (SEQ ID NO:88)
||||||||||||||||||||||||||||||||||||||||||||||||||||||     |||||||||||||||||||||||
ATGAACAAGAAAAAGCTGAAAATTCTTGTTTCTCTCTTCGCTCTCAACTCAATC-----CTATCTCTACTTCTCTTCCCACC (SEQ ID NO:98)
```

XylT2 alleles (6-bp and 549-bp deletions) in NB14-29a:

```
ATGAACAAGAAAAAGCTGAAAATTCTTGTTTCTCTCTTCGCTCTCAACTCAATCACTCTCTATCTCTACTTCTCTTCCCACC (SEQ ID NO:88)
||||||||||||||||||||||||||||||||||||||||||||||||||||||      ||||||||||||||||||||||
ATGAACAAGAAAAAGCTGAAAATTCTTGTTTCTCTCTTCGCTCTCAACTCAATC------TATCTCTACTTCTCTTCCCACC (SEQ ID NO:99)

AACAATAAGGATAATAACAACTCAATATAATTTTAATTAGTAGGATCTAGGAAGAATAATGTGTATATAAATCTTATTTCTG
|||||||||||||||||||||||||
AACAATAAGGATAATAACAACTCAA---------------------------------------------------------

TCATGGATAGAGAGGTTGTCCCGAAATAGAAAAATTTTATGCTTCAAATTTTGAAATAAAGTAATCTTTTTAAAAAAATACT
----------------------------------------------------------------------------------

ATATAAAGTGTAATTACAACTCAAATAATCATATTTAACTAACATCGTTAAACCCTCTGTACTAAGTAGTACAGACGAAAAC
----------------------------------------------------------------------------------

AGCCCGTGAGAGAGAGAGAGAGAGAGGAGAAGAAGATGAACAAGAAAAAGCTGAAAATTCTTGTTTCTCTCTTCGCTCTCAA
----------------------------------------------------------------------------------

CTCAATCACTCTCTATCTCTACTTCTCTTCCCACCCTGATCACTCTCGTCGCAAATCCCCCCAGAACCACTTTTCCTCGTCG
----------------------------------------------------------------------------------

GAAAACCACCATCATAATTTCCACTCTTCAATCACTTCCCAATATTCCAGGCCTTGGCCTATTTTGCCCTCCTACCTCCCTT
----------------------------------------------------------------------------------

GGTCTCAAAACCCTAATGTTGCTTGGAGATCATGCGAGGGTTACTTCGGTAATGGTTTTACTCTCAAAGTTGATCTTCTCAA
----------------------------------------------------------------------------------

AACTTCGCCGGAGCTTCACCGGAAATTCGGCGAAAACACCGTCTTCGGAGACGGCGGATGGTTTAGGTGTTTCTTCAGTGAG (SEQ ID NO:100)
||||||||||||||||||||||||||||||||||||||||||||||||||||||||||||||||||||||||||||||||||
AACTTCGCCGGAGCTTCACCGGAAATTCGGCGAAAACACCGTCTTCGGAGACGGCGGATGGTTTAGGTGTTTCTTCAGTGAG (SEQ ID NO:101)
```

METHOD FOR MAKING NICOTIANA PLANTS WITH MUTATIONS IN XYLT AND FUCT ALLELES USING RARE-CUTTING ENDONUCLEASES

CROSS-REFERENCE TO RELATED APPLICATIONS

This application is a National Stage application under 35 U.S.C. § 371 of International Application No. PCT/US2013/067810, having an International Filing Date of Oct. 31, 2013, which claims benefit of priority from U.S. Provisional Application Ser. No. 61/790,850, filed on Mar. 15, 2013, and U.S. Provisional Application Ser. No. 61/721,194, filed on Nov. 1, 2012.

TECHNICAL FIELD

This document relates to materials and methods for making plants that are suitable for production of therapeutic proteins for administration to humans and animals, particularly by making targeted knockouts in genes encoding xylosyltransferases and fucosyltransferases. This document also relates to Nicotiana varieties that lack xylosyltransferase and fucosyltransferase activity, or that have reduced xylosyltransferase and fucosyltransferase activity.

BACKGROUND

Unlike animal glycoproteins, plant glycoproteins have beta(1,2) xylosyl and core-alpha(1,3) fucosyl residues, and lack terminal beta(1,4) galactosyl residues and sialic acid. Beta-1,2-xylosyltransferase ("XylT") catalyzes the transfer of xylose from UDP-xylose to the core β-linked mannose of protein-bound N-glycans. This enzyme is unique to plants and some non-vertebrate animal species, and does not occur in human beings or in other vertebrates. α-1,3-fucosyltransferase ("FucT") catalyzes the transfer of fucose from GDP-fucose to the core β-linked N-acetyl glucosamine (GlcNAc) of protein-bound N-glycans. This enzyme is found in plant and animal species, including humans.

SUMMARY

This document provides materials and methods for making plants that are particularly useful for production of therapeutic proteins suitable for administration to humans and animals, particularly by making targeted knockouts in genes encoding xylosyltransferases and fucosyltransferases. This document also provides Nicotiana varieties that lack xylosyltransferase and fucosyltransferase activity, or that have reduced xylosyltransferase and fucosyltransferase activity as compared to corresponding control Nicotiana varieties.

This disclosure is based at least in part on the discovery that plants suitable for producing proteins for administration to humans and animals can be made by knocking out all copies of the genes encoding xylosyltransferases and fucosyltransferases. This disclosure also is based at least in part on the development of Nicotiana benthamiana varieties that lack xylosyltransferase and fucosyltransferase activities. Having the ability to make viable plants that lack xylosyltransferase and fucosyltransferase activities can facilitate production of therapeutic proteins for administration to humans and animals, with a lower incidence of immunogenic or allergic reactions as compared to proteins produced in plants with xylosyltransferase and fucosyltransferase activity.

In addition, this disclosure is based at least in part on the discovery that plants suitable for producing proteins for administration to humans and animals can be made by knocking out or otherwise mutating one or more copies of the genes encoding xylosyltransferases and fucosyltransferases such that transcription of the genes and/or translation of the encoded polypeptide are reduced as compared to a corresponding wild type plant or plant cell, and on the development of Nicotiana benthamiana varieties that have reduced xylosyltransferase and fucosyltransferase activities. The ability to make viable plants that have reduced xylosyltransferase and fucosyltransferase activities also can facilitate production of therapeutic proteins for administration to humans and animals. Reduction of the glycan levels in plant-produced proteins may remove some of the plant-specific characteristics from the proteins. Such proteins may have a lower incidence of immunogenic or allergic reactions as compared to proteins produced in plants that do not have reduced xylosyltransferase and fucosyltransferase activity. Such proteins also may have improved functional activity as compared to proteins that do not have reduced glycan levels.

In one aspect, this document features a Nicotiana plant or plant cell having a mutation in each of a plurality of XylT alleles and a mutation in each of a plurality of FucT alleles, wherein the plant or plant cell does not produce detectable levels of beta-1,2-xylosyl- or core alpha-1,3-fucosyl-sugars on N-glycan structures of glycoproteins produced in the plant or plant cell. The mutations can be at one or more sequences as set forth in SEQ ID NOS:1, 2, or 3. The mutations can have been induced by one or more rare-cutting endonucleases. The one or more rare-cutting endonucleases can be transcription activator-like (TAL) effector endonucleases. Each of the TAL effector endonucleases can bind to a sequence as set forth in any of SEQ ID NOS:45-63. The plant or plant cell can include a nucleic acid encoding a heterologous polypeptide. Each of the mutations can be a deletion of more than one nucleotide. Each of the plurality of XylT alleles and the plurality of FucT alleles can have a deletion of an endogenous nucleic acid sequence and does not include any exogenous nucleic acid. The plant or plant cell can be a N. benthamiana plant or plant cell.

In another aspect, this document features a method for producing a polypeptide. The method can include (a) providing a Nicotiana plant or plant cell having a mutation in each of a plurality of XylT alleles and a mutation in each of a plurality of FucT alleles, wherein the plant or plant cell does not produce detectable levels of beta-1,2-xylosyl- and core alpha-1,3-fucosyl-sugars on N-glycan structures of glycoproteins produced in the plant or plant cell, and wherein the plant or plant cell contains a nucleic acid comprising (i) a nucleotide sequence encoding a polypeptide operably linked to (ii) a plant-expressible promoter and (iii) a sequence involved in transcription termination and polyadenylation, wherein the polypeptide is heterologous to the plant; and (b) growing the plant or plant cell under conditions and for a time sufficient that the heterologous polypeptide is produced. The method can further include isolating the heterologous polypeptide from the plant or plant cell. The mutations can have been induced by one or more rare-cutting endonucleases. The one or more rare-cutting endonucleases can be TAL effector endonucleases. Each of the TAL effector endonucleases can bind to a sequence as set forth in any of SEQ ID NOS:45-63.

In another aspect, this document features a method for making a *Nicotiana* plant that has a mutation in each of a plurality of XylT alleles and a mutation in each of a plurality of FucT alleles. The method can include (a) contacting a population of *Nicotiana* plant cells having functional XylT alleles and functional FucT alleles with one or more rare-cutting endonucleases targeted to endogenous XylT sequences, and one or more rare-cutting endonucleases targeted to endogenous FucT sequences, (b) selecting, from the population, a cell in which a plurality of XylT alleles and a plurality of FucT alleles have been inactivated, and (c) regenerating the selected plant cell into a *Nicotiana* plant, wherein the *Nicotiana* plant contains mutations in a plurality of XylT alleles and mutations in a plurality of FucT alleles, and does not produce detectable levels of beta-1,2-xylosyl- or core alpha-1,3-fucosyl-sugars on N-glycan structures of glycoproteins produced in the plant. The *Nicotiana* plant cells can be protoplasts. The method can include transforming the protoplasts with one or more vectors encoding one or more rare-cutting endonucleases. The one or more rare-cutting endonucleases can be TAL effector endonucleases. Each of the TAL effector endonucleases can be targeted to a sequence as set forth in any of SEQ ID NOS:45-63. The method can include introducing into the protoplasts a TAL effector endonuclease protein. The method can further include culturing the protoplasts to generate plant lines. The method can include isolating genomic DNA comprising at least a portion of a XylT locus or at least a portion of a FucT locus from the protoplasts. The *Nicotiana* plant cells can be *N. benthamiana* plant cells.

In still another aspect, this document features a method for generating a *Nicotiana* plant having a mutation in each of a plurality of XylT alleles and a mutation in each of a plurality of FucT alleles. The method can include (a) crossing a first *Nicotiana* plant having a mutation in at least one XylT allele and a mutation in at least one FucT allele with a second *Nicotiana* plant having a mutation in at least one XylT allele and a mutation in at least one FucT allele, to obtain progeny; and (b) selecting from the progeny a *Nicotiana* plant that has mutations in a plurality of XylT alleles and mutations in a plurality of FucT alleles. The mutations can have been induced by one or more rare-cutting endonucleases. The one or more rare-cutting endonucleases can be TAL effector endonucleases. Each of the TAL effector endonucleases can bind to a sequence as set forth in any of SEQ ID NOS:45-63. Each of the mutations can be a deletion of more than one nucleotide. The progeny can be homozygous for the mutations at each of the alleles.

This document also features a *Nicotiana* plant or plant cell having a mutation in one or more XylT alleles and a mutation in one or more FucT alleles, wherein the levels of beta-1,2-xylosyl- and core alpha-1,3-fucosyl-sugars on N-glycan structures of glycoproteins produced in the plant or plant cell are decreased as compared to a corresponding plant or plant cell that does not contain the mutations. The mutations can be at one or more sequences as set forth in SEQ ID NOS:1, 2, or 3. The mutations can have been induced by one or more rare-cutting endonucleases. The one or more rare-cutting endonucleases can be transcription activator-like (TAL) effector endonucleases. Each of the TAL effector endonucleases can bind to a sequence as set forth in any of SEQ ID NOS:45-63. The plant or plant cell can contain a nucleic acid encoding a heterologous polypeptide (e.g., a recombinant polypeptide). Each of the mutations can be a deletion of more than one nucleotide. Each of the one or more XylT alleles and the one or more FucT alleles can have a deletion of an endogenous nucleic acid sequence and does not include any exogenous nucleic acid. The plant or plant cell can be a *N. benthamiana* plant or plant cell.

In another aspect, this document features a method for producing a polypeptide. The method can include (a) providing a *Nicotiana* plant or plant cell containing a mutation in one or more XylT alleles and a mutation in one or more FucT alleles, wherein the levels of beta-1,2-xylosyl- and core alpha-1,3-fucosyl-sugars on N-glycan structures of glycoproteins produced in the plant or plant cell are decreased as compared to a corresponding plant or plant cell that does not contain the mutations, and wherein the plant or plant cell comprises a recombinant nucleic acid that includes (i) a nucleotide sequence encoding a polypeptide operably linked to (ii) a plant-expressible promoter and (iii) a sequence involved in transcription termination and polyadenylation, wherein the polypeptide is heterologous to the plant; and (b) growing the plant or plant cell under conditions and for a time sufficient that the heterologous polypeptide is produced. The method can further include isolating the heterologous polypeptide from the plant or plant cell. The mutations can have been induced by one or more rare-cutting endonucleases. The one or more rare-cutting endonucleases can be TAL effector endonucleases. Each of the TAL effector endonucleases can bind to a sequence as set forth in any of SEQ ID NOS:45-63.

In yet another aspect, this document features a method for making a *Nicotiana* plant that has a mutation in one or more XylT alleles and a mutation in one or more FucT alleles. The method can include (a) contacting a population of *Nicotiana* plant cells having functional XylT alleles and functional FucT alleles with one or more rare-cutting endonucleases targeted to endogenous XylT sequences, and one or more rare-cutting endonucleases targeted to endogenous FucT sequences, (b) selecting, from the population, a cell in which one or more XylT alleles and one or more FucT alleles have been inactivated, and (c) regenerating the selected plant cell into a *Nicotiana* plant, wherein the *Nicotiana* plant contains mutations in one or more XylT alleles and mutations in one or more FucT alleles, and has reduced levels of beta-1,2-xylosyl- and core alpha-1,3-fucosyl-sugars on N-glycan structures of glycoproteins produced in the plant, as compared to a plant that does not contain the mutations. The *Nicotiana* plant cells can be protoplasts. The method can include transforming the protoplasts with one or more vectors encoding one or more rare-cutting endonucleases. The one or more rare-cutting endonucleases can be TAL effector endonucleases. Each of the TAL effector endonucleases can be targeted to a sequence as set forth in any of SEQ ID NOS:45-63. The method can include introducing into the protoplasts a TAL effector endonuclease protein. The method can further include culturing the protoplasts to generate plant lines. The method can include isolating genomic DNA comprising at least a portion of a XylT locus or at least a portion of a FucT locus from the protoplasts. The *Nicotiana* plant cells can be *N. benthamiana* plant cells.

In another aspect, this document features a method for generating a *Nicotiana* plant having a mutation in one or more XylT alleles and a mutation in one or more FucT alleles. The method can include (a) crossing a first *Nicotiana* plant containing a mutation in at least one XylT allele and a mutation in at least one FucT allele with a second *Nicotiana* plant containing a mutation in at least one XylT allele and a mutation in at least one FucT allele, to obtain progeny; and (b) selecting from the progeny a *Nicotiana* plant that contains mutations in one or more XylT alleles and mutations in one or more FucT alleles. The mutations can have been induced by one or more rare-cutting endonucleases. The one or more rare-cutting endonucleases can be TAL effector endonucleases. Each of the TAL effector endonucleases can bind to a sequence as set forth in any of SEQ ID NOS:45-63. Each of the mutations can be a deletion of more than one nucleotide. The progeny can be homozygous for the mutations at each of the alleles.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows target sites for XylT TAL effector endonucleases. The DNA sequence for both of the XylT genes (XylT1 and XylT2) is shown (SEQ ID NO:1; the DNA sequences for the two XylT genes are the same in this region), beginning with the start codon (ATG). The underlined sequences represent target sites the TAL effector endonucleases that recognize the XylT genes.

FIG. 2 shows target sites for FucT TAL effector endonucleases. The DNA sequences for the two FucT genes (FucT1, SEQ ID NO:2; FucT2, SEQ ID NO:3) are shown, beginning with the start codon (ATG). The underlined sequences represent target sites for TAL effector endonucleases that recognize the FucT genes. Sequence differences between FucT1 and FucT2 are indicated in bold type.

FIG. 3 shows examples of TAL effector endonuclease-induced mutations in the XylT genes. The top line of each panel shows the DNA sequence of the recognition site for the XylT_T04 TAL effector endonucleases (underlined and in capital letters) in either the XylT1 (top panel) or XylT2 (bottom panel) gene. The other sequences show representative mutations that were induced by imprecise non-homologous end joining (NHEJ), with the sizes of deletions given on the right.

FIG. 4 shows examples of TAL effector endonuclease-induced mutations in the FucT genes. The top line of each panel shows the DNA sequence of the recognition site for the FucT2_T02 TAL effector endonucleases (underlined and in capital letters) in either the FucT1 (top panel) or FucT2 (bottom panel) gene. The other sequences show representative mutations that were induced by imprecise NHEJ, with the sizes of deletions given on the right.

FIG. 5 shows FucT1 and FucT2 mutation profiles in the NB13-105a and NB13-213a plant lines. For each alignment, the top sequences are from wild type *N. benthamiana*, and the lower sequences are from mutant plants NB13-105a or NB13-213a. The recognition site for the FucT2_T02 TAL effector endonuclease is underlined in each alignment.

FIG. 6 shows XylT1 and XylT2 mutation profiles in NB15-11d and NB12-113c plant lines. For each alignment, the top sequences are from wild type *N. benthamiana*, and the lower sequences are from mutant plants NB15-11d or NB12-113c. The recognition site for the XylT_T04 TAL effector endonuclease is underlined in each alignment.

FIG. 7 shows FucT1 and FucT2 mutation profiles in the NB14-29a plant line. For each alignment, the top sequences are from wild type *N. benthamiana*, and the lower sequences are from NB14-29a. The recognition site for the FucT2_T02 TAL effector endonuclease is underlined in each alignment.

FIG. 8 shows XylT1 and XylT2 mutation profiles in the NB14-29a plant line. For each alignment, the top sequences are from wild type *N. benthamiana*, and the lower sequences are from NB14-29a. The recognition site for the XylT_T04 TAL effector endonuclease is underlined in each alignment.

DETAILED DESCRIPTION

Figure 9:
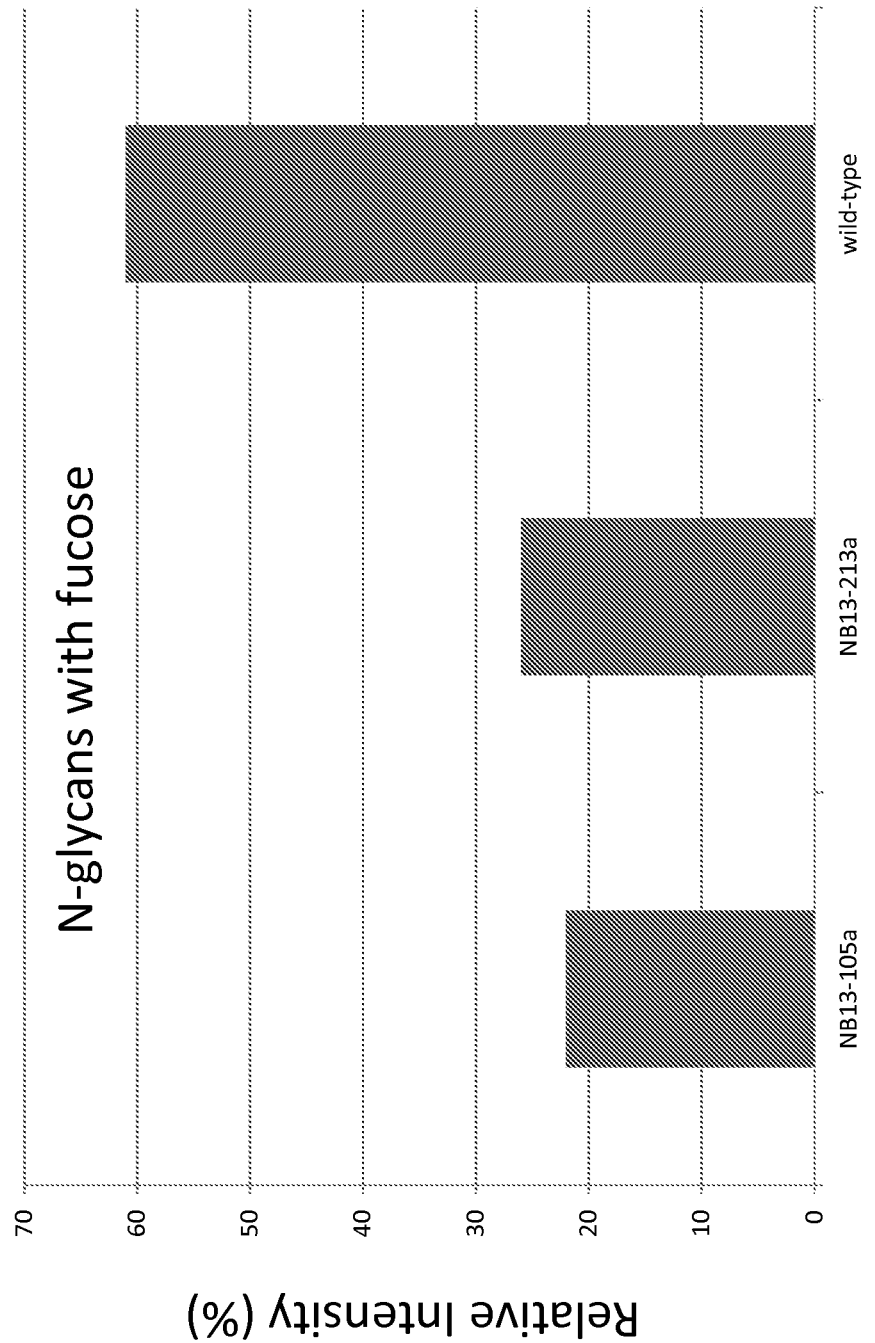
FIG. 9 compares the relative intensities of N-glycans with fucose in NB13-105a, NB13-213a and wild type *N. benthamiana*. The N-glycan data were generated from endogenous *N. benthamiana* proteins via MALDI TOF MS (Matrix-assisted laser desorption-ionization time-of-flight mass spectrometry).

This document provides plants of the genus *Nicotiana* that lack xylosyltransferase and fucosyltransferase activity, as well methods for generating such plants, and methods for using such plants for producing polypeptides suitable for administration to humans and animals. Members of the *Nicotiana* genus include, for example, the species *benthamiana, tabacum, sylvestris, acaulis, acuminate, africana, alata, ameghinoi, amplexicaulis, arentsii, attenuate, azambujae, benavidesii, bonariensis, burbidgeae, cavicola, clevelandii, cordifolia, corymbosa, cutleri, debneyi, excelsior, exigua, forgetiana, fragrans, glauca, glutinosa, goodspeedii, gossei, hesperis, heterantha, ingulba, kawakamii, knightiana, langsdorffii, linearis, longibracteata, longiflora, maritime, megalosiphon, miersii, mutabilis, nesophila, noctiflora, nudicaulis, occidentalis, obtusifolia, otophora, paa, palmeri, paniculata, pauciflora, petuniodes, plumbaginifolia, quadrivalvis, raimondii, repanda, rosulata, rotundifolia, rustica, setchellii, simulans, solanifolia, spegazzinii, stenocarpa, stocktonii, suaveolens, thrysiflora, tomentosa, tomentosiformis, truncata, umbratica, undulate, velutina, wigandioides*, and *wuttkei*.

In *N. benthamiana*, there are at least two members (XylT1 and XylT2) in the xylosyltransferase (XylT) gene family and at least two members (FucT1 and FucT2) in the fucosyltransferase (FucT) gene family. Representative examples of naturally occurring *Nicotiana* XylT and FucT nucleotide sequences are shown in Table 4. The *Nicotiana* plants, cells, plant parts, seeds, and progeny thereof provided herein can have a mutation in each of a plurality of the endogenous XylT and FucT alleles, such that expression of each gene is reduced or completely inhibited. The plants, cells, parts, seeds, and progeny do not exhibit detectable levels of beta-1,2-xylosyl- or core alpha-1,3-fucosyl-sugars on N-glycan structures of glycoproteins produced therein.

In some embodiments, the *Nicotiana* plants, cells, plant parts, seeds, and progeny thereof provided herein can have a mutation in one or more endogenous XylT alleles and one or more endogenous FucT alleles, such that expression of each gene is reduced (e.g., partially or completely reduced). The reduced level of expression can be sufficient to yield plants, cells, parts, seeds, and progeny that exhibit decreased levels of beta-1,2-xylosyl- and core alpha-1,3-fucosyl-sugars on N-glycan structures of glycoproteins produced therein, as compared to the levels of beta-1,2-xylosyl- and core alpha-1,3-fucosyl-sugars on N-glycan structures of glycoproteins produced in corresponding control plants, cells, parts, seeds, and progeny that do not include the XylT and FucT mutations.

The plants, plant cells, plant parts, seeds, and plant progeny provided herein can be generated using a rare-cutting endonuclease, such as a TAL effector endonuclease system, to make targeted knockouts in the XylT and FucT genes. Thus, this disclosure provides materials and methods for using TAL effector endonucleases to generate plants and related products (e.g., seeds and plant parts) that are particularly suitable for production of human and animal therapeutic proteins due to targeted knockouts in all alleles of the XylT and FucT genes. Other rare-cutting, sequence-specific nucleases to be used to generate the desired plant material, including engineered homing endonucleases or zinc finger nucleases.

"Plants" and "plant parts" refers to cells, tissues, organs, seeds, and severed parts (e.g., roots, leaves, and flowers) that retain the distinguishing characteristics of the parent plant. "Seed" refers to any plant structure that is formed by continued differentiation of the ovule of the plant, following its normal maturation point at flower opening, irrespective of whether it is formed in the presence or absence of fertilization and irrespective of whether or not the seed structure is fertile or infertile.

The term "allele(s)" means any of one or more alternative forms of a gene at a particular locus. In a diploid (or amphidiploid) cell of an organism, alleles of a given gene are located at a specific location or locus on a chromosome. One allele is present on each chromosome of the pair of homologous chromosomes. "Heterozygous" alleles are two different alleles residing at a specific locus, positioned individually on corresponding pairs of homologous chromosomes. "Homozygous" alleles are two identical alleles residing at a specific locus, positioned individually on corresponding pairs of homologous chromosomes in the cell.

"Wild type" as used herein refers to a typical form of a plant or a gene as it most commonly occurs in nature. A "wild type XylT allele" is a naturally occurring XylT allele (e.g., as found within naturally occurring *Nicotiana* plants) that encodes a functional XylT protein, while a "mutant XylT allele" is a XylT allele that does not encode a functional XylT protein. Such a "mutant XylT allele" can include one or more mutations in its nucleic acid sequence, where the mutation(s) result in no detectable amount of functional XylT protein in the plant or plant cell in vivo. Similarly, a "wild type FucT allele" is a naturally occurring FucT allele that encodes a functional FucT protein, while a "mutant FucT allele" is a FucT allele that does not encode a functional FucT protein. Such a "mutant FucT allele" can include one or more mutations in its nucleic acid sequence, where the mutation(s) result in no detectable amount of functional FucT protein in the plant or plant cell in vivo.

The term "rare-cutting endonucleases" herein refer to natural or engineered proteins having endonuclease activity directed to nucleic acid sequences having a recognition sequence (target sequence) about 12-40 bp in length (e.g., 14-40 bp in length). Typical rare-cutting endonucleases cause cleavage inside their recognition site, leaving 4 nt staggered cut with 3'OH or 5'OH overhangs. These rare-cutting endonucleases may be meganucleases, such as wild type or variant proteins of homing endonucleases, more particularly belonging to the dodecapeptide family (LAGLI-DADG (SEQ ID NO:79); see, WO 2004/067736) or may result from fusion proteins that associate a DNA binding domain and a catalytic domain with cleavage activity. TAL-effector endonucleases and zinc-finger-nucleases (ZFN) are examples of fusions of DNA binding domains with the catalytic domain of the endonuclease FokI. Customized TAL effector endonucleases are commercially available under the trade name TALEN™ (Cellectis, Paris, France). For a review of rare-cutting endonucleases, see Baker, *Nature Methods* 9:23-26, 2012.

"Mutagenesis" as used herein refers to processes in which mutations are introduced into a selected DNA sequence. In the methods described herein, for example, mutagenesis occurs via a double stranded DNA breaks made by TAL effector endonucleases targeted to selected DNA sequences in a plant cell. Such mutagenesis results in "TAL effector endonuclease-induced mutations" and reduced expression of the targeted gene. Following mutagenesis, plants can be regenerated from the treated cells using known techniques (e.g., planting seeds in accordance with conventional growing procedures, followed by self-pollination).

In some cases, a nucleic acid can have a nucleotide sequence with at least about 75 percent sequence identity to a representative XylT or FucT nucleotide sequence. For example, a nucleotide sequence can have at least 75, at least 80, at least 85, at least 90, at least 91, at least 92, at least 93, at least 94, at least 95, at least 96, at least 97, at least 98, or at least 99 percent sequence identity to a representative, naturally occurring XylT or FucT nucleotide sequence The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq c:\seq1.txt -j c:\seq2.txt -p blastn -o c:\output.txt -q −1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, a nucleic acid sequence that has 80 matches when aligned with the sequence set forth in SEQ ID NO:1 is 88.9 percent identical to the sequence set forth in SEQ ID NO:1 (i.e., 80÷90×100=88.9). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer Methods for selecting endogenous target sequences and generating TAL effector endonucleases targeted to such sequences can be performed as described elsewhere. See, for example, PCT Publication No. WO 2011/072246, which is incorporated herein by reference in its entirety. TAL effectors are found in plant pathogenic bacteria in the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318:648-651, 2007; Sugio et al., *Proc. Natl. Acad. Sci. USA* 104:10720-10725, 2007; and Römer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TAL effectors correspond to the nucleotides in their target sites in a direct, linear fashion, one RVD to one nucleotide, with some degeneracy and no apparent context dependence. This mechanism for protein-DNA recognition enables target site prediction for new target specific TAL effectors, as well as target site selection and engineering of new TAL effectors with binding specificity for the selected sites.

TAL effector DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (i.e., double-stranded breaks) in DNA can induce mutations into the wild type DNA sequence via NHEJ or homologous recombination, for example. In some cases, TAL effector endonucleases can be used to facilitate site directed mutagenesis in complex genomes, knocking out or otherwise altering gene function with great precision and high efficiency. As described below in the Examples, TAL effector endonucleases targeted to each of the *N. benthamiana* XylT and FucT alleles can be used to mutagenize the endogenous genes, resulting in plants without detectable expression of these genes. The fact that some endonucleases (e.g., FokI) function as dimers can be used to enhance the target specificity of the TAL effector endonuclease. For example, in some cases a pair of TAL effector endonuclease monomers targeted to different DNA sequences (e.g., the underlined target sequences shown in FIGS. 1 and 2) can be used. When the two TAL effector endonuclease recognition sites are in close proximity, as depicted in FIGS. 1 and 2, the inactive monomers can come together to create a functional enzyme that cleaves the DNA. By requiring DNA binding to activate the nuclease, a highly site-specific restriction enzyme can be created.

The term "expression" as used herein refers to the transcription of a particular nucleic acid sequence to produce sense or antisense mRNA, and/or the translation of a sense mRNA molecule to produce a polypeptide (e.g., a therapeutic protein), with or without subsequent post-translational events.

"Reducing the expression" of a gene or polypeptide in a plant or a plant cell includes inhibiting, interrupting, knocking-out, or knocking-down the gene or polypeptide, such that transcription of the gene and/or translation of the encoded polypeptide are reduced as compared to a corresponding wild type plant or plant cell. Expression levels can be measured using methods such as, for example, reverse transcription-polymerase chain reaction (RT-PCR), Northern blotting, dot-blot hybridization, in situ hybridization, nuclear run-on and/or nuclear run-off, RNase protection, or immunological and enzymatic methods such as ELISA, radioimmunoassay, and western blotting.

Methods for using TAL effector endonucleases to generate plants, plant cells, or plant parts having mutations in endogenous genes include, for example, those described in the Examples herein. For example, nucleic acids encoding TAL effector endonucleases targeted to selected XylT or FucT sequences (e.g., the XylT sequences shown in FIG. 1 or the FucT sequences shown in FIG. 2) can be transformed into plant cells (e.g., protoplasts), where they can be expressed. The cells subsequently can be analyzed to determine whether mutations have been introduced at the target site(s), through nucleic acid-based assays or protein-based assays to detect expression levels as described above, for example, or using nucleic acid-based assays (e.g., PCR and DNA sequencing, or PCR followed by a T7E1 assay; Mussolino et al., *Nucleic Acids Res.* 39:9283-9293, 2011) to detect mutations at the genomic loci.

The mutagenized population, or a subsequent generation of that population, can be screened for a desired trait(s) (e.g., a lack of xylosyltransferase and fucosyltransferase activities, or reduced xylosyltransferase and fucosyltransferase activities) resulting from the mutations. Alternatively, the mutagenized population, or a subsequent generation of that population, can be screened for a mutation in a XylT or FucT gene. For example, the progeny $M_2$ generation of $M_1$ plants may be evaluated for the presence of a mutation in a XylT or FucT gene. A "population" is any group of individuals that share a common gene pool. As used herein, "$M_0$" refers to plant cells (and plants grown therefrom) exposed to a TAL effector nuclease, while "$M_1$" refers to seeds produced by self-pollinated $M_0$ plants, and plants grown from such seeds. "$M_2$" is the progeny (seeds and plants) of self-pollinated $M_1$ plants, "$M_3$" is the progeny of self-pollinated $M_2$ plants, and "$M_4$" is the progeny of self-pollinated $M_3$ plants. "$M_5$" is the progeny of self-pollinated $M_4$ plants. "$M_6$", "$M_7$", etc. are each the progeny of self-pollinated plants of the previous generation. The term "selfed" as used herein means self-pollinated.

One or more $M_1$ tobacco plants can be obtained from individual, mutagenized ($M_0$) plant cells (and plants grown therefrom), and at least one of the plants can be identified as containing a mutation in a XylT or FucT gene. An $M_1$ tobacco plant may be heterozygous for a mutant allele at a XylT and/or a FucT locus and, due to the presence of the wild-type allele, exhibit xylosyl- or fucosyltransferase activity. Alternatively, an $M_1$ tobacco plant may have a mutant allele at a XylT or FucT locus and exhibit the phenotype of lacking xylosyl- or fucosyltransferase activity. Such plants may be heterozygous and lack xylosyl- or fucosyltransferase activity due to phenomena such a dominant negative suppression, despite the presence of the wild-type allele, or may be homozygous due to independently induced mutations in both alleles at the XylT or FucT locus.

A tobacco plant carrying mutant XylT and FucT alleles can be used in a plant breeding program to create novel and useful lines, varieties and hybrids. Thus, in some embodiments, an $M_1$, $M_2$, $M_3$, or later generation tobacco plant containing at least one mutation in a XylT and at least one mutation in a FucT gene is crossed with a second *Nicotiana* plant, and progeny of the cross are identified in which the XylT and FucT gene mutations are present. It will be appreciated that the second *Nicotiana* plant can be one of the species and varieties described herein. It will also be appreciated that the second *Nicotiana* plant can contain the same XylT and FucT mutations as the plant to which it is crossed, different XylT and FucT mutations, or be wild-type at the XylT and/or FucT loci.

Breeding can be carried out via known procedures. DNA fingerprinting, SNP or similar technologies may be used in a marker-assisted selection (MAS) breeding program to transfer or breed mutant XylT and FucT alleles into other tobaccos. For example, a breeder can create segregating populations from hybridizations of a genotype containing a mutant allele with an agronomically desirable genotype. Plants in the $F_2$ or backcross generations can be screened using markers developed from a XylT and FucT sequences or fragments thereof. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for XylT and FucT gene expression, e.g., a plant is identified that fails to express XylT and FucT due to the absence of a XylT and FucT genes according to standard methods, for example, using a PCR method with primers based upon the nucleotide sequence information for XylT and FucT described herein. Selected plants are then crossed with one of the parents and the first backcross ($BC_1$) generation plants are self-pollinated to produce a $BC_1F_2$ population that is again screened for variant XylT and FucT gene expression (e.g., null versions of the XylT and FucT genes). The process of backcrossing, self-pollination, and screening is repeated, for example, at least 4 times until the final screening produces a plant that is fertile and reasonably similar to the recurrent parent. This plant, if desired, can be self-pollinated, and the progeny subsequently can be screened again to confirm that the plant lacks XylT and FucT gene expression. Cytogenetic analyses of the selected plants optionally can be performed to confirm the chromosome complement and chromosome pairing relationships. Breeder's seed of the selected plant can be produced using standard methods including, for example, field testing, confirmation of the null condition for XylT and FucT, and/or analyses of cured leaf to determine the level of xylosyl- and fucosyltransferase activity.

In situations where the original $F_1$ hybrid resulting from the cross between a first, mutant tobacco parent and a second, wild-type tobacco parent, is hybridized or backcrossed to the mutant tobacco parent, the progeny of the backcross can be self-pollinated to create a $BC_1F_2$ generation that is screened for the mutant XylT and FucT alleles.

The result of a plant breeding program using the mutant tobacco plants described herein can be novel and useful lines, hybrids and varieties. As used herein, the term "variety" refers to a population of plants that share constant characteristics which separate them from other plants of the same species. A variety is often, although not always, sold commercially. While possessing one or more distinctive traits, a variety can be further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972, on Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A "line" as distinguished from a variety most often denotes a group of plants used non-commercially, for example in plant research. A line typically displays little overall variation between individuals for one or more traits of interest, although there may be some variation between individuals for other traits.

Hybrid tobacco varieties can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting $F_1$ seed is harvested.

Varieties and lines described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_1$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

This disclosure also provides methods for producing polypeptides (e.g., therapeutic glycoproteins). In some cases, the plants, cells, plant parts, seeds, and progeny provided herein can contain a nucleic acid molecule encoding a heterologous polypeptide (e.g., a recombinant polypeptide). In some cases, the methods provided herein can include providing a *Nicotiana* plant, plant cell, or plant part having a TAL effector endonuclease-induced mutation in each of a plurality of the endogenous XylT and FucT alleles (e.g., in two or more of the endogenous XylT alleles and in two or more of the endogenous FucT alleles), where the plant, plant cell, or plant part further contains a nucleic acid encoding a heterologous polypeptide (e.g., a recombinant polypeptide). In some cases, the methods provided herein can include providing a *Nicotiana* plant, plant cell, or plant part having a TAL effector endonuclease-induced mutation in one or more of the endogenous XylT and FucT alleles (e.g., in one or more of the endogenous XylT alleles and in one or more of the endogenous FucT alleles), where the plant, plant cell, or plant part further contains a nucleic acid encoding a heterologous polypeptide (e.g., a recombinant polypeptide). The coding sequence for the heterologous polypeptide can be operably linked to a plant-expressible promoter, and also to a sequence involved in transcription termination and polyadenylation. In some cases, the methods also can include maintaining the plant or plant cell under conditions (e.g., suitable temperature, humidity, light/dark, airflow, and nutritional conditions, in a greenhouse and/or in aqueous conditions) and for a time (e.g., 6 to 12 hours, 12 to 24 hours, 24 to 48 hours, 48 hours to 7 days, 7 days to 30 days, or more than 30 days) sufficient for the polypeptide to be produced. In some cases, the methods for producing a polypeptide can further include isolating the expressed polypeptide from the plant or plant cell. Techniques for isolating such polypeptides can include, for example, conventional techniques such as extraction, precipitation, chromatography, affinity chromatography, and electrophoresis.

A "plant-expressible promoter" is a DNA sequence that is capable of controlling (initiating) transcription in a plant cell. This includes any promoter of plant origin, as well as any promoter of non-plant origin that is capable of directing transcription in a plant cell [e.g., promoters of viral or bacterial origin such as the CaMV35S promoter, T-DNA gene promoters, tissue-specific or organ-specific promoters such as seed-specific promoters, organ specific promoters (e.g., stem-, leaf-, root-, or mesophyll-specific promoters)].

In some cases, a *Nicotiana* plant, plant cell, plant part, seed, or progeny provided herein can contain a nucleic acid encoding a heterologous polypeptide. A "heterologous polypeptide" is a polypeptide that is not naturally occurring in the plant or plant cells. This is in contrast with homologous polypeptides, which are polypeptides naturally expressed by the plant or plant cells. Heterologous and homologous polypeptides that undergo post-translational N-glycosylation are referred to herein as heterologous or homologous glycoproteins, respectively.

Examples of heterologous polypeptides that can be produced using the plants and methods described herein for administration to humans or animals include, without limitation, cytokines, cytokine receptors, growth factors, growth factor receptors, growth hormones, insulin, pro-insulin, erythropoietin, colony stimulating factors, interleukins, interferons, tumor necrosis factor, tumor necrosis factor receptor, thrombopoietin, thrombin, natriuretic peptides, clotting factors, anti-clotting factors, tissue plasminogen activator, urokinase, follicle stimulating hormone, luteinizing hormone, calcitonin, CD proteins, CTLA proteins, T-cell and B-cell receptor proteins, bone morphogenic proteins, neurotrophic factors, rheumatoid factor, RANTES, albumin, relaxin, macrophage inhibitory protein, viral proteins or antigens, surface membrane proteins, enzymes, regulatory proteins, immunomodulatory proteins, homing receptors, transport proteins, superoxide dismutase, G-protein coupled receptor proteins, neuromodulatory proteins, antigens (e.g., bacterial or viral antigens), and antibodies or fragments thereof. In some cases, the plant-produced polypeptides can be used as vaccines.

"Antibodies" include antibodies of the classes IgD, IgG, IgA, IgM, IgE, as well as recombinant antibodies such as single-chain antibodies, chimeric and humanized antibodies, and multi-specific antibodies. The term "antibody" also refers to fragments and derivatives of all of the foregoing, and may further include any modified or derivatized variants thereof that retain the ability to specifically bind an epitope. Antibodies include monoclonal antibodies, polyclonal antibodies, humanized or chimeric antibodies, camelized antibodies, camelid antibodies, single chain antibodies (scFvs), Fab fragments, F(ab')$_2$ fragments, disulfide-linked Fvs (sdFv) fragments, anti-idiotypic antibodies, intra-bodies, synthetic antibodies, and epitope-binding fragments of any of the above. The term "antibody" also refers to fusion proteins that include a region equivalent to the Fc region of an immunoglobulin.

The invention will be further described in the following examples, which do not limit the scope of the invention described in the claims.

EXAMPLES

Example 1—Engineering Sequence-Specific Nucleases to Mutagenize the FucT and XylT Gene Families In *N. benthamiana*, mutations were sought in two FucT genes (FucT1 and FucT2) and two XylT genes (XylT1 and XylT2). Since each gene has two alleles, inactivation of these genes required the introduction of mutations at eight target sites.

To completely inactivate or knock-out the members of the XylT gene family in *N. benthamiana*, sequence-specific nucleases were designed that target the protein coding region in the vicinity of the start codon. The first 90-bp of the coding sequences are identical between the XylT1 and XylT2 genes (FIG. 1). Four TAL effector endonuclease pairs were designed to target the XylT gene family within the first 90 bp using software that specifically identifies TAL effector endonuclease recognition sites, such as TALE-NT 2.0 (Doyle et al., *Nucleic Acids Res.* 40:W117-122, 2012). The TAL effector endonuclease recognition sites for the XylT genes are underlined in FIG. 1 and are listed in Table 1. TAL effector endonucleases were synthesized using methods similar to those described elsewhere (Cermak et al., *Nucleic Acids Res.* 39:e82, 2011; Reyon et al., *Nat. Biotechnol.* 30:460-465, 2012; and Zhang et al., Nat. Biotechnol. 29:149-153, 2011).

The first 130-bp of the coding sequences for the FucT1 and FucT2 genes are conserved but not identical (FIG. 2). TAL effector endonucleases targeting the FucT gene family were engineered using a similar strategy as described above, but because the FucT gene sequences are more divergent than XylT1 and XylT2, sequence variations are present in all four TAL effector endonuclease target sites (bold type in FIG. 2). The TAL effector endonuclease recognition sites for FucT genes are underlined in FIG. 2 and are listed in Table 1. Target sites 1 and 2 contain nucleotide polymorphisms in the TAL effector endonuclease recognition sites, and so two TAL effector endonuclease pairs were generated for each target region to increase the likelihood that the TAL effector endonucleases would recognize their target. For target sites 3 and 4, sequence variations occur in the spacer regions between the TAL effector endonuclease DNA recognition sites, and thus a single TAL effector endonuclease pair binds to the same target sequence in both genes.

Example 2—FucT and XylT TAL Effector Endonuclease Activity in Yeast

To assess the activity of the TAL effector endonucleases targeting the XylT and FucT genes, activity assays were performed in yeast by methods similar to those described elsewhere (Christian et al., *Genetics* 186:757-761, 2010). For these assays, a target plasmid was constructed with the TAL effector endonuclease recognition site cloned in a non-functional β-galactosidase reporter gene. The target site was flanked by a direct repeat of β-galactosidase coding sequence such that if the reporter gene was cleaved by the TAL effector endonuclease, recombination would occur between the direct repeats and function would be restored to the β-galactosidase gene. β-galactosidase activity, therefore, served as a measure of TAL effector endonuclease cleavage activity.

In the yeast assay, two of the XylT TAL effector endonuclease pairs (XYL_T03 and XYL_T04) exhibited high cleavage activity under two distinct temperature conditions (i.e., 37° C. and 30° C.). Five of the FucT TAL effector endonuclease pairs (two for target site 1, two for target site 2, and one for target site 4) exhibited high cleavage activities at both 37° C. and 30° C. Cleavage activities were normalized to the benchmark nuclease, I-SceI. Results are summarized in Table 2.

Example 3—Activity of the FucT and XylT TAL Effector Endonucleases at their Endogenous Target Sites in *N. benthamiana*

TAL effector endonuclease activity at endogenous target sites in *N. benthamiana* was measured by expressing the TAL effector endonucleases in protoplasts and surveying the TAL effector endonuclease target sites for mutations introduced by NHEJ. Methods for protoplast preparation were performed as described elsewhere (Wright et al., *Plant J.* 44:693-705, 2005). Briefly, seeds were sterilized by washing them successively with 100% ethanol, 50% bleach and then sterile distilled water. The sterilized seeds were planted on MS agarose medium supplemented with iron. Protoplasts were isolated from young expanded leaves using the protocol described by Wright et al. (supra).

TAL effector endonuclease-encoding plasmids together with a YFP-encoding plasmid were introduced into *N. benthamiana* protoplasts by PEG-mediated transformation as described elsewhere (Yoo et al., *Nature Protocols* 2:1565-1572, 2007). Twenty-four hours after treatment, transformation efficiency was measured by evaluating an aliquot of the transformed protoplasts using a flow cytometer to monitor YFP fluorescence. The remainder of the transformed protoplasts was harvested, and genomic DNA was prepared by a CTAB-based method. Using the genomic DNA prepared from the protoplasts as a template, an approximately 300-bp fragment encompassing the TAL effector endonuclease recognition site was amplified by PCR. The PCR product was then subjected to 454 gyro-sequencing. Sequencing reads with insertion/deletion (indel) mutations in the spacer region were considered as having been derived from imprecise repair of a cleaved TAL effector endonuclease recognition site by NHEJ. Mutagenesis frequency was calculated as the number of sequencing reads with NHEJ mutations out of the total sequencing reads. The values were then normalized by the transformation efficiency.

The activity of the TAL effector endonuclease pairs, XylT03 and XylT04, against their target genes is summarized in Table 3. Both TAL effector endonuclease pairs induced very high frequencies of NHEJ mutations in both XylT1 and XylT2, ranging from 28.2% to 73.8%. Examples of TAL effector endonuclease-induced mutations in XylT1 and XylT2 are shown in FIG. 3. For the FucT1_T02 and FucT2_T02 TAL effector endonuclease pairs, the recognition site of each TAL effector endonuclease pair was conserved in both the FucT1 and FucT2 genes with the exception of a 1-bp polymorphism in one of the two TAL effector endonucleases comprising each pair. As summarized in Table 3, these TAL effector endonuclease pairs generated high frequencies of NHEJ-induced mutations in both genes, ranging from 24.7% to 46.5%. Examples of TAL effector endonuclease-induced mutations on FucT1 and FucT2 loci are shown in FIG. 4.

Example 4—*N. benthamiana* Lines with TAL Effector Endonuclease-Induced Mutations in XylT or FucT

*N. benthamiana* lines were created with mutations in the XylT or FucT genes. Based on the 454 gyro-sequencing data, the TAL effector endonuclease pairs with the highest cleavage activity (XylT_T04 and FucT2_T02), were chosen to mutagenize the XylT and FucT genes. Protoplasts were isolated from sterile leaves, and transformed with plasmids encoding one of the following: (i) TAL effector endonuclease XylT_T04; (ii) TAL effector endonuclease FucT2_T02; or (iii) YFP. Transformation efficiencies were monitored by the delivery of the YFP plasmid, which was visualized using a fluorescent microscope or by flow cytometry as described above.

After transformation, protoplast-derived calli were generated (Van den Elzen et al., *Plant Mol. Biol.* 5:299-302, 1985). Immediately after PEG-mediated transformation, protoplasts were re-suspended in K3G1 media at the cell density of $1 \times 10^5$/ml in a small petri dish, and stored at 25° C. in the dark. At day 4 after transformation, when the majority of the protoplasts were beginning their first cell division, the protoplast culture was diluted four-fold in Media C (Van den Elzen et al., supra). At day 7 and day 10, the protoplast cultures were diluted two-fold in MS media. At day 18 after transformation, calli were identified under the light microscope, and one month after transformation, protoplast-derived calli were visible to the eye. These visible calli were transferred to shoot-inducing medium. After shoots of a few cm in length emerged, they were cut at the base and transferred to root-inducing medium. Once roots formed, they were transferred to soil.

A small piece of leaf tissue was used to prepare genomic DNA from the regenerated plants. DNA samples were assessed by PCR amplification of the target locus and DNA sequencing to identify those plants with mutations in XylT or FucT. As shown in FIG. 5, plant line NB13-105a has sustained identical 13 bp deletions in both alleles of the FucT1 gene, and identical 14 bp deletions in both alleles of the FucT2 gene. Plant line NB13-213a sustained 20 bp and 12 bp deletions in the two alleles of FucT1. NB12-213a also sustained 13 bp and 2 bp deletions in the two alleles of FucT2. Plant line NB12-213a, therefore, has mutations in all FucT targets—the two alleles of FucT1 and the two alleles of FucT2. As shown in FIG. 6, plant line NB15-11d has different 7 bp deletions in each XylT1 allele and an 8 bp deletion in one allele of XylT2. Plant line NB12-113c has a 7 bp deletion in one allele of XylT1 and 35 bp and 5 bp deletions in each of the two alleles of XylT2. Seeds were collected from the modified plants, and inheritance of the mutations was monitored in the progeny, confirming stable, heritable transmission of the modified loci.

Example 5—*N. benthamiana* Lines with TAL Effector Endonuclease-Induced Mutations in XylT and FucT To create *N. benthamiana* lines with mutations in all alleles of all four XylT and FucT genes, protoplasts were transformed with both TAL effector endonucleases, XylT_T04 and FucT2_T02 (Yoo et al., *Nature Protocols* 2:1565-1572, 2007; and Zhang et al., *Plant Physiol.* 161: 20-27, 2012). As described above (Van den Elzen et al., *Plant Mol. Biol.* 5:299-302, 1985), plantlets were regenerated and screened for mutations in the XylT and FucT genes. Screening was performed by PCR amplification of the target and DNA sequence analysis of the amplification products.

Using this approach, plant line NB14-29a was identified that as having deletion mutations in all eight alleles of four loci. This plant line is homozygous for a 44 bp deletion at FucT1 and heterozygous for 2 bp and 40 bp deletions at FucT2 (FIG. 7). This same plant line, NB14-29a, is homozygous for a 5 bp deletion at XylT1 and is heterozygous for 6 bp and 549 bp deletions at XylT2 (FIG. 8). Transmission of the mutations was monitored in the progeny of NB14-29a, demonstrating that the mutations were heritable.

In alternative studies, *N. benthamiana* lines with mutations in one or more XylT alleles are crossed with the *N. benthamiana* lines having mutations in one or more FucT alleles. In subsequent generations, the resulting progeny are screened for those individuals that are homozygous for all mutations present in the parental lines. Additional crosses may be performed with other lines that have mutations in other FucT or XylT genes. Such iterative crossing is used to generate plants that are homozygous for mutant alleles of XylT and FucT. Screening for mutations is performed by PCR amplification and direct DNA sequencing of the PCR products from individual plants.

Example 6—Mutant *N. benthamiana* Lines with Reduced Levels of α1,3-Fucose and Lacking Detectable β1,2-Xylose The presence of α1,3-fucose and β1,2-xylose on endogenous proteins in the mutant *N. benthamiana* lines was assessed by mass spectrometry (North et al., *Curr. Opin. Struct. Biol.* 19:498-506, 2009). Using a similar approach (Strasser et al., *Plant Biotechnol. J.* 6:392-402, 2008), soluble proteins were isolated from green leaves of NB13-105a, NB13-213a, NB15-11d, NB12-113c, and wild type *N. benthamiana*. N-glycans were released from proteins by digestion with peptide-N-glycosidase A and F. Released N-glycans were purified using Ultra Clean SPE Carbograph columns (Alltech) and methylated in vitro. Permethylated N-glycans were analyzed via MALDI TOF MS (Matrix-assisted laser desorption-ionization time-of-flight mass spectrometry) (Karas and Hillenkamp, *Anal. Chem.* 60:259-280, 1988).

Figure 10:
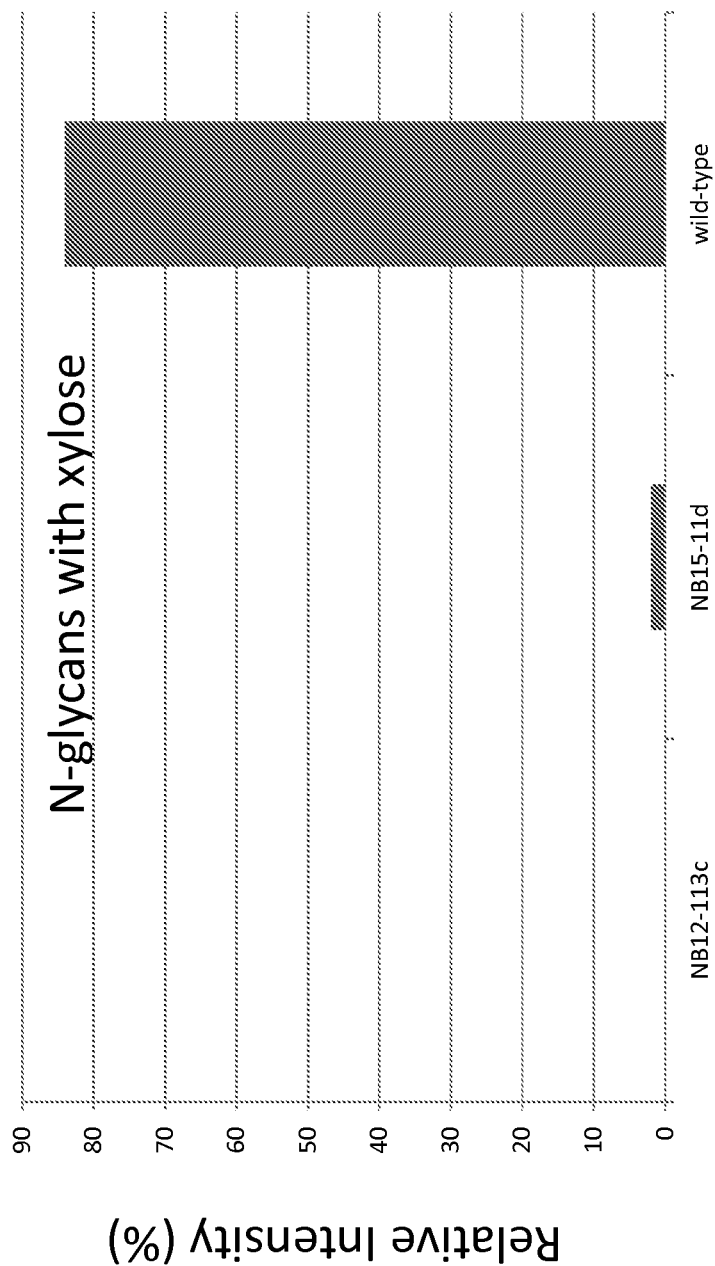
FIG. 10 compares the relative intensities of N-glycans with xylose in NB12-113c, NB15-11d and wild type *N. benthamiana*. The N-glycan data were generated from endogenous *N. benthamiana* proteins via MALDI TOF MS.

N-glycosylation analysis showed reduced levels (more than 60%) of fucosylation in NB13-105a and NB13-213a compared to wild type *N. benthamiana* (FIG. 9). Mutations of XylT1 and XylT2 in NB15-11d and NB12-113c led to undetectable levels of xylosylation on leaf proteins (FIG. 10).

Figure 11:
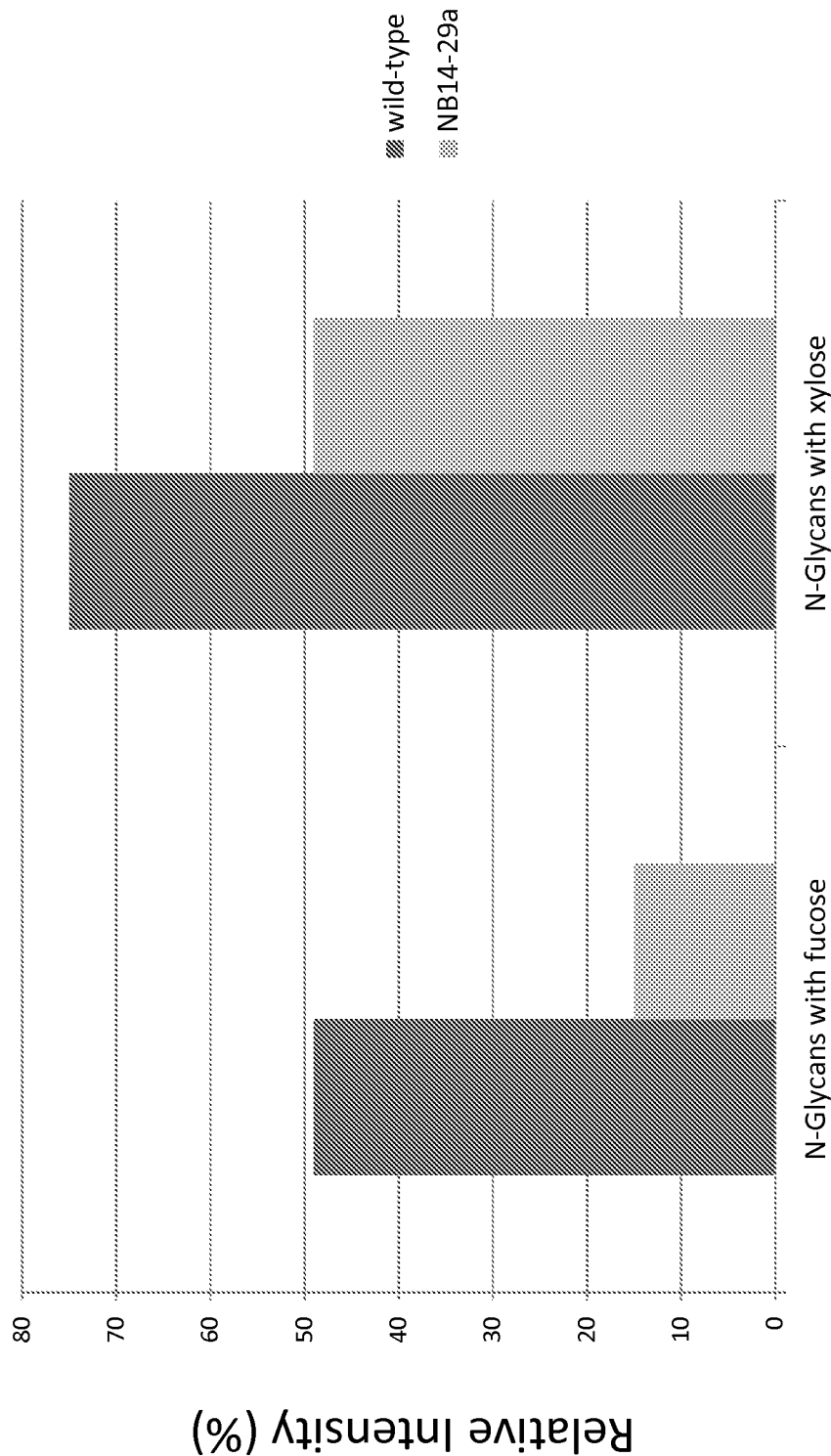
FIG. 11 compares the relative intensities of N-glycans with fucose and xylose in NB14-29a and wild type *N. benthamiana*. The N-glycan data were generated from endogenous *N. benthamiana* proteins via MALDI TOF MS.

N-glycosylation analysis also was performed on endogenous proteins purified from line NB14-29a, which has mutations in all eight alleles of the FucT and XylT genes (FIGS. 7 and 8). As in lines NB13-105a and NB13-213a, fucosylation was significantly reduced in NB14-29a (FIG. 11). The presence of β1,2-xylose on endogenous proteins also was reduced in NB14-29a (FIG. 11), but not to as great an extent as observed for NB15-11d and NB12-113c (FIG. 10). This likely was because line NB14-29a has an in-frame mutation in one allele of XylT2 (specifically, it has a 6 bp deletion, FIG. 8), and this allele can likely produce a functional protein with xylosyl transferase activity.

Example 7—Mutant *N. benthamiana* Lines have Reduced Levels of α1,3-Fucose and β1,2-Xylose on Expressed Polypeptides The presence of α1,3-fucose and β1,2-xylose on heterologous polypeptides expressed in the mutant *N. benthamiana* lines is assessed by mass spectrometry (Strasser et al., *Plant Biotechnol. J.* 6:392-402, 2008). A heterologous polypeptide, such as a human immunoglobulin (e.g., IgG), is expressed by introducing into the mutant *N. benthamiana* lines the coding sequence for the polypeptide by, for example, *agrobacterium* infiltration (Yang et al., *Plant J.* 22:543-551, 2000) or electroporation of protoplasts derived from mutant lines. Nine days after *agrobacterium* infiltration or 48 hours after electroporation, total polypeptides are extracted from mutant plants, and IgG is purified using protein G. The heavy chain of the purified antibody is isolated by cutting the corresponding band from a reduced SDS-PAGE gel. The heavy chain protein in this band is used for glycan analysis by LC-MS as described by Strasser et al. (supra).

TABLE 1

TAL effector endonuclease target sequences

| Gene | Target sequence | SEQ ID NO: | Target sequence 2 | SEQ ID NO: |
|---|---|---|---|---|
| XylT_T01 | TGAACAAGAAAAAGCTG | 45 | TCTTCGCTCTCAACTCA | 46 |
| XylT_T02 | TGAAAATTCTTGTTTCT | 47 | AACTCAATCACTCTCTA | 48 |
| XylT_T03 | TTCTTGTTTCTCTCTTC | 49 | ATCACTCTCTATCTCTA | 50 |
| XylT_T04 | TCTCTTCGCTCTCAACT | 51 | CTCTACTTCTCTTCCCA | 52 |
| FucT1_T01 | TGAGATCGGCGTCAAAT | 53 | AATAAGCAATGGCGCAA | 54 |
| FucT2_T01 | TGAGATCGTCGTCAAAT | 55 | GATAAACAATGGCGCAA | 56 |
| FucT1_T02 | TTCAAACGCACCCAATA | 57 | CTCTGTTCGTTGCCCTA | 58 |
| FucT2_T02 | TTCAAACGCACCCGATA | 59 | CTCTGTTCGTTGCCCTA | 58 |
| FucT1_T03 | TCTGTTCGTTGCCCTAG | 60 | TTTCTTTTCTGGTTCGA | 61 |
| FucT2_T03 | TCTGTTCGTTGCCCTAG | 60 | TTTCTTTTCTGGTTCGA | 61 |
| FucT1_T04 | TTGCCTCTGTTCGTTGC | 62 | TTTCTGGTTCGACTCGA | 63 |
| FucT2_T04 | TTGCCTCTGTTCGTTGC | 62 | TTTCTGGTTCGACTCGA | 63 |

TABLE 2

XylT and FucT TAL effector endonuclease activity in yeast

| TAL effector endonuclease Name | TAL effector endonuclease target* | SEQ ID NO: | Comment | Activity in yeast** 37° C. | Activity in yeast** 30° C. |
|---|---|---|---|---|---|
| XylT_T03 | TTCTTGTTTCTCTCTTCGCTCTCAACTCAATCACTCTCTATCTCTA | 64 | Conserved for both XylT1 and XylT2 | 0.9 | 0.7 |
| XylT_T04 | TCTCTTCGCTCTCAACTCACTCTCTATCTCTACTTCTCTTCCCA | 65 | Conserved for both XylT1 and XylT2 | 0.9 | 0.9 |
| FucT1_T01 | TGAGATCGGCGTCAAATTCAAACGCACCC<u>A</u>CTAAGCAATGGCGCAA | 66 | Variation in DNA binding domain | 0.8 | 0.6 |
| FucT2_T01 | TGAGATCG<u>T</u>CGTCAAATTCAAACGCACCC<u>G</u>ATAAACAATGGCGCAA | 67 | | 0.9 | 0.8 |
| FucT1_T02 | TTCAAACGCACCC<u>A</u>ATAAGCAATGGCGCAATTGGTTGCCTCTGTTCGTTGCCCTA | 68 | Variation in DNA binding domain | 0.9 | 0.7 |
| FucT2_T02 | TTCAAACGCACCC<u>G</u>ATAAACAATGGCGCAATTGGTTGCCTCTGTTCGTTGCCCTA | 69 | | 0.9 | 0.7 |
| FucT1_T04 | TTGCCTCTGTTCGTTGCCCTAGTGATTATAGCT<u>G</u>AG<u>T</u>TTTCTTTTCTGGTTCGACTCGA | 70 | Conserved in binding domain, variation in spacer | 0.6 | 0.5 |
| FucT2_T04 | TTGCCTCTGTTCGTTGCCCTAGTTGTTATAGC<u>A</u>GA<u>A</u>ATTTCTTTTCTGGTTCGACTCGA | 71 | | 0.6 | 0.5 |

*Underlining indicates variations
**Normalized to I-SceI (max = 1.0)

TABLE 3

454 Pyro-Sequencing Data for XylT and FucT TAL effector endonucleases

| TAL effector endo-nuclease name | Location of target site | NHEJ mutagenesis freq. with TAL effector endonuclease* | NHEJ mutagenesis freq. with negative control** | Protoplast transfor-mation efficiency |
|---|---|---|---|---|
| XylT_T03 | XylT1 | 34.4% (3169) | 0.36% | 81% |
| | XylT2 | 28.2% (420) | 0.06% | 81% |
| XylT_T04 | XylT1 | 73.8% (1615) | 0.36% | 84% |
| | XylT2 | 63.9% (464) | 0.06% | 84% |
| FucT1_T02 | FucT1 | 39.2% (27470) | 0.79% | 87% |
| | FucT2 | 24.7% (7259) | 0.14% | 87% |
| FucT2_T02 | FucT1 | 46.5% (12295) | 0.79% | 87% |
| | FucT2 | 45.0% (6457) | 0.14% | 87% |

*NHEJ mutagenesis frequency was obtained by normalizing the percentage of 454 reads with NHEJ mutations to the protoplast transformation efficiency. The total number of 454 sequencing reads used for this analysis was indicated in parentheses.
**Negative controls were obtained from protoplasts transformed only by the YFP-coding plasmid.

TABLE 4

Representative XylT and FucT sequences

*N. benthamiana* XylT1
(GenBank EF562628.1; SEQ ID NO: 72)

gatccagaaaagcactgaacgttgtttaaccctctgtagtctac tctgtactaagtagtacacacgaaaacagccagtcggagagaga agaagatgaacaagaaaaagctgaaaattcttgtttctctcttc gctctcaactcaatcactctctatctctacttctcttcccacca gatcacaaatcccccaaaaccactttcatgtcggaaaaccac catcataatttccactcttcaatcacttctcaatattccaagcc ttggcctattttgccctcctacctcccttggtctcaaaacccta atgttgcttggagatcgtgcgagggttacttcggtaatgggttt actctcaaagttgaccttctcaaaacttcgccggagtttcaccg TABLE 4-continued Representative XylT and FucT sequences gaaattcggcgataacaccgtctccggtgacggcggatggttta
ggtgttttttcagtgagactttgcagagttcgatctgcgaggga
ggcgcaatacgaatgaatccggacgatattttgatgtctcgtgg
aggtgagaaattggagtcggttattggtaggaatgaagatgatg
agctgcccatgttcaaaaatggagctttccaaattgaagttact
gataaactgaaaattgggaaaaaactagtggataaaaaattctt
gaataaatacttaccgggaggtgcgatttcaaggcacactatgc
gtgagttaattgactctattcagttggttggcgccgatgaattt
cactgttctgagtgggttgaggagccgtcacttttgattacacg
atttgagtatgcaaaccttttccacacagttaccgattggtata
gtgcatacgcggcatccagggttactggtttgcccagtcggcca
aatttggttttgtagatggccattgtgagacacaattggagga
acatggaaagcacttttttcaagcctcacttatgctaagaact
ttagtggcccagtttgtttccgtcatgctgtcctctcgccttta
ggatatgaaactgccctgtttaagggactgtcagaaactataga
ttgtaatggagcttctgctcatgatttgtggcaaaagcctgatg
ataaaaaaactgcacggttgtccgagtttggggagatgatcagg
gcagcctttggatttcctgtggatagacagaacatcccaaggac
agtcacaggccctaatgtcctctttgttagacgtgaggattatt
tagctcacccacgtcatggtggaaaggtacagtctaggcttagc
aatgaagagctagtatttgattccataaagagctgggccttgaa
ccactcggagtgtaaattaaatgtaattaacggattgtttgccc
acatgtccatgaaagagcaagttcgagcaatccaagatgcttct
gtcattgttggtgctcatggagcaggtctaactcacatagtttc
tgcagcaccaaaagctgtaatactagaaattataagcagcgaat
ataggcgcccccattttgctctgattgcacaatggaaaggattg
gagtaccatcccatatatttggaggggtcttatgcggatcctcc
agttgtgatcgacaagctcagcagcattttgaggagtcttgggt
gctaaatctgctcgacagtttagttcggcttttctctaaaagat
tgggaaggatagaggaattcggggttctgaaacttggagcctgg
gaattgtgtaaaatatgtttcacacgcagttctatagtcaattg
ctgcaatctggtgttcataagcttggaaatttccagcagctact
aacttattagcccactagactcagttatggactaccagagagca
attcacaagtaacacgtgtatgtgaaagatccatt N. benthamiana XylT2
(GenBank EF562629.1; SEQ ID NO: 73)
agtacagacgaaaacagcccgtgagagagagagagaggagaa
gaagatgaacaagaaaaagctgaaaattcttgtttctctcttcg
ctctcaactcaatcactctctatctctacttctcttcccaccct
gatcactctcgtcgcaaatcccccagaaccacttttcctcgtc TABLE 4-continued Representative XylT and FucT sequences ggaaaaccaccatcataatttccactcttcaatcacttcccaat
attccaggccttggcctattttgccacctacctccatggtctca
aaaccctaatgttgcttggagatcatgcgagggttacttcggta
atggttttactctcaaagttgatcttctcaaaacttcgccggag
cttcaccggaaattcggcgaaaacaccgtcttcggagacggcgg
atggtttaggtgtttcttcagtgagactttgcagagttcgatct
gcgagggaggcgcaatacgaatgaatccagacgagattttgatg
tctcgtggaggtgagaaattggagtcggttattggtaggagtga
agatgatgaggtgcccgcgttcaaaactggagcttttcagatta
aagttactgataaactgaaatttgggaaaaaattagtggatgaa
aacttcttgaataaatacttaccggaaggtgcaatttcaaggca
cactatgcgtgagttaatcgactctattcagttggttggcgcca
atgattttcactgttctgagtggattgaggagccgtcacttttg
attacacgatttgagtatgcaaaccttttccacacaattaccga
ttggtatagtgcatacgtggcatcgagggttactggcttgccca
gtcggccacatttggttttgtagatggccattgtgagacacaa
ttggaggaaacatggaaagcacttttttcaagcctcacttatgc
taagaactttagtggcccagtttgtttccgtcatgccgtcctct
cgcctttgggatatgaaactgccctgtttaagggactgtcagaa
actatagattgtaatggagcttctgctcatgatttgtggcaaaa
tcctgatgataagaaaactgcacggttatccgagtttggggaga
tgatcagggcagcctttggatttcctgttgatagacagaacatc
ccaaggacagtcacaggccctaatgtcctattgttagacgtgag
gattatttagctcacccacgtcatggtggaaaggtacagtctag
gcttagcaatgaagagcaagtatttgattccataaagagctggg
ccttaaaccactcggagtgcaaattaaatgtaattagtggattg
tttgccacatgtccatgaaagagcaagttcgagcaatccaaga
tgcttctgtcattgttggtgacatggagcaggtctaacccacat
agtttctgcagcaccaaaagctgtaatactagaaattataagca
gcgaatataggcgcccccattttgctctgattgctcaatggaaa
ggattggagtaccatcccatatatttggaggggtcttatgcgga
tcctccagttgtgatcgacaagctcagcagcattttgaggagtc
ttgggtgctaaatctgctcgacagtttgaatagattagtttttg
tctaaaagactgggaaggaaaagaggagtttgggggttctgcaa
catggagcatgagaattgtgtaaaatatgtttcacacgcagttc
tatagtcaattgctgcaatctggtgtttataagcttggaaattt
ccagcagctactaacttattagcccactctgactcagttatgga
ctaccagagcaatcatatcaaatgggagcatggaatcctgattg
tggaattgtgatctcattgaagagcatattctttaaggtgttga TABLE 4-continued Representative XylT and FucT sequences agattacagttgaccagtaacacgtgtatgtgaaagattaggtt gttacactttcttgcaattcattgtcaatttttttattaatggt cataggataagaacatgagaaaaccatccatgttctgtgttgtt ttcccatcaatctggccaccctctttcctccttatgttgagatg N. tabacum XylT
(GenBank DQ192540.1; SEQ ID NO: 74)
gtcagagagagaagaagatgaacaagaaaaagctgaaatttctt gtttctctcttcgctctcaactcaatcactctctatctctactt ctcttcccactctgatcacttccgtcacaaatcccccaaaacc actttcctaatacccaaaaccactattccctgtcggaaaaccac catgataatttccactcttctgtcacttcccaatataccaagcc ttggccaattttgccctcctacctcccctggtctcagaatccta atgtttctttgagatcgtgcgagggttacttcggtaatgggttt actctcaaagttgatcttctcaaaacttcgccggagcttcacca gaaattcggcgaaacaccgtatccggcgacggcggatggttta ggtgttttttcagtgagactttgcagagttcgatttgcgaggga ggtgctatacgaatgaatccggacgagattttgatgtctcgtgg aggcgagaaattggagtcggttattggtaggagtgaagatgatg agctgcccgtgttcaaaaatggagcttttcagattaaagttact gataaactgaaaattgggaaaaaattagtggatgaaaaaatctt gaataaatacttaccggaaggtgcaatttcaaggcacactatgc gtgaattaattgactctattcagttagttggcgccgatgaattt cactgttctgagtggattgaggagccgtcacttttgattacacg atttgagtatgcaaaccttttccacacagttaccgattggtata gtgcatacgtggcatccagggttactggcttgcccagtcggcca catttggttttttgtagatggccattgtgagacacaattggagga aacatggaaagcactcttttcaagcctcacttatgctaagaact ttagtggcccagtttgtttccgtcacgccgttctctcgcctttg ggatatgaaactgccctgtttaagggactgacagaaactataga ttgtaatggagcttctgcccatgatttgtggcaaaatcctgatg ataagagaactgcacggttgtccgagtttggggagatgatcagg gcagcctttggatttcctgtggatagacagaacatcccaaggac agtcacaggccctaatgtcctctttgttagacgtgaggattatt tagctcaccacgtcatggtggaaaggtacagtctaggcttagc aatgaagagcaagtatttgattccataaagagctgggccttgaa ccactcggagtgcaaattaaatgtaattaacggattgtttgccc acatgtccatgaaagagcaagttcgagcaatccaagatgcttct gtcatagttggtgctcatggagcaggtctaactcacatagtttc tgcagcaccaaaagctgtaatactagaaattataagcagcgaat ataggcgcccccattttgctctaattgcacaatggaaaggattg gagtaccatcccatatatttggagggggtcttatgcggatcctcc agttgtgatcgacaagctcagcagcattttgaggagtcttgggt gctaaatctgctcgacagtttagttcgtcttttctctaaaagac tgggaaggatagaggaattcggggttctggaacctggagcctgg gaattgtgtaaaatatgtttcacacgcagttctatagtcaattg ctgcaatctggtgttcataagcttggaaatttccagcagctact aacttattagcccactctgactcagttatggactaccagagcaa tcatatcaaatgggagcatggaatcctgattgtggaatggtgag acattgaagagcatattattatggtgttgaagattacagttgac gagtaacacgtgtatgtgaaagattaggttgttacacttttcttg caattcattgtcaattgttttttcgtcattcttattaatgatcat aggataagaacatgagaaaaccatccatgttctctgttgtttttc ccatcaatctggccaccctctttcctcttttatgtagagatgatt tcaacagagtttgttttgtagttgtaatacttgtactcacagtt actgttttgcattcatcccatcagatgtcgaagaagcagattaa caagaacgtcagtatgatgtttcagtgaatatatggttgtaact tgtaaccaaacaaaagaaatgagactttgaccaaagattttgtc acaaaaaaaaaaa N. tabacum putative XylT
(GenBank AJ627182; SEQ ID NO: 75)
agtcagagagagaagaagatgaacaagaaaaagctgaaatttct tgtttctctcttcgctctcaactcaatcactctctatctctact tctcttcccactctgatcacttccgtcacaaatcccccaaaac cactttcctaatacccaaaaccactattccctgtcggaaaacca ccatgataatttccactcttctgtcacttcccaatataccaagc cttggccaattttgccctcctacctcccctggtctcagaatcct aatgtttctttgagatcgtgcgagggttacttcggtaatgggtt tactctcaaagttgatcttctcaaaacttcgccggagcttcacc agaaattcggcgaaacaccgtatccggcgacggcggatggttt aggtgttttttcagtgagactttgcagagttcgatttgcgaggg aggtgctatacgaatgaatccggacgagattttgatgtctcgtg gaggcgagaaattggagtcggttattggtaggagtgaagatgat gagctgcccgtgttcaaaaatggagcttttcagattaaagttac tgataaactgaaaattgggaaaaaattagtggatgaaaaaatct tgaataaatacttaccggaaggtgcaatttcaaggcacactatg cgtgaattaattgactctattcagttagttggcgccgatgaatt tcactgttctgagtggattgaggagccgtcacttttgattacac gatttgagtatgcaaaccttttccacacagttaccgattggtat agtgcatacgtggcatccagggttactggcttgcccagtcggcc acatttggttttttgtagatggccattgtgagacacaattggagg TABLE 4-continued Representative XylT and FucT sequences aaacatggaaagcactcttttcaagcctcacttatgctaagaac
tttagtggcccagtttgtttccgtcacgccgttctctcgcattg
ggatatgaaactgccctgtttaagggactgacagaaactataga
ttgtaatggagcttctgcccatgatttgtggcaaaatcctgatg
ataagagaactgcacggttgtctgagtttggggagatgatcagg
gcagcctttggatttcctgtggatagacagaacatcccaaggac
agtcacaggccctaatgtcctctttgttagacgtgaggattatt
tagctcacccacgtcatggtggaaaggtacagtctaggcttagc
aatgaagagcaagtatttgattccataaagagctgggccttgaa
ccactcggagtgcaaattaaatgtaattaacggattgtttgccc
acatgtccatgaaagagcaagttcgagcaatccaagatgcttct
gtcatagttggtgctcatggagcaggtctaactcacatagtttc
tgcagcaccaaaagctgtaatactagaaattataagcagcgaat
ataggcgcccccattttgctctgattgcacaatggaaaggattg
gagtaccatcccatatatttggaggggtcttatgcggatcctcc
agttgtgatcgacaggctcagcagcattttgaggagtcttgggt
gctaagtccgctcgacagtttgaatagttcggcttttctctaaa
agacggggaaggatagaggaattcggggttctggaacttggagc
ctgggaattttgataaatatgtttcacacgcagttctgtagtca
atggttgcaatctaggtcctcaatctggtgttgataagcttggc
aatttccagcagctactaatttattagcccgctctgactcggtt
atggactaccagagcaatcatatcaaatggaagcatggaatcct
gattgtggaatggtgagctcattgaagagcatattctttatggt
gttgaagattacaattcacaattaacacgtgtatgtgaaagatt
aggttggtacacttacttacaattcattgtcaattgttttcat
tattctcattaatgatcataggataagaacatgagaaaaccatc
catgttctgtgttgttttcccatcaatccggccaccctcttccc
tccttatgtagagatgatttcaacagagtttgttttgtagttgt
aacacttgcactcccagttacagttttgcattcgacacattcat
cccatcagatgtcaagtttaaaggcataagacatttgacatatt
gaagaagcagattaacacgaacgtcagtatgatgcttcagtgaa
gatatggttgtaacttgtaaccaaacaaaagaaatgagactttg
acaaaaaaaaaaaaaaaaaaaaaaaaa

*N. benthamiana* FucT1
(GenBank EF562630.1; SEQ ID NO: 76)
atgagatcggcgtcaaattcaaacgcacccaataagcaatggcg
caattggttgcctctgttcgttgccctagtgattatagctgagt
tttcttttctggttcgactcgacgtagctgaaaaagccaactct
tgggccgaatcgttttatcagttcaccacggcctcttggtccac
ctctaaactggctgttgaccacggcgacgttgaggaggtccagt tgggtgttttgagtggtgagttcgatcatggcttcgtacctggg
agttgcgaggagtggttggaaagggaagattctgtggcttattc
gagggattttgataatgaaccaattttttgttcatgggcctggac
aggaattgaaatcttgttccataggatgtaagtttggaacagat
tccaataagaagcctgatgcagcatttcggctaccacaacaagc
tggcacagctagtgtgctacggtcgatggagtcagctcaatact
atgcagagaacaacattactttggcacgacgaaggggatatgat
gttgtaatgacaacaagcctctcttcagatgttcctgttggata
cttctcttgggctgagtatgatatcatggctccagtagaaccta
aaacagagaatgccttggcagcggctttcatttctaattgtggt
gctcgcaacttccgtttgcaagctttagaagcccttgaaagggc
aaatatcagaattgactcttatggaagttgtcatcataacaggg
atggaagagttgacaaagtggcagcactgaagcgttaccagttt
agcttggcttttgagaattctaatgaggaggactatgtaactga
aaaattcttcagtctctggtagctgggtcaatccctgtggtgg
ttggtgctccaaacatccaagactttgcgccttctcctaattca
gttttacacattaaagagataaaagatgctgaatcaattgccaa
taccatgaagtaccttgctcaaaaccctattgcatataatgagt
cattaaggtggaagtttgagggcccatctgatgccttcaaagcc
cttgttgatatggcagcagttcattcatcttgtcgtttgtgcat
cttcttggcaagtaggatccgggaaagaagagcagagtccaa
aatttatgaagcgtccctgcaaatgtaccagagggactgaaact
gtatatcatgtatatgtaggtgaaagaggcaggtttgagatgga
ttccattttcttaaggtcgagtgatttgtctttgaaggcgtttg
aatctgctatcctctcgaggttcaagtctgttaaacatgttcct
gtttggaaggaggaaagacctcaagtactacgaggtggtgatga
actcaaactttacaaagtatatcctgttggcttgacacagagac
aagcattgttttccttcagattcaacggggatactgagtttaac
aattacattcaaagccacccatgtgcaaaatttgaagccatctt
cgtatag

*N. benthamiana* FucT
(pseudogene, GenBank EF562631.1; SEQ ID NO: 77)
atgagatcgtcgtcaaattcaaacgcacccgataaacaatggcg
caattggttgcctctgttcgttgccctagttgttatagcagaaa
tttcttttctggttcgactcgacgtggctgaaaaagccaactct
tgggctgagtcgttttatcagttcaccacggcgtcttggtcaac
ctccaaactggctgttgacggcggcgatgttgatgaggtcctgt
tgggtgttttgagtggtgagttgatcagggcttcctaccttgg
agttgcgaggagtggttggaaagggaagattatgtggcttattc
gagggattttgataatgaaccaattttttgttcatgggcctggac TABLE 4-continued Representative XylT and FucT sequences aggaattgaaatcttgttccataggatgtaagtttggaacagat
tccaataagaagcctgatgcagcatttcggctaccacaacaagc
tggcacagctagtgtgctacggtcgatggagtcagctcaatact
atgcagagaacaacattactttggcacgacgaaggggatatgat
gttgtaatgacaacaagcctacttcagatgttcctgttggatac
ttctcttgggctgagtatgatatcatggctccagtagaacctaa
aacagagaatgccttggcagcggcttttcatttctaattgtggtg
ctcgcaacttccgtttgcaagcttagaagcccttgaaagggca
aatatcagaattgactcttatggaagttgtcatcataacaggga
tggaagagtagacaaagtggcagcactgaagcgttacaagttta
gcttggcttttgagaattctaatgaggaggactatgtaaccgaa
aaattctttcagtctctggtagctgggtcaatccctgtggtggt
tggtgctccaaacatccaagactttgcgccttctcctaattcag
ttttacacattaaagagataaaagatgctgaattaattgccaat
accatgacgtaccttgctcaaaaccctattgcatctaatgagtc
attaaggtggaagtttgagggcccatttgatgccttcaaagccc
tggttgatatggcagcagttcattcatcttgccgtttgtgcatc
ttcttggcaagtaggatccaggaaagagaagagcatagtccaaa
atttacgaagcgccctgcaaatgtaccagagagactgaaactg
tctatcatgtatatgtacgtgaaagagggaggtttgagatggat
tccatttttcttaaggtcgagtgatttgtctttaaaggcgtttga
atctgctattctctcgaggttcaagtctgttaaacatgttcctg
tttggagggaggaaagacctcaagtactacgaggtggtgatgaa
ctcaaactttactaagtatatcctgttggcttgacacagagaca
agcattgttttccttcagattcaacggggatactgagtttaaga
attacattcaaagccacccatgtgcaaaatttgaagccatcttc
gtatag

*N. tabacum* FucT
(GenBank AB498916.1; SEQ ID NO: 78)
aacccccccccccccaccccccaactgtcccaccaaatgaaga
attcccaaaccctctgaagaagaagaaaaaaagatcacatcttt
agctatttacttccacaaaaagaacaaaatttcgagttattaa
tggcaacagttattccaattcaaaggttaccaagatttgaaggt
gttgggtcatcatcacctacaaacgttcccccttaagaaatggtc
caattggctacctctagtagttgcacttgtggttatagttgaaa
ttacatttctgggtcgactggacatggctgaaaaagccaacctg
gtcaactcttggactgactcatttttaccagtttacgacgtcgtc
ttggtcaacctccaaagtggaaattagtgagactgggttgggtg
tgttgagagtagtgaggttgatcggaatttggaaactgggagc
tgtgaggagtggttggaaaaggaggattctgtggagtattctag TABLE 4-continued Representative XylT and FucT sequences agattttgacaaagacccaatttttgttcatggcggcgaaaagg
attggaagtcttgtgccgtaggatgtaactttggtgtggattct
gaaaagaagcctgatgcggcatttgggacaccacaacaggctgg
cacggctagcgtgcttcggtcaatggagtcagctcaatactatc
ctgagaacaacatcgttatggcacgacgaaggggatatgatatt
gtaatgacaacaagcctctcttcggatgttcctgttgggtactt
ctcttgggcggagtatgatataatggctccagtgcaacctaaaa
ctgagaatgcgttagcagctgcttttatttctaattgtggtgct
cgcaacttccggttacaggctcttgaagtccttgaaagggcaaa
tatcaagattgattcttttggcagttgtcatcgtaaccgggatg
gaaatgtggacaaagtggaaactctcaagcgctataaatttagc
ttcgcttttgagaattctaatgaggaggattatgtcaccgaaaa
attcttccagtctctggtagctggatcagtccctgtggtgattg
gtgctccaaacatcctagactttgctccttctcctaattcactt
ttacacattaaagagctgaaagacgctgcatcagttgccgagac
tatgaagtaccttgcagaaaatcctagtgcatataatgagtcat
taaggtggaagcttgacggtccatctgactcttttcaaagccctg
gttgacatggcagcagttcactatatgtcgtttgtgtatatata
gcaactagtattagggagaaagaagagaagagtccagaatttac
aaaacgtccctgcaaatgtaccagaggttcagaaactgtctatc
atatatatgtacgtgaaagagggaggtttgacatggagtccatt
ttcctaaggtcatctaatttgtcattggaggcttttgaatctgc
agtactgtcgaagttcaaatctttaaagcatgttcccatttgga
agaagaaagacctcaaatactacgcggaggggatgaactaaag
ctctacagggtatatcctctcggcatgacacaacgacaggcatt
gtacacctccagattcaaaggagacgccgattttaggaatcaca
tcgaaagccacccatgtgcaaaattttgaagccatatttgtatag
atcaagtccaaacctgagagtctcgacagcagcttgttgtaggc
catagcgtaatgctcattcttactctatgccccactgtctaaca
tcattctggttatgaattcgtcgtgtagagtaaggatttgatta
ttacatggggccaacctaatttttgggtggaaagtactgatctttt
tacatttacaagtaagaaggaacaaactctgaaccttgaatgga
catgcctaacctcccaaagttgtgcagttgggaaattgcgggtg
atatacaaacttggacttggttttgctagcagaaaaattctagct
gatcaatttgtaatctagttcagaggacatctccatcgtgttac
aagtaatgacaagtgcagaaactaattaaaggttcttttcggaa
aaaaaaaaaaaa

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for making a *Nicotiana benthamiana* plant that comprises a mutation in each of a plurality of XylT1 and XylT2 alleles and a mutation in each of a plurality of FucT1 and FucT2 alleles, said method comprising:
   (a) contacting a population of *Nicotiana benthamiana* plant cells comprising functional XylT1 and XylT2 alleles and functional FucT1 and FucT2 alleles with a single TAL effector endonuclease that binds to a first pair of nucleic acid sequences selected from the group consisting SEQ ID NOs: 47 and 48, SEQ ID NOs: 49 and 50, and SEQ ID NOs: 51 and 52, each of said first pair of nucleic acid sequences located in the plurality of XylT1 and XylT2 alleles, and a second TAL effector endonuclease that binds to a second pair of nucleic acid sequences selected from the group consisting SEQ ID NOs: 53 and 54, SEQ ID NOs: 55 and 56, SEQ ID NOs: 57 and 58, SEQ ID NOs: 58 and 59, and SEQ ID NOs: 62 and 63, each of said second pair of nucleic acid sequences located in the plurality of FucT1 and FucT2 alleles, wherein said *Nicotiana benthamiana* plant cells are protoplasts,
   (b) selecting, from said population, a cell in which each of said plurality of XylT1 and XylT2 alleles and each of said plurality of FucT1 and FucT2 alleles have been inactivated, and
   (c) regenerating said selected plant cell into athe *Nicotiana benthamiana* plant, wherein said selected *Nicotiana benthamiana* plant does not produce detectable levels of beta-1,2-xylosyl-sugars and produces reduced levels of core alpha-1,3-fucosyl-sugars on N-glycan structures of glycoproteins compared to a corresponding plant that does not contain said mutations.

2. The method of claim 1, comprising isolating genomic DNA comprising at least a portion of a XylT locus or at least a portion of a FucT locus from said protoplasts.

3. A method for making a *Nicotiana benthamiana* plant that comprises a mutation in one or more XylT1 and XylT2 alleles and a mutation in one or more FucT1 and FucT2 alleles, said method comprising:
   (a) contacting a population of *Nicotiana benthamiana* plant cells comprising functional XylT1 and XylT2 alleles and functional FucT1 and FucT2 alleles with a first TAL effector endonuclease that binds to a first pair of nucleic acid sequences selected from the group consisting SEQ ID NOs: 47 and 48, SEQ ID NOs: 49 and 50, and SEQ ID NOs: 51 and 52, each of said first pair of nucleic acid sequences located in the plurality of XylT1 and XylT2 alleles, and a second TAL effector endonuclease that binds to a second pair of nucleic acid sequences selected from the group consisting SEQ ID NOs: 53 and 54, SEQ ID NOs: 55 and 56, SEQ ID NOs: 57 and 58, SEQ ID NOs: 58 and 59, and SEQ ID NOs: 62 and 63, each of said second pair of nucleic acid sequences located in the plurality of FucT1 and FucT2 alleles,
   (b) selecting, from said population, a cell in which one or more XylT1 and XylT2 alleles and one or more FucT1 and FucT2 alleles have been inactivated, and
   (c) regenerating said selected plant cell into the *Nicotiana benthamiana* plant, wherein the levels of beta-1,2-xylosyl- and core alpha-1,3-fucosyl-sugars on N-glycan structures of glycoproteins produced in said plant are decreased as compared to a corresponding plant that does not contain said mutations.

4. The method of claim 3, comprising transforming said protoplasts with one or more vectors encoding said TAL effector endonucleases.

5. The method of claim 3, comprising introducing into said protoplasts a nucleic acid encoding a TAL effector endonuclease protein.

6. The method of claim 1, wherein said *Nicotiana benthamiana* plant comprises a deletion in each XylT1 and XylT2 allele and a deletion in each FucT1 and FucT2 allele.

7. The method of claim 1, wherein said first TAL effector endonuclease binds to SEQ ID NOS:51 and 52, and wherein said second TAL effector endonuclease binds to SEQ ID NOS:58 and 59.

8. The method of claim 3, wherein said first TAL effector endonuclease binds to SEQ ID NOS:51 and 52, and wherein said second TAL effector endonuclease binds to SEQ ID NOS:58 and 59.

* * * * *

```
                            SEQUENCE LISTING

<160> NUMBER OF SEQ ID NOS: 101

<210> SEQ ID NO 1
<211> LENGTH: 90
<212> TYPE: DNA
<213> ORGANISM: Nicotiana benthamiana

<400> SEQUENCE: 1
atgaacaaga aaaagctgaa aattcttgtt tctctcttcg ctctcaactc aatcactctc     60
tatctctact tctcttccca ccctgatcac                                      90

<210> SEQ ID NO 2
<211> LENGTH: 130
<212> TYPE: DNA
<213> ORGANISM: Nicotiana benthamiana

<400> SEQUENCE: 2
atgagatcgg cgtcaaattc aaacgcaccc aataagcaat ggcgcaattg gttgcctctg     60
ttcgttgccc tagtgattat agctgagttt tcttttctgg ttcgactcga cgtagctgaa    120
aaagccaact                                                           130

<210> SEQ ID NO 3
<211> LENGTH: 130
<212> TYPE: DNA
<213> ORGANISM: Nicotiana benthamiana

<400> SEQUENCE: 3
atgagatcgt cgtcaaattc aaacgcaccc gataaacaat ggcgcaattg gttgcctctg     60
ttcgttgccc tagttgttat agcagaaatt tcttttctgg ttcgactcga cgtggctgaa    120
aaagccaact                                                           130

<210> SEQ ID NO 4
<211> LENGTH: 58
<212> TYPE: DNA
<213> ORGANISM: Nicotiana benthamiana

<400> SEQUENCE: 4
gtttctctct tcgctctcaa ctcaatcact ctctatctct acttctcttc ccaccctg       58

<210> SEQ ID NO 5
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 5
gtttctctct tcgctctcaa ctcaatctct atctctactt ctcttcccac cctg            54

<210> SEQ ID NO 6
<211> LENGTH: 51
<212> TYPE: DNA
<213> ORGANISM: Artificial Sequence
<220> FEATURE:
<223> OTHER INFORMATION: synthetic oligonucleotide
```

<400> SEQUENCE: 6
gtttctctct tcgctctcaa ctcatctatc tctacttctc ttcccaccct g    51

<210> SEQ ID NO 7
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 7
gtttctctct tcgctctcaa ctctctatct ctacttctct tcccaccctg    50

<210> SEQ ID NO 8
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 8
gtttctctct tcgctctcaa ctcaatctct acttctcttc ccaccctg    48

<210> SEQ ID NO 9
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 9
gtttctctct tcgctctcaa ctcctacttc tcttcccacc ctg    43

<210> SEQ ID NO 10
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 10
gtttctctct tcgctctcaa tctacttctc ttcccaccct g    41

<210> SEQ ID NO 11
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 11
gtttctcctc tatctctact tctcttccca ccctg    35

<210> SEQ ID NO 12
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 12
gttctctatc tctacttctc ttcccaccct g    31

<210> SEQ ID NO 13
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 13
gtttctctct tcgcaccctg                                              20

<210> SEQ ID NO 14
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 14
gtttctctct tcgctctg                                                18

<210> SEQ ID NO 15
<211> LENGTH: 48
<212> TYPE: DNA
<213> ORGANISM: Artificial Sequence
<220> FEATURE:
<223> OTHER INFORMATION: synthetic oligonucleotide

<400> SEQUENCE: 15
gtttctctct tcgctctcat gtctatctct acttctcttc ccaccctg               48

<210> SEQ ID NO 16
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 16
gtttctctct tcgctctcct ctatctctac ttctcttccc accctg                 46

<210> SEQ ID NO 17
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 17
gtttctctct tcgctctcta tctctacttc tcttcccacc ctg                    43

<210> SEQ ID NO 18
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 18
gtttctctct tcctatctct acttctcttc ccaccctg                          38

<210> SEQ ID NO 19
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 19
```

```
gtttctctct tcgctctctt cccaccctg                                29
```

<210> SEQ ID NO 20
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 20

```
gatctctact tctcttccca ccctg                                    25
```

<210> SEQ ID NO 21
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 21

```
tctatctcta cttctcttcc caccctg                                  27
```

<210> SEQ ID NO 22
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 22

```
gtttctcttc ccaccctg                                            18
```

<210> SEQ ID NO 23
<211> LENGTH: 65
<212> TYPE: DNA
<213> ORGANISM: Nicotiana benthamiana

<400> SEQUENCE: 23

```
tcaaattcaa acgcacccaa taagcaatgg cgcaattggt tgcctctgtt cgttgcccta    60
gtgat                                                               65
```

<210> SEQ ID NO 24
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 24

```
tcaaattcaa acgcacccaa taagcaatgg cgcggttgcc tctgttcgtt gccctagtga    60
t                                                                   61
```

<210> SEQ ID NO 25
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 25

```
tcaaattcaa acgcacccaa taagcaatgc ctctgttcgt tgccctagtg at             52
```

<210> SEQ ID NO 26
<211> LENGTH: 51

<212> TYPE: DNA
<213> ORGANISM: Artificial Sequence
<220> FEATURE:
<223> OTHER INFORMATION: synthetic oligonucleotide

<400> SEQUENCE: 26
tcaaattcaa acgcacccaa taagcaatcc tctgttcgtt gccctagtga t          51

<210> SEQ ID NO 27
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 27
tcaaattcaa acgcacccaa ttgcctctgt tcgttgccct agtgat               46

<210> SEQ ID NO 28
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 28
tcaaattcaa acgcacccaa taactgttcg ttgccctagt gat                  43

<210> SEQ ID NO 29
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 29
tcaaattcaa acgcacccaa taagttcgtt gccctagtga t                    41

<210> SEQ ID NO 30
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 30
tcaaattcaa acgcacccaa taagcattgc cctagtgat                       39

<210> SEQ ID NO 31
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 31
tcaaattcaa acgcacccaa tcgttgccct agtgat                          36

<210> SEQ ID NO 32
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 32
tcaaattcaa acgcaccgcc ctagtgat                                28

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
tcaaattcaa acgcacccaa ta                                      22

<210> SEQ ID NO 34
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 34
tcaaattcaa acgcacccga taaacaatgg cgcaattggt tgcctctgtt cgttgcccta     60
gttgt                                                         65

<210> SEQ ID NO 35
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 35
tcaaattcaa acgcacccga taaacaatgg cgttgcctct gttcgttgcc ctagttgt      58

<210> SEQ ID NO 36
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 36
tcaaattcaa acgcacccga taaacaggtt gcctctgttc gttgccctag ttgt           54

<210> SEQ ID NO 37
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 37
tcaaattcaa acgcacccga tttggttgcc tctgttcgtt gccctagttg t              51

<210> SEQ ID NO 38
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 38
tcaaattcaa acgcacccga taaacctctg ttcgttgccc tagttgt                  47

<210> SEQ ID NO 39
<211> LENGTH: 45

```
<212> TYPE: DNA
<213> ORGANISM: Artificial Sequence
<220> FEATURE:
<223> OTHER INFORMATION: synthetic oligonucleotide

<400> SEQUENCE: 39
tcaaattcaa acgcacccga taactctgtt cgttgcccta gttgt          45

<210> SEQ ID NO 40
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 40
tcaaattcaa acgcacccga ttctgttcgt tgccctagtt gt             42

<210> SEQ ID NO 41
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 41
tcaaattcaa acgcattgcc tctgttcgtt gccctagttg t              41

<210> SEQ ID NO 42
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 42
tcaaattcaa acgcacccga taaacaatgc cctagttgt                 39

<210> SEQ ID NO 43
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 43
tcaaattcaa acgcacccga taaacgccct agttgt                    36

<210> SEQ ID NO 44
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 44
tcaaattcaa acgcaccctá gttgt                                25

<210> SEQ ID NO 45
<211> LENGTH: 17
<212> TYPE: DNA
<213> ORGANISM: Nicotiana benthamiana

<400> SEQUENCE: 45
tgaacaagaa aaagctg                                         17
```

<210> SEQ ID NO 46
<211> LENGTH: 17
<212> TYPE: DNA
<213> ORGANISM: Nicotiana benthamiana

<400> SEQUENCE: 46
tcttcgctct caactca                                                    17

<210> SEQ ID NO 47
<211> LENGTH: 17
<212> TYPE: DNA
<213> ORGANISM: Nicotiana benthamiana

<400> SEQUENCE: 47
tgaaaattct tgtttct                                                    17

<210> SEQ ID NO 48
<211> LENGTH: 17
<212> TYPE: DNA
<213> ORGANISM: Nicotiana benthamiana

<400> SEQUENCE: 48
aactcaatca ctctcta                                                    17

<210> SEQ ID NO 49
<211> LENGTH: 17
<212> TYPE: DNA
<213> ORGANISM: Nicotiana benthamiana

<400> SEQUENCE: 49
ttcttgtttc tctcttc                                                    17

<210> SEQ ID NO 50
<211> LENGTH: 17
<212> TYPE: DNA
<213> ORGANISM: Nicotiana benthamiana

<400> SEQUENCE: 50
atcactctct atctcta                                                    17

<210> SEQ ID NO 51
<211> LENGTH: 17
<212> TYPE: DNA
<213> ORGANISM: Nicotiana benthamiana

<400> SEQUENCE: 51
tctcttcgct ctcaact                                                    17

<210> SEQ ID NO 52
<211> LENGTH: 17
<212> TYPE: DNA
<213> ORGANISM: Nicotiana benthamiana

<400> SEQUENCE: 52
ctctacttct cttccca                                                    17

<210> SEQ ID NO 53
<211> LENGTH: 17
<212> TYPE: DNA
<213> ORGANISM: Nicotiana benthamiana

<400> SEQUENCE: 53
tgagatcggc gtcaaat                                                    17

```
<210> SEQ ID NO 54
<211> LENGTH: 17
<212> TYPE: DNA
<213> ORGANISM: Nicotiana benthamiana

<400> SEQUENCE: 54
aataagcaat ggcgcaa                                                    17

<210> SEQ ID NO 55
<211> LENGTH: 17
<212> TYPE: DNA
<213> ORGANISM: Nicotiana benthamiana

<400> SEQUENCE: 55
tgagatcgtc gtcaaat                                                    17

<210> SEQ ID NO 56
<211> LENGTH: 17
<212> TYPE: DNA
<213> ORGANISM: Nicotiana benthamiana

<400> SEQUENCE: 56
gataaacaat ggcgcaa                                                    17

<210> SEQ ID NO 57
<211> LENGTH: 17
<212> TYPE: DNA
<213> ORGANISM: Nicotiana benthamiana

<400> SEQUENCE: 57
ttcaaacgca cccaata                                                    17

<210> SEQ ID NO 58
<211> LENGTH: 17
<212> TYPE: DNA
<213> ORGANISM: Nicotiana benthamiana

<400> SEQUENCE: 58
ctctgttcgt tgccta                                                     17

<210> SEQ ID NO 59
<211> LENGTH: 17
<212> TYPE: DNA
<213> ORGANISM: Nicotiana benthamiana

<400> SEQUENCE: 59
ttcaaacgca cccgata                                                    17

<210> SEQ ID NO 60
<211> LENGTH: 17
<212> TYPE: DNA
<213> ORGANISM: Nicotiana benthamiana

<400> SEQUENCE: 60
tctgttcgtt gccctag                                                    17

<210> SEQ ID NO 61
<211> LENGTH: 17
<212> TYPE: DNA
<213> ORGANISM: Nicotiana benthamiana

<400> SEQUENCE: 61
```

```
tttcttttct ggttcga                                              17

<210> SEQ ID NO 62
<211> LENGTH: 17
<212> TYPE: DNA
<213> ORGANISM: Nicotiana benthamiana

<400> SEQUENCE: 62
ttgcctctgt tcgttgc                                              17

<210> SEQ ID NO 63
<211> LENGTH: 17
<212> TYPE: DNA
<213> ORGANISM: Nicotiana benthamiana

<400> SEQUENCE: 63
tttctggttc gactcga                                              17

<210> SEQ ID NO 64
<211> LENGTH: 46
<212> TYPE: DNA
<213> ORGANISM: Nicotiana benthamiana

<400> SEQUENCE: 64
ttcttgtttc tctcttcgct ctcaactcaa tcactctcta tctcta              46

<210> SEQ ID NO 65
<211> LENGTH: 48
<212> TYPE: DNA
<213> ORGANISM: Nicotiana benthamiana

<400> SEQUENCE: 65
tctcttcgct ctcaactcaa tcactctcta tctctacttc tcttccca            48

<210> SEQ ID NO 66
<211> LENGTH: 46
<212> TYPE: DNA
<213> ORGANISM: Nicotiana benthamiana

<400> SEQUENCE: 66
tgagatcggc gtcaaattca aacgcaccca ctaagcaatg gcgcaa               46

<210> SEQ ID NO 67
<211> LENGTH: 46
<212> TYPE: DNA
<213> ORGANISM: Nicotiana benthamiana

<400> SEQUENCE: 67
tgagatcgtc gtcaaattca aacgcacccg ataaacaatg gcgcaa               46

<210> SEQ ID NO 68
<211> LENGTH: 55
<212> TYPE: DNA
<213> ORGANISM: Nicotiana benthamiana

<400> SEQUENCE: 68
ttcaaacgca cccaataagc aatggcgcaa ttggttgcct ctgttcgttg cccta     55

<210> SEQ ID NO 69
<211> LENGTH: 55
<212> TYPE: DNA
<213> ORGANISM: Nicotiana benthamiana

<400> SEQUENCE: 69
```

-continued ttcaaacgca cccgataaac aatggcgcaa ttggttgcct ctgttcgttg cccta    55

<210> SEQ ID NO 70
<211> LENGTH: 59
<212> TYPE: DNA
<213> ORGANISM: Nicotiana benthamiana

<400> SEQUENCE: 70
ttgcctctgt tcgttgccct agtgattata gctgagtttt cttttctggt tcgactcga    59

<210> SEQ ID NO 71
<211> LENGTH: 59
<212> TYPE: DNA
<213> ORGANISM: Nicotiana benthamiana

<400> SEQUENCE: 71
ttgcctctgt tcgttgccct agttgttata gcagaaattt cttttctggt tcgactcga    59

<210> SEQ ID NO 72
<211> LENGTH: 1887
<212> TYPE: DNA
<213> ORGANISM: Nicotiana benthamiana

<400> SEQUENCE: 72
gatccagaaa agcactgaac gttgtttaac cctctgtagt ctactctgta ctaagtagta    60
cacacgaaaa cagccagtcg gagagagaag aagatgaaca agaaaaagct gaaaattctt   120
gtttctctct tcgctctcaa ctcaatcact ctctatctct acttctcttc ccaccctgat   180
cacaaatccc cccaaaacca cttttccttg tcggaaaacc accatcataa tttccactct   240
tcaatcactt ctcaatattc caagccttgg cctattttgc cctcctacct cccttggtct   300
caaaaccta atgttgcttg gagatcgtgc gagggttact tcggtaatgg gtttactctc   360
aaagttgacc ttctcaaaac ttcgccggag tttcaccgga aattcggcga taacaccgtc   420
tccggtgacg gcggatggtt taggtgtttt ttcagtgaga ctttgcagag ttcgatctgc   480
gagggaggcg caatacgaat gaatccggac gatattttga tgtctcgtgg aggtgagaaa   540
ttggagtcgg ttattggtag gaatgaagat gatgagctgc ccatgttcaa aaatggagct   600
ttccaaattg aagttactga taaactgaaa attgggaaaa aactagtgga taaaaaattc   660
ttgaataaat acttaccggg aggtgcgatt tcaaggcaca ctatgcgtga gttaattgac   720
tctattcagt tggttggcgc cgatgaattt cactgttctg agtgggttga ggagccgtca   780
cttttgatta cacgatttga gtatgcaaac cttttccaca cagttaccga ttggtatagt   840
gcatacgcgg catccagggt tactggtttg cccagtcggc caaatttggt ttttgtagat   900
ggccattgtg agacacaatt ggaggaaaca tggaaagcac ttttttcaag cctcacttat   960
gctaagaact ttagtggccc agtttgtttc cgtcatgctg tcctctcgcc tttaggatat  1020
gaaactgccc tgtttaaggg actgtcagaa actatagatt gtaatggagc ttctgctcat  1080
gatttgtggc aaaagcctga tgataaaaaa actgcacggt tgtccgagtt tggggagatg  1140
atcagggcag cctttggatt tcctgtggat agacagaaca tcccaaggac agtcacaggc  1200
cctaatgtcc tcttttgttag acgtgaggat tatttagctc acccacgtca tggtggaaag  1260
gtacagtcta ggcttagcaa tgaagagcta gtatttgatt ccataaagag ctgggccttg  1320
aaccactcgg agtgtaaatt aaatgtaatt aacggattgt tgcccacat gtccatgaaa  1380
gagcaagttc gagcaatcca agatgcttct gtcattgttg gtgctcatgg agcaggtcta  1440

```
actcacatag tttctgcagc accaaaagct gtaatactag aaattataag cagcgaatat   1500
aggcgccccc attttgctct gattgcacaa tggaaaggat tggagtacca tcccatatat   1560
ttggaggggt cttatgcgga tcctccagtt gtgatcgaca agctcagcag catttttgagg  1620 agtcttgggt gctaaatctg ctcgacagtt tagttcggct tttctctaaa agattgggaa   1680
ggatagagga attcggggtt ctggaacttg gagcctggga attgtgtaaa atatgtttca   1740
cacgcagttc tatagtcaat tgctgcaatc tggtgttcat aagcttggaa atttccagca   1800
gctactaact tattagccca ctctgactca gttatggact accagagagc aattcacaag   1860
taacacgtgt atgtgaaagc ttccatt                                      1887
```

<210> SEQ ID NO 73
<211> LENGTH: 2072
<212> TYPE: DNA
<213> ORGANISM: Nicotiana benthamiana

<400> SEQUENCE: 73

```
agtacagacg aaacagccc gtgagagaga gagagagagg agaagaagat gaacaagaaa    60
aagctgaaaa ttcttgtttc tctcttcgct ctcaactcaa tcactctcta tctctacttc   120
tcttcccacc ctgatcactc tcgtcgcaaa tccccccaga accacttttc ctcgtcggaa   180
aaccaccatc ataatttcca ctcttcaatc acttcccaat attccaggcc ttggcctatt   240
ttgccctcct acctcccttg gtctcaaaac cctaatgttg cttggagatc atgcgagggt   300
tacttcggta atggttttac tctcaaagtt gatcttctca aaacttcgcc ggagcttcac   360
cggaaattcg gcgaaaacac cgtcttcgga dcggcggat ggtttaggtg tttcttcagt    420
gagactttgc agagttcgat ctgcgaggga ggcgcaatac gaatgaatcc agacgagatt   480
ttgatgtctc gtggaggtga aaattggag tcggttattg gtaggagtga agatgatgag    540
gtgcccgcgt tcaaaactgg agcttttcag attaaagtta ctgataaact gaaatttggg   600
aaaaaattag tggatgaaaa cttcttgaat aaatacttac cggaaggtgc aatttcaagg   660
cacactatgc gtgagttaat cgactctatt cagttggttg gcgccaatga ttttcactgt   720
tctgagtgga ttgaggagcc gtcactttg attacacgat ttgagtatgc aaacctttt    780 cacacaatta ccgattggta tagtgcatac gtggcatcga gggttactgg cttgcccagt   840
cggccacatt tggttttgt agatggccat tgtgagacac aattggagga acatgaaa     900 gcacttttt caagcctcac ttatgctaag aactttagtg gcccagtttg tttccgtcat   960
gccgtcctct cgccttggg atatgaaact gccctgttta agggactgtc agaaactata   1020
gattgtaatg gagcttctgc tcatgatttg tggcaaaatc ctgatgataa gaaaactgca   1080
cggttatccg agtttgggga gatgatcagg gcagcctttg gatttcctgt tgatagacag   1140
aacatcccaa ggacagtcac aggccctaat gtcctctttg ttagacgtga ggattattta   1200
gctcacccac gtcatggtgg aaaggtacag tctaggctta gcaatgaaga gcaagtattt   1260
gattccataa agagctgggc cttaaaccac tcggagtgca aattaaatgt aattagtgga   1320
ttgtttgccc acatgtccat gaaagagcaa gttcgagcaa tccaagatgc ttctgtcatt   1380
gttggtgctc atggagcagg tctaacccac atagttctg cagcaccaaa agctgtaata   1440
ctagaaatta taagcagcga atataggcgc cccattttg ctctgattgc tcaatggaaa   1500
ggattggagt accatcccat atatttggag gggtcttatg cggatcctcc agttgtgatc   1560
gacaagctca gcagcatttt gaggagtctt gggtgctaaa tctgctcgac agtttgaata   1620
gattagtttt tgtctaaaag actgggaagg aaaaagagga gtttggggtt ctgcaacatg   1680
```

```
gagcatgaga attgtgtaaa atatgtttca cacgcagttc tatagtcaat tgctgcaatc    1740
tggtgtttat aagcttggaa atttccagca gctactaact tattagccca ctctgactca    1800
gttatggact accagagcaa tcatatcaaa tgggagcatg gaatcctgat tgtggaattg    1860
tgatctcatt gaagagcata ttctttaagg tgttgaagat tacagttgac cagtaacacg    1920
tgtatgtgaa agattaggtt gttacacttt cttgcaattc attgtcaatt tttttattaa    1980
tggtcatagg ataagaacat gagaaaacca tccatgttct gtgttgtttt cccatcaatc    2040
tggccaccct ctttcctcct tatgttgaga tg                                  2072

<210> SEQ ID NO 74
<211> LENGTH: 2260
<212> TYPE: DNA
<213> ORGANISM: Nicotiana tabacum

<400> SEQUENCE: 74
gtcagagaga gaagaagatg aacaagaaaa agctgaaatt tcttgtttct ctcttcgctc      60
tcaactcaat cactctctat ctctacttct cttcccactc tgatcacttc cgtcacaaat     120 cccccccaaaa ccactttcct aatacccaaa accactattc cctgtcggaa aaccaccatg    180
ataatttcca ctcttctgtc acttcccaat ataccaagcc ttggccaatt ttgccctcct    240
acctcccctg gtctcagaat cctaatgttt ctttgagatc gtgcgagggt tacttcggta    300
atgggtttac tctcaaagtt gatcttctca aaacttcgcc ggagcttcac cagaaattcg    360
gcgaaaacac cgtatccggc gacggcggat ggtttaggtg ttttttcagt gagactttgc    420
agagttcgat ttgcgaggga ggtgctatac gaatgaatcc ggacgagatt ttgatgtctc    480
gtggaggcga gaaattggag tcggttattg gtaggagtga agatgatgag ctgcccgtgt    540
tcaaaaatgg agcttttcag attaaagtta ctgataaact gaaaattggg aaaaaattag    600
tggatgaaaa aatcttgaat aaatacttac cggaaggtgc aatttcaagg cacactatgc    660
gtgaattaat tgactctatt cagttagttg gcgccgatga atttcactgt tctgagtgga    720
ttgaggagcc gtcacttttg attacacgat ttgagtatgc aaaccttttc cacacagtta    780
ccgattggta tagtgcatac gtggcatcca gggttactgg cttgcccagt cggccacatt    840 tggttttgt agatggccat tgtgagacac aattggagga acatggaaa gcactctttt     900 caagcctcac ttatgctaag aactttagtg gcccagtttg tttccgtcac gccgttctct    960
cgcctttggg atatgaaact gccctgttta agggactgac agaaactata gattgtaatg   1020
gagcttctgc ccatgatttg tggcaaaatc ctgatgataa gagaactgca cggttgtccg   1080
agtttgggga gatgatcagg gcagcctttg gatttcctgt ggatagacag aacatcccaa   1140
ggacagtcac aggccctaat gtcctctttg ttagacgtga ggattattta gctcacccac   1200
gtcatggtgg aaaggtacag tctaggctta gcaatgaaga gcaagtattt gattccataa   1260
agagctgggc cttgaaccac tcggagtgca aattaaatgt aattaacgga ttgtttgccc   1320
acatgtccat gaaagagcaa gttcgagcaa tccaagatgc ttctgtcata gttggtgctc   1380
atggagcagg tctaactcac atagtttctg cagcaccaaa agctgtaata ctagaaatta   1440
taagcagcga ataaggcgc ccccattttg ctctaattgc acaatggaaa ggattggagt   1500
accatcccat atatttggag gggtcttatg cggatcctcc agttgtgatc gacaagctca   1560
gcagcatttt gaggagtctt gggtgctaaa tctgctcgac agtttagttc gtcttttctc    1620
taaaagactg ggaaggatag aggaattcgg ggttctggaa cctggagcct gggaattgtg   1680
```

| | |
|---|---|
| taaaatatgt ttcacacgca gttctatagt caattgctgc aatctggtgt tcataagctt | 1740 |
| ggaaatttcc agcagctact aacttattag cccactctga ctcagttatg gactaccaga | 1800 |
| gcaatcatat caaatgggag catggaatcc tgattgtgga atggtgagct cattgaagag | 1860 |
| catattcttt atggtgttga agattacagt tgacgagtaa cacgtgtatg tgaaagatta | 1920 |
| ggttgttaca ctttcttgca attcattgtc aattgttttt cgtcattctt attaatgatc | 1980 |
| ataggataag aacatgagaa aaccatccat gttctctgtt gttttcccat caatctggcc | 2040 |
| accctctttc ctctttatgt agagatgatt tcaacagagt ttgttttgta gttgtaatac | 2100 |
| ttgtactcac agttactgtt ttgcattcat cccatcagat gtcgaagaag cagattaaca | 2160 |
| agaacgtcag tatgatgttt cagtgaatat atggttgtaa cttgtaacca aacaaaagaa | 2220 |
| atgagacttt gaccaaagat tttgtcacaa aaaaaaaaaa | 2260 |

<210> SEQ ID NO 75
<211> LENGTH: 2318
<212> TYPE: DNA
<213> ORGANISM: Nicotiana tabacum

<400> SEQUENCE: 75

| | |
|---|---|
| agtcagagag agaagaagat gaacaagaaa aagctgaaat ttcttgtttc tctcttcgct | 60 |
| ctcaactcaa tcactctcta tctctacttc tcttcccact ctgatcactt ccgtcacaaa | 120 |
| tcccccaaa accactttcc taatacccaa accactatt ccctgtcgga aaaccaccat | 180 |
| gataatttcc actcttctgt cacttcccaa tataccaagc cttggccaat tttgccctcc | 240 |
| tacctcccct ggtctcagaa tcctaatgtt tctttgagat cgtgcgaggg ttacttcggt | 300 |
| aatgggttta ctctcaaagt tgatcttctc aaaacttcgc cggagcttca ccagaaattc | 360 |
| ggcgaaaaca ccgtatccgg cgacggcgga tggtttaggt gttttttcag tgagactttg | 420 |
| cagagttcga tttgcgaggg aggtgctata cgaatgaatc cggacgagat tttgatgtct | 480 |
| cgtggaggcg agaaattgga gtcggttatt ggtaggagtg aagatgatga gctgcccgtg | 540 |
| ttcaaaaatg gagcttttca gattaaagtt actgataaac tgaaaattgg gaaaaaatta | 600 |
| gtggatgaaa aaatcttgaa taaatactta ccggaaggtg caatttcaag gcacactatg | 660 |
| cgtgaattaa ttgactctat tcagttagtt ggcgccgatg aatttcactg ttctgagtgg | 720 |
| attgaggagc cgtcactttt gattacacga tttgagtatg caaaccttttt ccacacagtt | 780 |
| accgattggt atagtgcata cgtggcatcc agggttactg gcttgcccag tcggccacat | 840 |
| ttggtttttg tagatggcca ttgtgagaca caattggagg aaacatggaa agcactcttt | 900 |
| tcaagcctca cttatgctaa gaactttagt ggcccagttt gtttccgtca cgccgttctc | 960 |
| tcgcctttgg gatatgaaac tgccctgttt aagggactga cagaaactat agattgtaat | 1020 |
| ggagcttctg cccatgattt gtggcaaaat cctgatgata agagaactgc acggttgtct | 1080 |
| gagtttgggg agatgatcag ggcagccttt ggatttcctg tggatagaca gaacatccca | 1140 |
| aggacagtca caggccctaa tgtcctcttt gttagacgtg aggattattt agctcaccca | 1200 |
| cgtcatggtg gaaaggtaca gtctaggctt agcaatgaag agcaagtatt tgattccata | 1260 |
| aagagctggg ccttgaacca ctcggagtgc aaattaaatg taattaacgg attgtttgcc | 1320 |
| cacatgtcca tgaaagagca agttcgagca atccaagatg cttctgtcat agttggtgct | 1380 |
| catggagcag gtctaactca catagttttct gcagcaccaa aagctgtaat actagaaatt | 1440 |
| ataagcagcg aatataggcg ccccccatttt gctctgattg cacaatggaa aggattggag | 1500 |
| taccatccca tatatttgga ggggtcttat gcggatcctc cagttgtgat cgacaggctc | 1560 |

```
agcagcattt tgaggagtct tgggtgctaa gtccgctcga cagtttgaat agttcggctt    1620
ttctctaaaa gacggggaag gatagaggaa ttcggggttc tggaacttgg agcctgggaa    1680
ttttgataaa tatgtttcac acgcagttct gtagtcaatg gttgcaatct aggtcctcaa    1740
tctggtgttg ataagcttgg caatttccag cagctactaa tttattagcc cgctctgact    1800
cggttatgga ctaccagagc aatcatatca aatggaagca tggaatcctg attgtggaat    1860
ggtgagctca ttgaagagca tattctttat ggtgttgaag attacaattc acaattaaca    1920
cgtgtatgtg aaagattagg ttggtacact tacttacaat tcattgtcaa ttgttttttca    1980 ttattctcat taatgatcat aggataagaa catgagaaaa ccatccatgt tctgtgttgt    2040
tttcccatca atccggccac cctcttccct ccttatgtag agatgatttc aacagagttt    2100
gttttgtagt tgtaacactt gcactcccag ttacagtttt gcattcgaca cattcatccc    2160
atcagatgtc aagtttaaag gcataagaca tttgacatat tgaagaagca gattaacacg    2220
aacgtcagta tgatgcttca gtgaagatat ggttgtaact tgtaaccaaa caaaagaaat    2280
gagactttga caaaaaaaaa aaaaaaaaaa aaaaaaaa                             2318

<210> SEQ ID NO 76
<211> LENGTH: 1503
<212> TYPE: DNA
<213> ORGANISM: Nicotiana benthamiana

<400> SEQUENCE: 76
atgagatcgg cgtcaaattc aaacgcaccc aataagcaat ggcgcaattg gttgcctctg      60
ttcgttgccc tagtgattat agctgagttt tcttttctgg ttcgactcga cgtagctgaa    120
aaagccaact cttgggccga atcgttttat cagttcacca cggcctcttg gtccacctct    180
aaactggctg ttgaccacgg cgacgttgag gaggtccagt tgggtgtttt gagtggtgag    240
ttcgatcatg gcttcgtacc tgggagttgc gaggagtggt tggaaaggga agattctgtg    300
gcttattcga gggattttga taatgaacca atttttgttc atgggcctgg acaggaattg    360
aaatcttgtt ccataggatg taagtttgga acagattcca ataagaagcc tgatgcagca    420
tttcggctac cacaacaagc tggcacagct agtgtgctac ggtcgatgga gtcagctcaa    480
tactatgcag agaacaacat tacttttggca cgacgaaggg gatatgatgt tgtaatgaca    540
acaagcctct cttcagatgt tcctgttgga tacttctctt gggctgagta tgatatcatg    600
gctccagtag aacctaaaac agagaatgcc ttggcagcgg ctttcatttc taattgtggt    660
gctcgcaact tccgtttgca agctttagaa gcccttgaaa gggcaaatat cagaattgac    720
tcttatggaa gttgtcatca taacagggat ggaagagttg acaaagtggc agcactgaag    780
cgttaccagt ttagcttggc ttttgagaat tctaatgagg aggactatgt aactgaaaaa    840
ttctttcagt ctctggtagc tgggtcaatc cctgtggtgg ttggtgctcc aaacatccaa    900
gactttgcgc cttctcctaa ttcagtttta cacattaaag agataaaaga tgctgaatca    960
attgccaata ccatgaagta ccttgctcaa aaccctattg catataatga gtcattaagg   1020
tggaagtttg agggcccatc tgatgccttc aaagcccttg ttgatatggc agcagttcat   1080
tcatcttgtc gtttgtgcat cttcttggca agtaggatcc gggaaagaga agagcagagt   1140
ccaaaattta tgaagcgtcc ctgcaaatgt accagaggga ctgaaactgt atatcatgta   1200
tatgtaggtg aaagaggcag gtttgagatg gattccattt tcttaaggtc gagtgatttg   1260
tctttgaagg cgtttgaatc tgctatcctc tcgaggttca agtctgttaa acatgttcct   1320
```

| | |
|---|---|
| gtttggaagg aggaaagacc tcaagtacta cgaggtggtg atgaactcaa actttacaaa | 1380 |
| gtatatcctg ttggcttgac acagagacaa gcattgtttt ccttcagatt caacggggat | 1440 |
| actgagttta acaattacat tcaaagccac ccatgtgcaa aatttgaagc catcttcgta | 1500 |
| tag | 1503 |

<210> SEQ ID NO 77
<211> LENGTH: 1503
<212> TYPE: DNA
<213> ORGANISM: Nicotiana benthamiana

<400> SEQUENCE: 77

| | |
|---|---|
| atgagatcgt cgtcaaattc aaacgcaccc gataaacaat ggcgcaattg gttgcctctg | 60 |
| ttcgttgccc tagttgttat agcagaaatt tcttttctgg ttcgactcga cgtggctgaa | 120 |
| aaagccaact cttgggctga gtcgttttat cagttcacca cggcgtcttg gtcaacctcc | 180 |
| aaactggctg ttgacggcgg cgatgttgat gaggtcctgt tgggtgtttt gagtggtgag | 240 |
| tttgatcagg gcttcctacc ttggagttgc gaggagtggt tggaaaggga agattatgtg | 300 |
| gcttattcga gggattttga taatgaacca attttttgttc atgggcctgg acaggaattg | 360 |
| aaatcttgtt ccataggatg taagtttgga acagattcca ataagaagcc tgatgcagca | 420 |
| tttcggctac cacaacaagc tggcacagct agtgtgctac ggtcgatgga gtcagctcaa | 480 |
| tactatgcag agaacaacat tactttggca cgacgaaggg gatatgatgt tgtaatgaca | 540 |
| acaagcctct cttcagatgt tcctgttgga tacttctctt gggctgagta tgatatcatg | 600 |
| gctccagtag aacctaaaac agagaatgcc ttggcagcgg cttcatttc taattgtggt | 660 |
| gctcgcaact tccgtttgca agctttagaa gcccttgaaa gggcaaatat cagaattgac | 720 |
| tcttatggaa gttgtcatca taacagggat ggaagagtag acaaagtggc agcactgaag | 780 |
| cgttacaagt ttagcttggc ttttgagaat tctaatgagg aggactatgt aaccgaaaaa | 840 |
| ttctttcagt ctctggtagc tgggtcaatc cctgtggtgg ttggtgctcc aaacatccaa | 900 |
| gactttgcgc cttctcctaa ttcagttttta cacattaaag agataaaaga tgctgaatta | 960 |
| attgccaata ccatgacgta ccttgctcaa aaccctattg catctaatga gtcattaagg | 1020 |
| tggaagtttg agggcccatt tgatgccttc aaagccctgg ttgatatggc agcagttcat | 1080 |
| tcatcttgcc gtttgtgcat cttcttggca agtaggatcc aggaaagaga agagcatagt | 1140 |
| ccaaaattta cgaagcgccc ctgcaaatgt accagagaga ctgaaactgt ctatcatgta | 1200 |
| tatgtacgtg aaagagggag gtttgagatg gattccattt tcttaaggtc gagtgatttg | 1260 |
| tctttaaagg cgtttgaatc tgctattctc tcgaggttca agtctgttaa acatgttcct | 1320 |
| gtttggaggg aggaaagacc tcaagtacta cgaggtggtg atgaactcaa actttactaa | 1380 |
| gtatatcctg ttggcttgac acagagacaa gcattgtttt ccttcagatt caacggggat | 1440 |
| actgagttta agaattacat tcaaagccac ccatgtgcaa aatttgaagc catcttcgta | 1500 |
| tag | 1503 |

<210> SEQ ID NO 78
<211> LENGTH: 2084
<212> TYPE: DNA
<213> ORGANISM: Nicotiana tabacum

<400> SEQUENCE: 78

| | |
|---|---|
| aaccccccccc cccccccacc cccaactgtc ccaccaaatg aagaattccc aaaccctctg | 60 |
| aagaagaaga aaaaaagatc acatctttag ctatttttact tccacaaaaa gaacaaaatt | 120 |

```
tcgagttatt aatggcaaca gttattccaa ttcaaaggtt accaagattt gaaggtgttg      180
ggtcatcatc acctacaaac gttcccctta agaaatggtc caattggcta cctctagtag      240
ttgcacttgt ggttatagtt gaaattacat ttctgggtcg actggacatg gctgaaaaag      300
ccaacctggt caactcttgg actgactcat tttaccagtt tacgacgtcg tcttggtcaa      360
cctccaaagt ggaaattagt gagactgggt tgggtgtgtt gaggagtagt gaggttgatc      420
ggaatttgga aactgggagc tgtgaggagt ggttggaaaa ggaggattct gtggagtatt      480
ctagagattt tgacaaagac ccaattttg ttcatggcgg cgaaaaggat tggaagtctt       540
gtgccgtagg atgtaacttt ggtgtggatt ctgaaaagaa gcctgatgcg gcatttggga      600
caccacaaca ggctggcacg gctagcgtgc ttcggtcaat ggagtcagct caatactatc      660
ctgagaacaa catcgttatg gcacgacgaa ggggatatga tattgtaatg acaacaagcc      720
tctcttcgga tgttcctgtt gggtacttct cttgggcgga gtatgatata atggctccag      780
tgcaacctaa aactgagaat gcgttagcag ctgcttttat ttctaattgt ggtgctcgca      840
acttccggtt acaggctctt gaagtccttg aaagggcaaa tatcaagatt gattcttttg      900
gcagttgtca tcgtaaccgg gatggaaatg tggacaaagt ggaaactctc aagcgctata      960
aatttagctt cgcttttgag aattctaatg aggaggatta tgtcaccgaa aaattcttcc     1020
agtctctggt agctggatca gtccctgtgg tgattggtgc tccaaacatc ctagactttg     1080
ctccttctcc taattcactt ttacacatta aagagctgaa agacgctgca tcagttgccg     1140
agactatgaa gtaccttgca gaaaatccta gtgcatataa tgagtcatta aggtggaagc     1200
ttgacggtcc atctgactct ttcaaagccc tggttgacat ggcagcagtt cactcttctt     1260
gtcgtttgtg tatcttctta gcaactagta ttagggagaa agaagagaag agtccagaat     1320
ttacaaaacg tccctgcaaa tgtaccagag gttcagaaac tgtctatcat atatatgtac     1380
gtgaaagagg gaggtttgac atggagtcca ttttcctaag gtcatctaat ttgtcattgg     1440
aggcttttga atctgcagta ctgtcgaagt tcaaatcttt aaagcatgtt cccatttgga     1500
aagaagaaag acctcaaata ctacgcggag gggatgaact aaagctctac agggtatatc     1560
ctctcggcat gacacaacga caggcattgt acacctccag attcaaagga gacgccgatt     1620
ttaggaatca catcgaaagc cacccatgtg caaattttga agccatattt gtatagatca     1680
agtccaaacc tgagagtctc gacagcagct tgttgtaggc catagcgtaa tgctcattct     1740
tactctatgc cccactgtct aacatcattc tggttatgaa ttcgtcgtgt agagtaagga     1800
tttgattatt acatggggcc aacctaattt tgggtggaaa gtactgatct tttacattta     1860
caagtaagaa ggaacaaact ctgaaccttg aatggacatg cctaacctcc caaagttgtg     1920
cagttgggaa attgcgggtg atatacaaac ttggacttgg ttttgctagc agaaaattct     1980
agctgatcaa tttgtaatct agttcagagg acatctccat cgtgttacaa gtaatgacaa     2040
gtgcagaaac taattaaagg ttcttttcgg aaaaaaaaaa aaaa                       2084
```

<210> SEQ ID NO 79
<211> LENGTH: 9
<212> TYPE: PRT
<213> ORGANISM: Artificial Sequence
<220> FEATURE:
<223> OTHER INFORMATION: synthetic peptide

<400> SEQUENCE: 79

Leu Ala Gly Leu Ile Asp Ala Asp Gly
1               5

<210> SEQ ID NO 80
<211> LENGTH: 82
<212> TYPE: DNA
<213> ORGANISM: Nicotiana benthamiana

<400> SEQUENCE: 80
atgagatcgg cgtcaaattc aaacgcaccc aataagcaat ggcgcaattg gttgcctctg     60
ttcgttgccc tagtgattat ag                                             82

<210> SEQ ID NO 81
<211> LENGTH: 69
<212> TYPE: DNA
<213> ORGANISM: Artificial Sequence
<220> FEATURE:
<223> OTHER INFORMATION: synthetic oligonucleotide

<400> SEQUENCE: 81
atgagatcgg cgtcaaattc aaacgcaccc aataagcatt gcctctgttc gttgccctag     60
tgattatag                                                            69

<210> SEQ ID NO 82
<211> LENGTH: 82
<212> TYPE: DNA
<213> ORGANISM: Nicotiana benthamiana

<400> SEQUENCE: 82
atgagatcgt cgtcaaattc aaacgcaccc gataaacaat ggcgcaattg gttgcctctg     60
ttcgttgccc tagttgttat ag                                             82

<210> SEQ ID NO 83
<211> LENGTH: 68
<212> TYPE: DNA
<213> ORGANISM: Artificial Sequence
<220> FEATURE:
<223> OTHER INFORMATION: synthetic oligonucleotide

<400> SEQUENCE: 83
atgagatcgt cgtcaaattc aaacgcaccc gataagcttg cctctgttcg ttgccctagt     60
tgttatag                                                             68

<210> SEQ ID NO 84
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 84
atgagatcgg cgtcaaattc aaacgcaccc aatgcctctg ttcgttgccc tagtgattat     60
ag                                                                   62

<210> SEQ ID NO 85
<211> LENGTH: 70
<212> TYPE: DNA
<213> ORGANISM: Artificial Sequence
<220> FEATURE:
<223> OTHER INFORMATION: synthetic oligonucleotide

<400> SEQUENCE: 85
atgagatcgg cgtcaaattc aaacgcaccc aataagcaat tgcctctgtt cgttgcccta     60

```
gtgattatag                                                              70

<210> SEQ ID NO 86
<211> LENGTH: 69
<212> TYPE: DNA
<213> ORGANISM: Artificial Sequence
<220> FEATURE:
<223> OTHER INFORMATION: synthetic oligonucleotide

<400> SEQUENCE: 86
atgagatcgt cgtcaaattc aaacgcaccc gataaacaat gcctctgttc gttgccctag     60
ttgttatag                                                              69

<210> SEQ ID NO 87
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 87
atgagatcgt cgtcaaattc aaacgcaccc gataaacaat ggcgcatgtt gcctctgttc     60
gttgccctag ttgttataag                                                  80

<210> SEQ ID NO 88
<211> LENGTH: 82
<212> TYPE: DNA
<213> ORGANISM: Nicotiana benthamiana

<400> SEQUENCE: 88
atgaacaaga aaagctgaa aattcttgtt tctctcttcg ctctcaactc aatcactctc      60
tatctctact tctcttccca cc                                               82

<210> SEQ ID NO 89
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 89
atgaacaaga aaagctgaa aattcttgtt tctctcttcg ctctcaacta tcctatctct      60
acttctcttc ccacc                                                       75

<210> SEQ ID NO 90
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 90
atgaacaaga aaagctgaa aattcttgtt tctctcttcg ctctcaactc aactatctct      60
acttctcttc ccacc                                                       75

<210> SEQ ID NO 91
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 91
```

```
atgaacaaga aaaagctgaa aattcttgtt tctctcttcg ctctcaactc tctatctcta    60
cttctcttcc cacc                                                      74
```

<210> SEQ ID NO 92
<211> LENGTH: 75
<212> TYPE: DNA
<213> ORGANISM: Artificial Sequence
<220> FEATURE:
<223> OTHER INFORMATION: synthetic oligonucleotide

<400> SEQUENCE: 92

```
atgaacaaga aaaagctgaa aattcttgtt tctctcttcg ctctcaactc aatcttctct    60
acttctcttc ccacc                                                     75
```

<210> SEQ ID NO 93
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 93

```
atgaacaaga aaaagctgaa aattctatct ctacttctct tcccacc                  47
```

<210> SEQ ID NO 94
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 94

```
atgaacaaga aaaagctgaa aattcttgtt tctctcttcg ctctcaactc aattctatct    60
ctacttctct tcccacc                                                   77
```

<210> SEQ ID NO 95
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 95

```
atgagatcgg cgtcaaattc aaacgcaccc aattatag                            38
```

<210> SEQ ID NO 96
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 96

```
atgagatcgt cgtcaaattc aaacgcaccc gataaacaat ggcgcttggt tgcctctgtt    60
cgttgcccta gttgttatag g                                              81
```

<210> SEQ ID NO 97
<211> LENGTH: 42
<212> TYPE: DNA
<213> ORGANISM: Artificial Sequence
<220> FEATURE:
<223> OTHER INFORMATION: synthetic oligonucleotide

<400> SEQUENCE: 97
atgagatcgt cgtcaaattc aaacgcaccc gataaacaat gg    42

<210> SEQ ID NO 98
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 98
atgaacaaga aaagctgaa aattcttgtt tctctcttcg ctctcaactc aatcctatct    60
ctacttctct tcccacc    77

<210> SEQ ID NO 99
<211> LENGTH: 76
<212> TYPE: DNA
<213> ORGANISM: Artificial Sequence
<220> FEATURE:
<223> OTHER INFORMATION: synthetic oligonucleotide

<400> SEQUENCE: 99
atgaacaaga aaagctgaa aattcttgtt tctctcttcg ctctcaactc aatctatctc    60
tacttctctt cccacc    76

<210> SEQ ID NO 100
<211> LENGTH: 656
<212> TYPE: DNA
<213> ORGANISM: Nicotiana benthamiana

<400> SEQUENCE: 100
aacaataagg ataataacaa ctcaatataa ttttaattag taggatctag gaagaataat    60
gtgtatataa atcttatttc tgtcatggat agagaggttg tcccgaaata gaaaaatttt   120
atgcttcaaa ttttgaaata aagtaatctt tttaaaaaaa tactatataa agtgtaatta   180
caactcaaat aatcatattt aactaacatc gttaaaccct ctgtactaag tagtacagac   240
gaaaacagcc cgtgagagag agagagagag aggagaagaa gatgaacaag aaaaagctga   300
aaattcttgt ttctctcttc gctctcaact caatcactct ctatctctac ttctcttccc   360
accctgatca ctctcgtcgc aaatcccccc agaaccactt tcctcgtcg gaaaaccacc    420 atcataattt ccactcttca atcacttccc aatattccag gccttggcct attttgccct   480
cctacctccc ttggtctcaa acccctaatg ttgcttggag atcatgcgag ggttacttcg   540
gtaatggttt tactctcaaa gttgatcttc tcaaaacttc gccggagctt caccggaaat   600
tcggcgaaaa caccgtcttc ggagacggcg gatggtttag gtgtttcttc agtgag       656

<210> SEQ ID NO 101
<211> LENGTH: 107
<212> TYPE: DNA
<213> ORGANISM: Artificial Sequence
<220> FEATURE:
<223> OTHER INFORMATION: synthetic oligonucleotide

<400> SEQUENCE: 101
aacaataagg ataataacaa ctcaaaactt cgccggagct tcaccggaaa ttcggcgaaa    60
acaccgtctt cggagacggc ggatggttta ggtgtttctt cagtgag               107